(12) United States Patent
Talwerdi

(10) Patent No.: US 10,192,376 B2
(45) Date of Patent: Jan. 29, 2019

(54) SECURITY CHECKPOINT

(71) Applicant: SICPA HOLDING SA, Prilly (CH)

(72) Inventor: Mehdi Talwerdi, North Vancouver (CA)

(73) Assignee: SICPA HOLDING SA, Prilly (CH)

( * ) Notice: Subject to any disclaimer, the term of this patent is extended or adjusted under 35 U.S.C. 154(b) by 44 days.

(21) Appl. No.: 15/030,699

(22) PCT Filed: Oct. 6, 2014

(86) PCT No.: PCT/EP2014/071303
§ 371 (c)(1),
(2) Date: Apr. 20, 2016

(87) PCT Pub. No.: WO2015/058948
PCT Pub. Date: Apr. 30, 2015

(65) Prior Publication Data
US 2016/0247341 A1 Aug. 25, 2016

Related U.S. Application Data

(60) Provisional application No. 61/976,658, filed on Apr. 8, 2014, provisional application No. 61/893,864, filed on Oct. 21, 2013.

(51) Int. Cl.
*G07C 9/00* (2006.01)
*H04N 1/00* (2006.01)
(Continued)

(52) U.S. Cl.
CPC ............ *G07C 9/00158* (2013.01); *A61B 5/01* (2013.01); *A61B 5/024* (2013.01); *A61B 5/112* (2013.01);
(Continued)

(58) Field of Classification Search
CPC ........... A61B 5/01; A61B 5/024; A61B 5/112; A61B 5/14542; A61B 5/4509; B42D 9/04;
(Continued)

(56) References Cited

U.S. PATENT DOCUMENTS

| 4,205,772 A | 6/1980 | Liepold et al. |
| 5,615,622 A | 4/1997 | Moses et al. |

(Continued)

FOREIGN PATENT DOCUMENTS

| CA | 1171433 | 7/1984 |
| CN | 101206773 | 6/2008 |

(Continued)

OTHER PUBLICATIONS

International Search Report (ISR) dated Aug. 27, 2014 issued with respect to application No. PCT/EP2014/059227.
(Continued)

*Primary Examiner* — Dionne H Pendleton
(74) *Attorney, Agent, or Firm* — Muncy, Geissler, Olds & Lowe, P.C.

(57) ABSTRACT

A security checkpoint for verifying whether a user is an authorized user includes: (a) a one-way mirror for concealingly permitting the automated recordation of data concerning a person at the security checkpoint; and (b) recording equipment for recording the data, the recording equipment being concealed by the one-way mirror; wherein the recorded data is sent to an analysis device for analysis and depending on the result of the analysis of the recorded data, an exit gate moves from a closed to an open position; the security checkpoint also comprising a document scanner to scan a document carried by the person and further comprising a printer to print a stamp on an identity document.

20 Claims, 30 Drawing Sheets

(51) Int. Cl.
| | | |
|---|---|---|
| *B42D 9/04* | (2006.01) | |
| *A61B 5/01* | (2006.01) | |
| *A61B 5/024* | (2006.01) | |
| *A61B 5/11* | (2006.01) | |
| *A61B 5/145* | (2006.01) | |
| *A61B 5/00* | (2006.01) | |
| *G06K 9/00* | (2006.01) | |
| *G06K 15/02* | (2006.01) | |

(52) U.S. Cl.
CPC ........ *A61B 5/14542* (2013.01); *A61B 5/4509* (2013.01); *B42D 9/04* (2013.01); *G06K 9/00006* (2013.01); *G06K 15/02* (2013.01); *G07C 9/00007* (2013.01); *G07C 9/00087* (2013.01); *H04N 1/00795* (2013.01)

(58) Field of Classification Search
CPC ............... G06K 15/02; G06K 9/00006; G06K 9/06046; G06K 7/14; G07C 9/00007; G07C 9/00087; G07C 9/00158; H04N 1/00795; G01N 21/55; G06Q 10/10; F21S 2/00; G02F 1/133603; G02F 1/13306; G02F 1/1335; G02F 1/133528; G09F 9/00; G09F 9/46; G09G 3/36; A61C 19/003
See application file for complete search history.

(56) References Cited

U.S. PATENT DOCUMENTS

| | | | |
|---|---|---|---|
| 6,570,498 | B1 | 5/2003 | Frost et al. |
| 7,253,727 | B2 | 8/2007 | Jenkins et al. |
| 7,755,611 | B2 | 7/2010 | Barr |
| 7,850,077 | B2 | 12/2010 | Talwerdi et al. |
| 10,048,538 | B1 * | 8/2018 | Fukuoka ................ F21S 2/00 |
| 2001/0053967 | A1 * | 12/2001 | Gordon ................ G06Q 10/10 703/22 |
| 2003/0072568 | A1 | 4/2003 | Lin et al. |
| 2003/0163696 | A1 | 8/2003 | Rancien |
| 2004/0133804 | A1 | 7/2004 | Smith et al. |
| 2004/0228503 | A1 * | 11/2004 | Cutler ................ G06K 9/00348 382/103 |
| 2008/0100916 | A1 | 5/2008 | Suhl |
| 2008/0206018 | A1 | 8/2008 | Warwick et al. |
| 2009/0166410 | A1 | 7/2009 | Song |
| 2010/0073128 | A1 | 3/2010 | Talwerdi |
| 2010/0308108 | A1 | 12/2010 | Choi et al. |
| 2012/0199653 | A1 * | 8/2012 | Wenzel ............... G07C 9/00103 235/382 |
| 2012/0321136 | A1 * | 12/2012 | Lobean .............. G06K 9/00348 382/103 |
| 2013/0201286 | A1 * | 8/2013 | Schockmel ......... G07C 9/00111 348/46 |
| 2014/0078507 | A1 * | 3/2014 | Labrie .................. A61C 19/003 356/446 |

FOREIGN PATENT DOCUMENTS

| | | |
|---|---|---|
| CN | 101581166 | 11/2009 |
| CN | 201392554 | 1/2010 |
| CN | 102278050 | 12/2011 |
| CN | 102332197 | 1/2012 |
| CN | 202139953 | 2/2012 |
| DE | 29504660 U1 | 5/1995 |
| DE | 19537741 | 4/1997 |
| DE | 10223326 | 12/2003 |
| EP | 1520715 B1 | 8/2007 |
| JP | 0725095 | 1/1995 |

OTHER PUBLICATIONS

International Preliminary Report on Patentability (IPRP) dated Oct. 1, 2015 issued with respect to application No. PCT/EP2014/059227.
International Preliminary Report on Patentability (IPRP) dated Dec. 16, 2015 issued with respect to application No. PCT/EP2014/071303.
Chinese Office Action and Search Report in counterpart Chinese Application No. 201410756158.1 dated Oct. 27, 2017 (and English Language Translation).

* cited by examiner

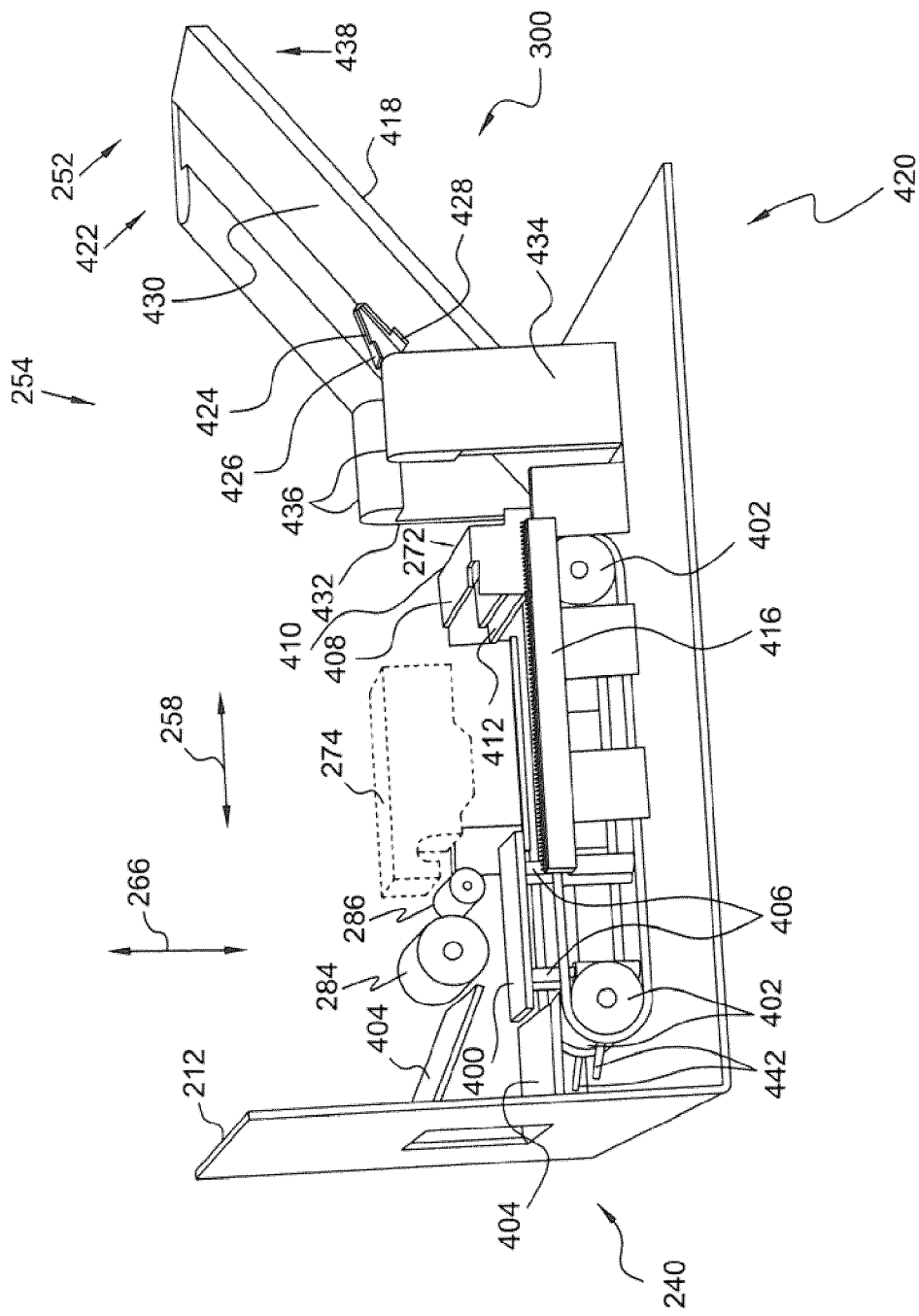

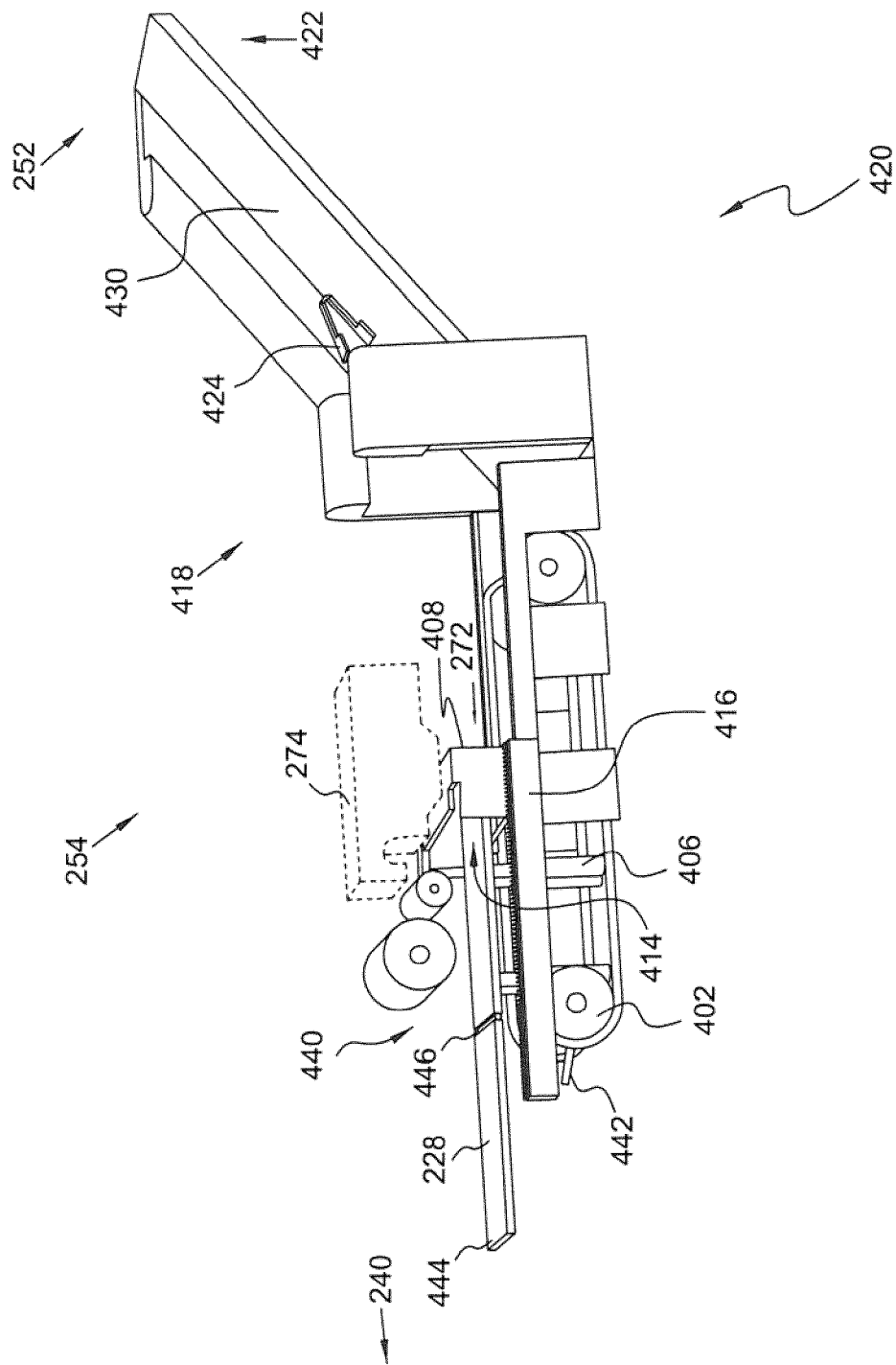

SECURITY CHECKPOINT

CROSS-REFERENCE TO RELATED APPLICATION

This application is a U.S. National Stage of International Application No. PCT/2014/071303 filed Oct. 6, 2014, which claims priority of U.S. Provisional Application Nos. 61/893,864 filed Oct. 21, 2013 and 61/976,658 filed Apr. 8, 2014. The disclosure of International Application No. PCT/2014/071303 is expressly incorporated by reference herein in its entirety.

BACKGROUND OF THE INVENTION

1. Field of Invention

This invention relates to a security checkpoint and a method of operating a security checkpoint.

2. Description of Related Art

Security checkpoints permit authorities, such as governments or private enterprises, to verify an individual's identity and other credentials of the individual prior to permitting that individual into a particular area. Security checkpoints can be found at borders, such as borders between countries and borders around restricted areas within countries and other exclusion zones; transportation hubs such as airports, train stations, bus stations, ports and shipping dockyards; event venues such as stadiums and concert halls; at and within buildings such as office buildings, political institutions and research facilities; construction sites; and other places where it is desired to confirm the identity of an individual or whether an individual is permitted to access a particular area.

A one-way mirror is half-silvered so that under appropriate lighting conditions it appears from a first side as an ordinary reflective mirror, yet permits viewing from the second (opposite) side of any individuals or objects present at the first side.

U.S. Pat. No. 7,253,727 to Jenkins et al. discloses a security checkpoint particularly suitable for use at an airport in which the level of checking at locations in the security checkpoint can be made with consideration for observations made by the ticket agent at check-in or by information maintained in databases of security agencies or suspicious activity detected automatically by video sensing equipment. However, the security checkpoint of Jenkins et al. relies on non-automated observations of a human ticket agent and does not make use of a one-way mirror for enhanced automated security.

U.S. Pat. No. 7,755,611 to Barr discloses a decorative mirror that includes an audio/visual output and a transparent touch screen input device which together provide a user interface apparatus to a home security system. Barr discloses a security activation feature for identification of a user and activation of the user interface apparatus to prevent it being unintentionally revealed as a security system or a home automation system interface rather than merely a mirror. The security activation feature may be a proximity sensor aimed outwardly through an aperture in the frame surrounding the mirror, in order to activate the user interface apparatus. The security activation feature may be used in combination with a touch to a particular location of the touch screen panel. An alternative embodiment could include a fingerprint scanner, a retinal scanner, voice recognition facility or other personal identification device located on, adjacent to, or concealed within the user interface apparatus. However, the decorative mirror of Barr does not provide the full security functions required of an automated security checkpoint.

Documents, including passports and other bound (booklet-type) documents, birth certificates and other unbound documents, identification cards, security badges and licenses; value items, including value documents, products and product labels; and other objects, are known to be subject to authentication and verification processes for determining whether a given object is authentic (i.e. untampered). Generally, a documents is defined as having human or machine-readable text thereon. Generally, a value item is defined as having value to its owner, user, person in possession thereof, and/or other associated person(s). Generally, an object is defined as having a definable shape at a given point in time.

Printers are known to print text, graphic symbols, stamps, indicia and other markings on bound and unbound documents, value items and other objects.

However, conventional readers are not able to print on the document, value item or other object being authenticated, and conventional printers are not able to read for authentication and verification.

Known printers include a pair of parallel rollers spaced apart by a small gap through which the document is moved by motorized action of the rollers. Such motorized rollers must provide a rolling surface made of a high-friction material such as rubber to avoid slippage of the document. However, such high-friction material can wear out and need to be replaced, which increases the maintenance requirements of the known printers and/or reduces the lifespan of the known printers.

European patent No. 1 520 715 B1 dated 8 Aug. 2007 discloses a printer having a motorized tray in which a book-like document sits when the motorized tray is transporting the document in and out of a printing zone of the printer. The motorized tray has a mechanism for clamping all four edges of the document to avoid movement of the document relative to the motorized tray during transportation. While the motorized tray and its mechanism for clamping all four edges of the document can be made of long-lasting materials such as metal, the motorized tray and its mechanism is bulky, thereby impeding rapid movement of the document in and out of the printing zone.

SUMMARY

In accordance with a first aspect there is provided a security checkpoint comprising:

(a) a one-way mirror for concealingly permitting the automated recordation of data concerning a person at the security checkpoint; and
(b) recording equipment for recording said data, said recording equipment being concealed by said one-way mirror.

Typically, the apparatus further comprises a processor to control the operation and functions of the apparatus.

The recording equipment may include a camera. The camera may be a still-image camera for capturing still images. The camera may be a video camera for capturing video information. The camera may be a video camera for capturing audio-video information. The camera may be an IR (infrared) camera operable to capture images in the IR (infrared) region of the electromagnetic spectrum. The camera may be an IR camera operable to capture video information in the IR region of the electromagnetic spectrum.

The camera may be a thermographic camera. The camera may be an UV (ultraviolet) camera operable to capture images in the UV (ultraviolet) region of the electromagnetic spectrum. The camera may be an UV camera operable to capture video information in the UV region of the electromagnetic spectrum. The camera may be a stereoscopic camera for capturing three-dimensional images. The camera may be a stereoscopic camera for capturing three-dimensional video information. The camera may be a stereoscopic camera for capturing three-dimensional video information and audio information. The recording equipment may include a plurality of cameras of the same type. The recording equipment may include a plurality of cameras of different types. The recording equipment may include an array of cameras. The recording equipment may include multiple arrays of cameras.

The recording equipment may include an audio recorder. The recording equipment may include a proximity detector. The recording equipment may include a thermal detector. The recording equipment may include a thermal sensor. The recording equipment may include a tactile sensor. The recording equipment may include a vibration sensor. The recording equipment may include a document scanner. The recording equipment may include a card scanner. The recording equipment may include a line-type scanner. The line-type scanner may include a photodiode for detecting electromagnetic radiation reflected from or transmitted through a card or other object as the photodiode and the object move relative to each other. The recording equipment may include an image scanner. The document scanner may be a line-type scanner. The document scanner may be an image scanner. The card scanner may be a line-type scanner. The card scanner may be an image scanner. The recording equipment may include a magnetic energy detector. The recording equipment may include a fingerprint detector. The recording equipment may include a palm-print detector. The recording equipment may include a display controller for controlling displays of information on the one-way mirror. The recording equipment may include a touchscreen controller for controlling the reception of touchscreen user input applied to the one-way mirror.

Additional examples of possible recording equipment are: a microphone for recording the sound from the user such as the user's voice, ultrasound transducers for measuring bone density, an infrared radiation emitters (such as a near infrared radiation source) and detectors (such as a monochrome charge coupled device array camera) to image a vascular pattern of a user, a pulse oximeter to measure oxygen content of blood, cameras to monitor behavior and/or record other biometric movements of the user such the user's gait and/or to record other biometric data from a user such as geometry of body (for example finger, hand and/or ear lobe geometry).

The recording equipment may include a source of lighting. The recording equipment may include a source of electromagnetic radiation. The recording equipment may include a source of magnetic energy. The recording equipment may include a magnet. The recording equipment may include a source of electromagnetic radiation in the IR region of the electromagnetic spectrum. The recording equipment may include a source of electromagnetic radiation in the visible light region of the electromagnetic spectrum. The recording equipment may include a source of electromagnetic radiation in the UV region of the electromagnetic spectrum. The recording equipment may include a laser. The recording equipment may include a light-emitting diode (LED). The recording equipment may include a heat source.

The security checkpoint may include a housing for containing the recording equipment. The housing may support the one-way mirror. The housing may include a mirror frame for supporting the one-way mirror. The mirror frame may extend around the perimeter of the one-way mirror. The mirror frame may be made of transparent material. The mirror frame may be made of translucent material. The mirror frame may be made of opaque material. The housing may contain frame equipment. The frame equipment may be disposed adjacent to the mirror frame. The frame equipment may be disposed proximate to the mirror frame.

The frame equipment may include a camera. The frame equipment may include a plurality of cameras of the same type. The frame equipment may include a plurality of cameras of different types. The frame equipment may include an array of cameras. The frame equipment may include multiple arrays of cameras. The frame equipment may include an audio recorder. The frame equipment may include a proximity detector. The frame equipment may include a thermal detector. The frame equipment may include a thermal sensor. The frame equipment may include a tactile sensor. The frame equipment may include a vibration sensor. The frame equipment may include a magnetic energy detector. The frame equipment may include an ultrasound detector. The frame equipment may include an ultrasonic transducer. The frame equipment may include an ultrasonic transceiver. The frame equipment may include a motion detector. The frame equipment may include a source of lighting. The frame equipment may include a source of electromagnetic radiation. The frame equipment may include a source of magnetic energy. The frame equipment may include a magnet. The frame equipment may include an IR (infrared) source. The frame equipment may include a visible light source. The frame equipment may include an UV (ultraviolet) source. The frame equipment may include a laser. The frame equipment may include a light-emitting diode (LED). The frame equipment may include a heat source.

The security checkpoint may include a fingerprint scanner. The fingerprint scanner may be unconcealed. The security checkpoint may include a palm-print scanner. The palm-print scanner may be unconcealed. The security checkpoint may include a document scanner. The document scanner may be unconcealed. the document scanner may include an input slot dimensioned for receiving documents. The security checkpoint may include a card scanner. The card scanner may be unconcealed. The security checkpoint may include a line-type scanner. The line-type scanner may be unconcealed. The security checkpoint may include an image scanner. The image scanner may be unconcealed. The security checkpoint may include a printer. The printer may be unconcealed. The printer may be a thermal printer. The thermal printer may be unconcealed. The printer may be an ink jet printer. The printer may be in an integrated reader-printer apparatus for authenticating and printing on a value item or other object such as the one described herein. The security checkpoint may include stamping equipment. The stamping equipment may be unconcealed. The security checkpoint may include a checkpoint camera. The checkpoint camera may be unconcealed. The checkpoint camera may be concealed. The checkpoint camera may be located other than behind the one-way mirror. The checkpoint camera may be concealed and located other than behind the one-way mirror. The security checkpoint may include a checkpoint LED. The checkpoint LED may be unconcealed. The security checkpoint may include a speaker. The speaker may be unconcealed. The security checkpoint may include a microphone. The microphone may be unconcealed. The security checkpoint may include a display. The display may be unconcealed. The display may be a liquid crystal display (LCD). The security checkpoint may include an ultrasound detector. The ultrasound detector may be unconcealed. The security checkpoint may include an ultrasonic transducer. The ultrasound transducer may be unconcealed. The security checkpoint may include an ultrasonic transceiver. The ultrasound transceiver may be unconcealed. The security checkpoint may include an exit gate. The security checkpoint may include an exit doorway. The security checkpoint may include an entrance gate. The security checkpoint may include an entrance doorway.

The security checkpoint may include a controller for controlling automated operations of the security checkpoint. The controller may be housed within the housing. The controller may be concealed. The controller may be unconcealed. The controller may include a processor. The controller may include a memory. The controller may include a database. The controller may include a plurality of databases. The controller may include a connection bus. The controller may include a communications controller. The communications controller may be operable to establish wired communications with a network. The communications controller may be operable to establish wireless communications with a network.

The security checkpoint may include a security console. The security console may include a one-way mirror. The security console may include recording equipment. The security console may include recording equipment hidden behind the one-way mirror of the security console. The security console may be disposed within an enclosure. The enclosure may include a one-way mirror. The security checkpoint may include recording equipment hidden behind the one-way mirror of the enclosure. The enclosure may include an entrance doorway. The enclosure may include an exit doorway. The exit doorway may include a one-way mirror. The exit doorway may include recording equipment. The exit doorway may include recording equipment hidden behind the one-way mirror of the exit doorway.

In accordance with another aspect of the invention, there is provided a method of recording data concerning a person at a security checkpoint. The method involves: (a) concealingly permitting by a one-way mirror of the security checkpoint the automated recordation of data concerning the person at the security checkpoint; and (b) recording the data by recording equipment of the security checkpoint when the recording equipment is being concealed by the one-way mirror.

The method may involve setting to a default state. Setting to a default state may involve locking the exit gate. Locking the exit gate may involve closing the exit gate. Setting to a default state may involve activating overhead lighting. Setting to a default state may involve activating floor lighting. Setting to a default state may involve de-activating backlighting of the one-way mirror. Setting to a default state may involve de-activating lighting at a frame of the one-way mirror. Setting to a default state may involve displaying a default image on a display. Setting to a default state may involve de-activating lighting associated with a fingerprint scanner. Setting to a default state may involve de-activating lighting associated with a document scanner. Setting to a default state may involve displaying a do-not-enter symbol on a display.

The method may involve determining whether a person is present at the security checkpoint. The method may involve determining the number of persons present at the security checkpoint. The method may involve determining whether an unauthorized object is present at the security checkpoint. The method may involve determining the number of unauthorized objects present at the security checkpoint.

The method may involve triggering an alarm condition. Triggering an alarm condition may involve communicating a message to a security station. Triggering an alarm condition may involve displaying instructions on a display. Triggering an alarm condition may involve issuing voice commands. Triggering an alarm condition may involve adjusting lighting conditions associated with the security checkpoint. Triggering an alarm condition may involve closing the exit gate. Triggering an alarm condition may involve locking the exit gate. Triggering an alarm condition may involve closing the exit doorway. Triggering an alarm condition may involve locking the exit doorway. Triggering an alarm condition may involve unlocking the entrance doorway. Triggering an alarm condition may involve opening the entrance doorway.

The method may involve displaying instructions. The method may involve displaying instructions on a display. The method may involve displaying instructions for a next person to enter the security checkpoint. The method may involve issuing voice commands. The method may involve issuing voice commands using a speaker. The method may involve presenting language options to a person for selection. The method may involve receiving user input. The method may involve receiving user input via a touchscreen display. The method may involve receiving audio user input via a microphone. The method may involve receiving as user input a selection of language.

The method may involve prompting a person to present a document. Prompting a person to present a document may involve prompting a person to present a document at the document scanner. Prompting a person to present a document may involve prompting a person to present a document at the one-way mirror. Prompting a person to present a document may involve prompting a person to present an identity document. Prompting a person to present a document may involve prompting a person to present a payment card. The method may involve receiving a document for scanning. The method may involve receiving a document for scanning at the one-way mirror. The method may involve scanning a document. The method may involve automatedly reading a document. The method may involve scanning a document at the one-way mirror. The method may involve storing data produced by scanning a document. The method may involve comparing data produced by scanning a document with previously stored data concerning the document.

The method may involve prompting a person to present their finger for fingerprint scanning. The method may involve prompting a person to present their finger for fingerprint scanning at the one-way mirror. The method may involve prompting a person to present their palm for palm-print scanning. The method may involve prompting a person to present their palm for palm-print scanning at the one-way mirror. The method may involve measuring a temperature associated with a human body part. The method may involve measuring a temperature associated with an object presented for fingerprinting. The method may involve measuring a temperature associated with an object presented for palm-printing.

The method may involve prompting a person to face the one-way mirror. The method may involve collecting user information. Collecting user information may involve displaying a request for information on a display. Collecting user information may involve displaying a plurality of menu selections. Collecting user information may involve issuing a voice command. Collecting user information may involve receiving user input. Collecting user information may involve receiving as user input touchscreen manipulations. Collecting user information may involve receiving as user input audio information. Collecting user information may involve using a camera to capture one or images of a person, the images captured may be still photos and/or videos. Collecting user information may involve receiving payment. The method may involve collecting biometric data. Collecting biometric data may involve imaging biometric features of a person, such as a person's gait (or in other words, the way in which a person walks). Collecting biometric data may involve imaging facial features of a person. Collecting biometric data may involve imaging iris features of a person. Collecting biometric data may involve imaging bodily features of a person, such as geometrical features of the fingers and/or palms and/or ear lobes and/or vascular patterns. Collecting biometric data may involve detecting biometric features of a person. Collecting biometric data may involve sensing biometric features of a person. Collecting biometric data may involve imaging biometric features of a person while the person is under exposure to IR radiation, such as vascular patterns. In the example of imaging vascular patterns, near infrared radiation is typically used to illuminate a body part, such as finger or hand. Collecting biometric data may involve imaging biometric features of a person while the person is under exposure to UV radiation. Collecting biometric data may involve producing IR images of biometric features of a person. Typically, at least in the case of obtaining IR images of vascular patterns, the images could be captured using a monochrome camera, such as a monochrome charge-coupled device (CCD) array camera. Collecting biometric data may involve producing UV images of biometric features of a person. Collecting biometric data may involve measuring heat generated by a person. Collecting biometric data may involve receiving audio information associated with a person, such as voice recording to perform voice recognition analysis.

The method may involve determining whether the collected user information is accepted by the security checkpoint. Determining whether the collected user information is accepted by the security checkpoint may involve quantifying risk factors associated with the user information. Determining whether the collected user information is accepted by the security checkpoint may involve comparing the collected user information to previously stored data. The method may involve determining whether the collected biometric data is accepted by the security checkpoint. Determining whether the collected biometric data is accepted by the security checkpoint may involve quantifying risk factors associated with the biometric data. Determining whether the collected biometric data is accepted by the security checkpoint may involve comparing the collected biometric data to previously stored data. Determining whether the collected biometric data is accepted by the security checkpoint may involve performing automated facial recognition analysis. Determining whether the collected biometric data is accepted by the security checkpoint may involve performing automated handwriting analysis. Determining whether the collected biometric data is accepted by the security checkpoint may involve performing automated voice recognition analysis.

The method may involve performing behavioral analysis associated with a person. The method may involve obtaining the results of behavioral analysis associated with a person. Performing behavioral analysis may involve analyzing behavioral data. Performing behavioral analysis may involve analyzing behavioral data collected about the person at the security checkpoint. Performing behavioral analysis may involve performing automated visual analysis. Performing behavioral analysis may involve performing automated visual analysis. Performing behavioral analysis may involve performing automated audio analysis. Performing behavioral analysis may involve performing automated speech analysis. Performing behavioral analysis may involve comparing behavioral data with previously stored data. Performing behavioral analysis may involve comparing behavioral data with known behavioral templates.

The method may involve determining whether automated behavioral analysis results are accepted by the security checkpoint. Determining whether the behavioral analysis results are accepted by the security checkpoint may involve comparing the results to one or more threshold values.

The method may involve unlocking the exit gate. The method may involve opening the exit gate. The method may involve closing the exit gate. The method may involve locking the exit gate. The method may involve unlocking the exit doorway. The method may involve opening the exit doorway. The method may involve closing the exit doorway. The method may involve locking the exit doorway. The method may involve unlocking the entrance doorway. The method may involve opening the entrance doorway. The method may involve closing the entrance doorway. The method may involve locking the entrance doorway.

The method may involve checking the operating status of the security checkpoint. The method may involve checking parameter values associated with the controller.

In accordance with another aspect, there is provided apparatus for reading and printing on
  an object, the apparatus comprising:
  (a) a reader system for reading the object to obtain a digital signature representing a unique feature of the object; and
  (b) a printer system for printing on the object if the digital signature matches a reference digital signature associated with the object.

In accordance with yet another aspect, there is provided an integrated reader-printer apparatus for authenticating and printing on an object. Said integrated reader-printer apparatus may be used and/or integrated in the security checkpoint described herein. The reader-printer apparatus includes: a reader system for reading and authenticating an object; and a printer system for printing on the object. The object may be a document. The object may be a value item. The value item may be a document. The document may be a bound document. The document may be an unbound document. The document may be one or more paper sheets. The document may be a booklet. The value item may be a card. The document may be a card. The document may be a certificate. The value item may be a product. The value item may be a product label. The document may be a label. The document may be a tag. The document may be a sticker.

The reader-printer apparatus may include a reader-printer processor. The reader-printer processor may include one or more processing circuits. The reader-printer apparatus may include a reader-printer memory. The reader-printer memory may include one or more memory circuits. The reader-printer apparatus may include a communications system for providing communications between the reader-printer apparatus and other devices. The reader-printer apparatus may include a location identification system for identifying the location of the reader-printer apparatus. The reader-printer apparatus may include a biometric scanning system for performing biometric scans of a user of the reader-printer apparatus. The reader-printer apparatus may include a reader-printer housing for enclosing components of any one or more of the reader system, printer system, reader-printer processor, reader-printer memory, communications system, location identification system and the biometric scanning system.

The reader system may include a reader system support for supporting the value item when the reader system is reading the value item. The reader system support may be plate-shaped. The reader system support may be substantially transparent. The reader system may include a receiving flange dimensioned for receiving the value item at the reader system support. The receiving flange may define a receiving slot. The receiving flange may be disposed at the perimeter of the reader system support. The receiving flange may extend along one or more perimeter sides of the reader system support. The receiving flange may extend along three of four perimeter sides of the reader system support. The receiving flange may project from the reader-printer housing. The receiving flange may form part of the reader-printer housing. The reader system may include a sensor for detecting the presence of the value item when the value item is being supported by the reader system support. The reader system may include a sensor for detecting the presence of the value item when the value item is being received by the receiving flange. The reader system may include a sensor disposed within a space defined between the reader system support and the receiving flange. The reader system may include sensors disposed at different perimeter sides of the reader system support. The reader system may include seven sensors disposed at each of three perimeter sides of the reader system support. The reader system may include three sensors disposed at each of the three perimeter sides of the reader system support. The reader system may include three sensors disposed at each of three sides of the receiving flange.

The reader system may include a source of electromagnetic radiation. The source of electromagnetic radiation may be positioned within the reader-printer housing to direct the electromagnetic radiation at the reader system support. The source of electromagnetic radiation may be operable to produce electromagnetic radiation having wavelengths in one or more ranges of the electromagnetic spectrum. The source of electromagnetic radiation may be operable to produce electromagnetic radiation having wavelengths in the infrared range. The source of electromagnetic radiation may be operable to produce electromagnetic radiation having wavelengths in the visible light range. The source of electromagnetic radiation may be operable to produce electromagnetic radiation having wavelengths in the ultraviolet range. The source may include a light-emitting diode (LED).

The reader system may include an imaging device for producing images. The imaging device of the reader system may be mounted within the reader-printer housing. The reader system imaging device may be operable to capture images of the value item when the value item is being supported by the reader system support. The reader system imaging device may be operable to capture images of the value item when the source is producing electromagnetic radiation.

The reader system may be operable to authenticate the value item. The reader system may be dimensioned to be removable from the reader-printer housing. The reader system may include an enclosure enclosing the reader system when the reader system is removed from the reader-printer housing.

The printer system may include printer system components mounted within the reader-printer housing. The reader-printer housing may include an inlet aperture defining a printer inlet. The reader-printer housing may include an inlet access door disposed at the printer inlet. The inlet access door may be an inlet flap. The printer system may be operable to close the inlet access door. The printer system may be operable to lock the inlet access door when the inlet access door is closed. The printer system may be operable to unlock the inlet access door. The printer system may be operable to open the inlet access door.

The reader-printer housing may include an outlet aperture defining a printer outlet. The reader-printer housing may include an outlet access door disposed at the printer outlet. The outlet access door may be an outlet flap. The printer system may be operable to close the outlet access door. The printer system may be operable to lock the outlet access door when the outlet access door is closed. The printer system may be operable to unlock the outlet access door. The printer system may be operable to open the outlet access door.

The reader-printer housing may include a printer inlet guide for guiding the value item through the printer inlet. The printer inlet guide may include one or more printer inlet guide walls. The printer inlet guide may include two printer inlet guide walls. The printer inlet guide may include four printer inlet guide walls. The printer inlet guide may project from the inlet aperture inwardly. The printer inlet guide may project within the reader-printer housing. The printer inlet guide may project toward a printer platen. The printer inlet guide may project toward a printing support.

The printer system may include a transport system for transporting the value item through the printer system. The transport system may include the printing support. The printing support may include the platen. The printing support may be a printing support plate. The printing support may be plate-shaped. The printing support may be dimensioned for supporting the value item. The printing support may be operable to support the value item. The reader system may include one or more support posts for supporting the printing support. The printing support may be attached to the support posts. The support posts may be telescopic. The printer system may be operable to move the printing support in a vertical direction by causing the support posts to move telescopically. The printer system may be operable to move the printing support in an upward vertical direction by causing the support posts to lengthen. The printer system may be operable to move the printing support in a downward vertical direction by causing the support posts to shorten.

The printing support may include a plurality of longitudinally adjacent printing support plates. One of the plurality of longitudinally adjacent printing support plates may be moveable in a vertical direction independently of another one of the plurality of longitudinally adjacent printing support plates. One of the plurality of longitudinally adjacent printing support plates may have a first vertical height and another one of the plurality of longitudinally adjacent printing support plates may have a second vertical height. The one of the plurality of longitudinally adjacent printing support plates may abut the another one of the plurality of longitudinally adjacent printing support plates when the one plate and the another plate are at the same vertical height. The one of the plurality of longitudinally adjacent printing support plates may be spaced apart from the another one of the plurality of longitudinally adjacent printing support plates so as to form a longitudinal gap therebetween. The printing support may include a plurality of transversely adjacent printing support plates. One of the plurality of transversely adjacent printing support plates may be moveable in a vertical direction independently of another one of the plurality of transversely adjacent printing support plates. One of the plurality of transversely adjacent printing support plates may have a first vertical height and another one of the plurality of transversely adjacent printing support plates may have a second vertical height. The one of the plurality of transversely adjacent printing support plates may abut the another one of the plurality of transversely adjacent printing support plates when the one plate and the another plate are at the same vertical height. The one of the plurality of transversely adjacent printing support plates may be spaced apart from the another one of the plurality of transversely adjacent printing support plates so as to form a transverse gap therebetween. The printing support may include a first pair of longitudinally adjacent printing support plates and a second pair of longitudinally adjacent printing support plates, the first pair being transversely adjacent to the second pair.

The transport system may include an entrance feeder. The entrance feeder may be mounted within the reader-printer housing. The entrance feeder may be mounted above the printing support. The entrance feeder may be dimensioned to limit the upward vertical movement of the printing support. The entrance feeder may include a roller. The roller may be free-spinning. The roller may be motorized. The motorized roller may be a bi-directionally motorized roller. The entrance feeder may include a plurality of rollers of different cross-sectional diameters. The plurality of rollers may be mounted such that the lowest points of their outer surfaces, respectively, are at a same vertical height. The plurality of rollers may be mounted such that a larger diameter roller is closer to the printer inlet than a smaller diameter roller.

The printer system may include a printhead for printing on the value item. The printer system may be operable to cause the printhead to move transversely. The roller may be mounted closer to the printer inlet than the printhead. The printing support may extend longitudinally closer to the printer inlet than the roller. The printing support may extend longitudinally so as to avoid extending as far from the printer inlet as the printhead. The printing support may extend longitudinally so as to avoid extending beneath the printhead. The printing support may extend longitudinally as far from the printer inlet as the printhead. The printing support may extend longitudinally to a point beneath the printhead. The platen may be dimensioned to support the booklet in proximity to the printhead. The platen may be dimensioned to support the booklet beneath the printhead. The platen may be dimensioned to support the booklet at a printing zone defined beneath the printhead.

The printer system may include a frame for clamping the value item at a leading edge of the value item (i.e. the first edge of the value item that is inserted into the reader-printer housing through the printer inlet). The printer system may be operable to cause the frame to move longitudinally. The printer system may be operable to cause the frame to move longitudinally along a toothed rail. The printer system may be operable to cause the frame to move longitudinally along a rack by operation of a pinion gear. The printer system may be operable to cause the frame to transport the value item by pulling the value item at its leading edge. The printer system may be operable to transport the value item from a receiving position of the printer system to an imaging position of the printer system. The printer system may be operable to transport the value item from the receiving position to a printing position of the printer system. The printer system may be operable to transport the value item from the imaging position to the printing position. The printing position may be defined as the position of the frame when the value item is beneath the printhead, including possibly when a printable area of the value item is beneath the printhead. The printer system may be operable to transport the value item from the printing position to a printed position of the printer system. The printer system may be operable to transport the value item from the printed position to an exit position of the printer system. The exit position may be defined as the position of the printer system when the value item is retrievable from outside of the reader-printer housing. The exit position may be defined as the position of the printer system when the value item is retrievable by the user from outside of the reader-printer housing. The exit position may be defined as the position of the printer system when the value item is retrievable by an automated module from outside of the reader-printer housing. The exit position may be defined as the position of the printer system when the value item is placed beyond the printer outlet.

The frame may include an upper frame member and a lower frame member. The printing support may extend longitudinally into the space defined between the upper frame member and the lower frame member. The upper frame member may be dimensioned to limit the upward vertical movement of the printing support. The printer system may be operable to clamp the value item between the printing support and the upper frame member. The printer system may be operable to clamp the value item between the lower frame member and the upper frame member. The printer system may be operable to release clamping of the value item.

The printer system may include a stopper. The printer system may be operable to activate the stopper so as to inhibit longitudinal movement of the value item beyond a definable point. The printer system may be operable to de-activate the stopper so as to not inhibit longitudinal movement of the value item. The stopper may be a gate. The printer system may be operable to close the gate so as to inhibit longitudinal movement of the value item beyond a definable point. The printer system may be operable to open the gate so as to not inhibit longitudinal movement of the value item. The stopper may be rotatably coupled to the frame. The stopper may be hingedly connected to the frame. The stopper may be slidably coupled to the frame.

The printer system may include a printer system imaging device for capturing images. The printer system imaging device may be mounted within the reader-printer housing. The printer system imaging device may be operable to capture images of the value item when the value item is being supported by the printing support. The printer system imaging device may be operable to capture images of the value item when the value item is being clamped by the frame. The printer system imaging device may be operable to capture images of a printable area of the value item when the value item is being clamped by the frame.

The printer system may include a transport conveyor for conveying the value item. The printer system may include a transport conveyor for conveying the value item when the printer system is in its printing position. The printer system may include a transport conveyor for conveying the value item when the printer system is in its printed position. The transport conveyor may include a transport conveyor belt having a push-plate projecting therefrom. The push-plate may be dimensioned to engage the value item. The push-plate may be dimensioned to engage the value item at one edge thereof. The transport conveyor may be operable to push the value item when the push-plate is contacting the value item. The transport conveyor may be operable to push the value item by the push-plate when the transport conveyor is conveying the value item. The transport conveyor may be mounted within the reader-printer housing for pushing the value item in a longitudinal direction. The transport conveyor may be mounted within the reader-printer housing for pushing the value item in a forward direction by making contact between the push-plate and a substantially central portion of the trailing edge of the value item. The transport conveyor may be mounted within the reader-printer housing for pushing the value item in a reverse direction by making contact between the push-plate and a substantially central portion of the leading edge of the value item. The printer system may include a plurality of transport conveyors. The printer system may include first and second parallel, spaced-apart transport conveyors, each of the transport conveyors having a push-plate. The parallel, spaced-apart transport conveyors may be mounted within the reader-printer housing such that the push-plates contact the value item at opposing ends of one edge of the value item. The transport conveyor may be operable to, when the gate is open, convey the leading edge of the value item closer to the printer outlet than the frame. The transport conveyor may be operable to, when the gate is open, convey the value item by pushing the trailing edge of the value item by the push-plate so that the leading edge of the value item becomes closer to the printer outlet than the frame.

The printer system may include an edge bracket. The edge bracket may be mounted within the reader-printer housing. The edge bracket may extend vertically adjacent a longitudinal edge of the printing support. The edge bracket may be dimensioned to limit the transverse movement of the value item when the value item is being transported by the transport system. The edge bracket may include a cantilevered section. The edge bracket may be dimensioned to limit the vertical movement of the edge of the value item when the value item is being transported by the transport system. The cantilevered section may include a horizontally disposed subsection and an inclined section. The inclined section may be inclined upwardly toward the printer inlet. The printer system may include a pair of edge brackets disposed at opposing sides of the printing support.

The printer system may include an exit system. The transport system may include the exit system. The exit system may include a ramp defining an exit path toward the printer outlet. The exit path may be inclined. The exit path may be vertically inclined. The exit path may extend horizontally. The exit path may be upwardly inclined. The exit path may be downwardly inclined. The ramp may be rotatably coupled to the remainder of the reader-printer housing. The printer system may include a hinge for hingedly connecting the ramp to the remainder of the reader-printer housing. The ramp may be telescopic. The ramp may have an adjustable length. The ramp may include a ramp cut-out. The ramp may be cut-out at one corner thereof. The ramp may be cut-out along one side edge thereof.

The exit system may include an exit conveyor for conveying the value item along the exit path. The exit conveyor may include an exit conveyor belt. The exit conveyor belt may have an exit push-plate projecting from the conveyor belt. The exit push-plate may be dimensioned for engaging the value item. The exit push-plate may be dimensioned for engaging with one edge of the value item. The exit conveyor may be operable to convey the value item by pushing the value item when the exit push-plate is contacting the value item.

The exit system may include an exit clamp. The exit clamp may be operable to clamp the value item. The exit clamp may be operable to clamp the value item along one side edge thereof. The exit system may be operable to move the exit clamp along the exit path.

The exit system may include the outlet flap. The exit system may include an upper exit guide. The exit system may include an overhang. The exit system may include exit sidewalls. The exit system may include exit rollers. The exit rollers may be dimensioned to contact the value item along side edges of the value item.

The reader-printer apparatus may include a reader-printer display. The reader-printer display may be a liquid-crystal display (LCD). The reader-printer display may be a touch-screen display. The reader-printer apparatus may be operable to connect to an external display. The reader-printer apparatus may include one or more pushbuttons. The pushbuttons may be mounted for actuation thereof from the outside of the reader-printer housing. The reader-printer apparatus may include one or more indicators. The indicators may be indicator lights. The indicators may be mounted to be visible from the outside of the reader-printer housing.

The reader-printer apparatus may include a power management system. The reader-printer apparatus may include a battery. The power management system may include the battery. The battery may be rechargeable. The reader-printer apparatus may include an Uninterruptible Power Supply (UPS). The power management system may include the UPS.

The biometric scanner may be operable to produce an indication of the identity of the user. The reader-printer housing may include a biometric scanner window dimensioned for supporting a finger of the user. The biometric scanner may be operable to scan a finger of the user presented at the biometric scanner window. The biometric scanner may be operable to scan the face of the user when the user's face is directed toward the biometric scanner window. The biometric scanner may be operable to capture an image of the face of the user when the user's face is directed toward the biometric scanner window. The biometric scanner may be operable to scan the eye of the user when the user's eye is directed toward the biometric scanner window. The biometric scanner may be operable to capture an image of the eye of the user when the user's eye is directed toward the biometric scanner window.

The location identification system may be operable to determine whether the current location of the reader-printer apparatus is within a user-defined permitted zone. The location identification system may be operable to produce an indication as to whether the current location of the reader-printer apparatus is within the user-defined permitted zone.

In accordance with another aspect of the invention, there is provided a printer apparatus for printing on value items. The printer apparatus may include the reader-printer housing and the printer system. The reader-printer housing may be dimensioned for enclosing the printer system when the reader system is removed from the reader-printer housing.

In accordance with another aspect of the invention, there is provided a modular system for processing value items. The modular system includes interconnectable modules for performing processing functions. The modular system may include a removably connectable stacking feeder module. The modular system may include the integrated reader-printer apparatus for authenticating and printing on value items. The modular system may include the printer apparatus for printing on value items. The modular system may include a removably connectable curing station. The modular system may include a removably connectable RFID station. The modular system may include a removably connectable quality assurance station. The modular system may include a removably connectable finishing station. The modular system may include a removably connectable reader station. The reader station may include the reader system. The reader station may include an enclosure for enclosing the value item when the value item is being received by the reader system. The reader system may include one or more sources of electromagnetic radiation. The one or more sources may be operable to produce laser radiation. The one or more sources may be operable to produce x-ray radiation. The modular system may include a removably connectable delivery station.

In accordance with another aspect of the invention, there is provided a method of authenticating and printing on a value item. The method involves reading the value item for authentication; receiving the value item for printing; and printing on the value item.

The method may involve identifying a user. Identifying a user may involve detecting the presence of an object at a biometric scanner. Identifying a user may involve scanning the object using the biometric scanner. Identifying a user may involve determining whether a scan of the object matches a stored biometric profile. Identifying a user may involve prompting the user for a passcode. Identifying a user may involve receiving as user input the passcode. Identifying a user may involve determining whether the received passcode is associated with the stored biometric profile.

The method may involve permitting use by the user of an integrated reader-printer. The method may involve permitting use by the user of a printer system. Permitting use by the user of a printer system may involve permitting use by the user of a housed printer system. The method may involve permitting use by the user of a reader station.

The method may involve authenticating the value item. Authenticating the value item may involve sensing the presence of an object at a value item support. Authenticating the value item may involve sensing the presence of an object at a booklet support. Authenticating the value item may involve determining whether the object is a valid type. Determining whether the object is a valid type may involve assigning the object to a valid-type object. Authenticating the value item may involve determining whether the object is a valid type of booklet. Determining whether the object is a valid type of booklet may involve assigning the object to a valid-type booklet. Authenticating the value item may involve reading the valid-type object. Authenticating the value item may involve reading the valid-type booklet. Authenticating the value item may involve reading the value item. Reading the value item may involve capturing an image of the valid-type object. Reading the value item may involve capturing an image of the value item. Reading the value item may involve performing image analysis of the image. Authenticating the value item may involve producing a security signature. Producing a security signature may involve producing a security signature in response to the image. Authenticating the value item may involve determining whether the security signature matches with a stored security signature. Authenticating the value item may involve assigning the valid-type object to an authenticated value item. Authenticating the value item may involve assigning the valid-type booklet to an authenticated value item. Authenticating the value item may involve assigning the valid-type booklet to an authenticated booklet. Authenticating the value item may involve assigning the value item to an authenticated value item.

The method may involve permitting access to a printer. Permitting access to a printer may involve permitting access to a printer system. Permitting access to a printer may involve permitting access to a printer system of an integrated reader-printer apparatus. Permitting access to a printer may involve unlocking an inlet flap. Permitting access to a printer may involve releasing the inlet flap. Permitting access to a printer may involve moving the inlet flap to expose an opening defined by the inlet flap. Permitting access to a printer may involve enabling the printer system. Permitting access to a printer may involve powering up the printer system. Permitting access to a printer may involve moving the printer system to a receiving position.

The method may involve determining a printing area of the value item. Determining a printing area of the value item may involve determining a printing area of the booklet. Determining a printing area of the value item may involve receiving an object through a printer inlet. Receiving an object through a printer inlet may involve sensing the presence of an object proximate a stopper gate of the printer system. Sensing the presence of an object proximate a stopper gate of the printer system may involve receiving an output from a printer sensor of the printer system. Receiving an object through a printer inlet may involve clamping the object at its leading edge. Clamping the object at its leading edge may involve moving a platen vertically. Moving a platen vertically may involve moving the platen upwardly toward an upper frame plate of a transport frame of the printer system. Clamping the object at its leading edge may involve moving a lower clamping plate of a clamping frame vertically. Moving a lower clamping plate of a clamping frame vertically may involve moving the lower clamping plate upwardly toward the upper frame plate. Receiving an object through a printer inlet may involve moving a support plate of the printer system vertically. Moving a support plate of the printer system vertically may involve moving the support plate so as to clamp the object at a non-edge area of the object. Clamping the object at a non-edge area may involve clamping the object between the support plate and a feeding roller. Receiving an object through a printer inlet may involve clamping the object at a non-edge area between the platen and the feeding roller. Receiving an object through a printer inlet may involve moving the object longitudinally to an imaging position of the printer system. Moving the object longitudinally to an imaging position of the printer system may involve moving the platen and the transport frame. Moving the platen and the transport frame may involve moving the platen and the transport frame together longitudinally. Moving the object longitudinally to an imaging position of the printer system may involve moving the clamping frame. Moving the clamping frame may involve moving the clamping frame longitudinally along a rail. Moving the clamping frame may involve moving the clamping frame longitudinally along a rack. Determining a printing area of the value item may involve displaying an image of the object. Displaying an image of the object may involve capturing an image of the object. Capturing an image of the object may involve capturing the image by an imaging device of the printer system. Determining a printing area of the value item may involve determining whether the object is suitable for printing. Determining whether the object is suitable for printing may involve determining whether the image matches with the authenticated value item. Determining whether the object is suitable for printing may involve performing image analysis of the image. Determining whether the object is suitable for printing may involve receiving user input. Determining a printing area of the value item may involve ejecting the object. Determining a printing area of the value item may involve receiving as user input a printing area. Determining a printing area of the value item may involve performing image analysis of the image.

The method may involve printing on the authenticated value item within the printing area. Printing on the authenticated value item within the printing area may involve printing on the authenticated booklet. Printing on the authenticated value item within the printing area may involve causing a printhead of the printer system to move transversely along a printhead guide of the printer system. Printing on the authenticated value item within the printing area may involve transporting the authenticated value item. Transporting the authenticated value item may involve transporting the authenticated value item longitudinally. Transporting the authenticated value item may involve pulling the authenticated value item at its leading edge. Transporting the authenticated value item may involve moving a platen and a transport frame of the printer system. Moving a platen and a transport frame of the printer system may involve moving the platen and the transport frame longitudinally toward the printer outlet. Moving a platen and a transport frame of the printer system may involve moving the platen and the transport frame along a toothed rail. Transporting the authenticated value item may involve moving a clamping frame of the printer system. Moving a clamping frame of the printer system may involve moving the clamping frame longitudinally toward the printer outlet. Moving a clamping frame of the printer system may involve moving the clamping frame along a rack by driving a pinion gear engaged with the rack. Printing on the authenticated value item within the printing area may involve assigning the authenticated value item to a printed value item. Printing on the authenticated value item within the printing area may involve assigning the authenticated value item to a printed booklet.

The method may involve releasing the authenticated value item. Releasing the authenticated value item may involve releasing the printed value item. Releasing the authenticated value item may involve releasing the printed booklet. Releasing the authenticated value item may involve setting the printer system to a printed position of the printer system. Setting the printer system to a printed position of the printer system may involve transporting the printed value item. Releasing the authenticated value item may involve unclamping the printed value item. Unclamping the printed value item may involve unclamping the printed booklet. Unclamping the printed value item may involve moving the platen vertically. Moving the platen vertically may involve lowering the platen. Unclamping the printed value item may involve moving the lower clamping plate vertically. Moving the lower clamping plate vertically may involve lowering the lower clamping plate. Unclamping the printed value item may involve moving the printing support vertically. Moving the printing support vertically may involve lowering the printing support. Releasing the authenticated value item may involve de-activating the stopper. De-activating the stopper may involve rotating the stopper. De-activating the stopper may involve lowering the stopper. Lowering the stopper may involve rotating the stopper about a stopper hinge located at a lower end of the stopper. De-activating the stopper may involve raising the stopper. Raising the stopper may involve rotating the stopper about a stopper hinge located at an upper end of the stopper. Releasing the authenticated value item may involve opening the gate. Opening the gate may involve rotating the gate. Opening the gate may involve lowering the gate. Lowering the gate may involve rotating the gate about a gate hinge located at a lower end of the gate. Opening the gate may involve raising the gate. Raising the gate may involve rotating the gate about a gate hinge located at an upper end of the gate. Releasing the authenticated value item may involve moving the printed value item longitudinally by a conveyor push-plate. Releasing the authenticated value item may involve moving the printed booklet longitudinally by a conveyor push-plate. Releasing the authenticated value item may involve setting the printer system to a printed position. Setting the printer system to a printed position may involve moving the printed value item longitudinally by the conveyor push-plate. Moving the printed value item longitudinally by the conveyor push-plate may involve pushing the printed value item by making contact between the conveyor push-plate and the printed value item at its trailing edge. Releasing the authenticated value item may involve moving the printed value item toward the printer outlet. Releasing the authenticated value item may involve moving the printed booklet toward the printer outlet. Releasing the authenticated value item may involve setting the printer system to the exit position of the printer system. Setting the printer system to the exit position may involve ejecting the printed value item from the transport system. Ejecting the printed value item from the transport system may involve partly ejecting the printed value item from the transport system. Moving the printed value item toward the printer outlet may involve conveying the printed value item by an exit conveyor. Conveying the printed value item by an exit conveyor may involve pushing the printed value item by an exit conveyor push-plate. Pushing the printed value item by an exit conveyor push-plate may involve making contact between the exit conveyor push-plate and the printed value item at its trailing edge. Moving the printed value item toward the printer outlet may involve clamping the printed value item by an exit clamp. Clamping the printed value item by an exit clamp may involve clamping the printed value item at a side edge of the printed value item. Moving the printed value item toward the printer outlet may involve moving the exit clamp longitudinally along an exit ramp. Moving the printed value item toward the printer outlet may involve unlocking an outlet flap. Moving the printed value item toward the printer outlet may involve moving an outlet flap. Moving the outlet flap may involve opening the outlet flap. Moving the printed value item toward the printer outlet may involve locking the outlet flap. Locking the outlet flap may involve locking the outlet flap after moving the printed value item past the printer outlet. Locking the outlet flap may involve receiving an indication that the printed value item is beyond the printer outlet. Releasing the authenticated value item may involve returning the printer system to its receiving position. Returning the printer system to its receiving position may involve moving the platen and the transport frame longitudinally toward the printer inlet. Returning the printer system to its receiving position may involve moving the clamping frame longitudinally toward the printer inlet. Returning the printer system to its receiving position may involve returning the transport frame to its unclamped position. Returning the printer system to its receiving position may involve returning the clamping frame to its unclamped position. Returning the printer system to its receiving position may involve activating the stopper. Returning the printer system to its receiving position may involve closing the gate. Returning the printer system to its receiving position may involve moving the transport conveyor. Returning the printer system to its receiving position may involve moving a plurality of conveyors. Moving a plurality of conveyors may involve moving a pair of parallel, spaced-apart conveyors. Returning the printer system to its receiving position may involve moving the exit conveyor. Returning the printer system to its receiving position may involve unclamping the exit clamp. Returning the printer system to its receiving position may involve moving the exit clamp to its initial position. Returning the printer system to its receiving position may involve closing the outlet flap. Returning the printer system to its receiving position may involve locking the outlet flap. Returning the printer system to its receiving position may involve closing the inlet flap. Returning the printer system to its receiving position may involve locking the inlet flap. Returning the printer system to its receiving position may involve unlocking the inlet flap.

The method may involve recording a log of actions performed by the reader system. The method may involve recording a log of actions performed by the printer system. The method may involve recording a log of actions performed by the integrated reader-printer apparatus.

In accordance with another aspect of the invention, there is provided a method of authenticating a value item. The method involves receiving the value item, and authenticating the value item. Authenticating the value item may include producing laser radiation. Authenticating the value item may include producing x-ray radiation.

In accordance with another aspect of the invention, there is provided a method of printing on a value item. The method involves receiving the value item, transporting the value item, and printing on the value item. Receiving the value item may involve receiving the value item from an automated feeder. Transporting the value item may involve clamping the value item at its leading edge. Clamping the value item at its leading edge may involve clamping by a frame. Transporting the value item may involve pulling the value item by its leading edge. Pulling the value item by its leading edge may involve longitudinally moving the frame when clamping the value item. Transporting the value item may involve pushing the value item by its trailing edge. Pushing the value item by its trailing edge may involve pushing the value item by a push-plate projecting from a conveyor belt.

In accordance with an aspect of the invention, the security checkpoint may include the biometric scanning system. The fingerprint scanner may include the biometric scanning system. The palm-print scanner may include the biometric scanning system. The security checkpoint may include the reader-printer display. The display may include the reader-printer display. The security checkpoint may include the reader system. The document scanner may include the reader system. The security checkpoint may include the power management system. The security checkpoint may include the reader-printer processor. The controller may include the reader-printer processor. The processor may include the reader-printer processor. The security checkpoint may include the reader-printer memory. The memory may include the reader-printer memory. The security checkpoint may include the communications system. The communications controller may include the communications system. The security checkpoint may include the location identification system. The security checkpoint may include the printer system. The printer may include the printer system. The security checkpoint may include the transport system. The security checkpoint may include the modular system. The security checkpoint may include the stacking feeder module. The security checkpoint may include the reader-printer apparatus. The security checkpoint may include the curing station. The security checkpoint may include the RFID station. The security checkpoint may include the quality assurance station. The security checkpoint may include the finishing station. The security checkpoint may include the reader station. The security checkpoint may include the delivery station.

In accordance with another aspect of the invention, there is provided an integrated reader-printer apparatus for authenticating and printing on a value item. The reader-printer apparatus includes: (a) a reader system for reading and authenticating the value item, the reader system being operable to produce a security signature comprising a digital representation of a material characteristic of a security feature of the value item and operable to determine whether the security signature matches a stored security signature; and (b) a printer system for printing on the value item, the printer system comprising a transport system for transporting the value item, the transport system being operable to clamp the value item along one edge only of the value item when transporting the value item.

The transport system may include a roller for rollably contacting the value item at a distance from the one edge. The transport system may include a transport frame and a platen. The transport frame may include an upper frame plate. The transport system may be operable to clamp the value item between the platen and the upper frame plate. The transport system may be operable to move the transport frame longitudinally relative to the roller. The transport system may include a clamping frame. The clamping frame may include a lower frame plate. The clamping frame may include an upper frame plate. The transport system may be operable to clamp the value item between the lower clamping plate and the upper clamping plate. The transport system may be operable to move the clamping frame longitudinally relative to the roller. The apparatus may include an entrance feeder. The entrance feeder may be hingedly coupled at the transport system. The entrance feeder may include the roller. The apparatus may be operable to raise the entrance feeder so as to inhibit contact between the entrance feeder and the value item. The entrance feeder may include a hinge connection for hingedly coupling the entrance feeder. The entrance feeder may include another roller. The another roller may be parallel and spaced-apart from the roller. The apparatus may include a printer inlet. The apparatus may be operable to sense the presence of the value item at the printer inlet. The entrance feeder may be dimensioned for guiding the value item when the value item is being inserted into the printer system through the printer inlet. The printer system may be operable to release the value item via the printer inlet. The transport system may include a stopper for inhibiting longitudinal movement of the value item beyond the stopper. The apparatus may be operable to cause the transport system to clamp the value item when the value item is proximate the stopper. The stopper may include a stopper gate. The stopper gate may be hingedly connected at the transport system. The stopper gate may be operable to permit movement of the value item beyond the stopper. The apparatus may include a transport conveyor. The transport conveyor may include a push-plate. The transport conveyor may be operable to push the value item. The apparatus may include an exit ramp. The apparatus may include at least one of an exit clamp and an exit conveyor. The printer system may include an imaging device for producing an image of the value item when the value item is clamped by the transport system. The apparatus may include a display. The apparatus may be operable to receive as user input a printing area in response to displaying the image on the display. The reader system may be operable to capture a reader-system image of the value item. The reader system may be operable to produce the security signature in response to the reader-system image. The apparatus may include a biometric scanner.

In accordance with another aspect of the invention, there is provided a method of authenticating and printing on a value item. The method involves: (a) authenticating the value item by: (i) capturing an image of the value item by an integrated reader-printer; (ii) in response to the image, producing by the reader-printer a security signature comprising a digital representation of a material characteristic of a security feature of the value item; and (iii) determining by the reader-printer whether the security signature matches a stored security signature, and (b) printing on the value item using a printer system of the reader-printer by: (iv) clamping the value item along one edge only of the value item by a transport system of the printer system; and (v) transporting the value item while being clamped during printing.

In accordance with another aspect of the invention, there is provided a security checkpoint. The security checkpoint includes: (a) a one-way mirror for concealingly permitting the automated recordation of data concerning a person at the security checkpoint; (b) recording equipment for recording the data, the recording equipment being concealed by the one-way mirror; (c) an exit which includes at least one of an exit gate and an exit doorway; and (d) an integrated reader-printer for authenticating and printing on a value item, the reader-printer including: (i) a reader system for reading and authenticating the value item to produce an authentication result; and (ii) a printer system for printing on the value item, the printer system including a transport system for transporting the value item, the transport system being operable to clamp the value item along one edge only of the value item when transporting the value item.

The security checkpoint may be operable to unlock the exit if at least the authentication result is accepted by the security checkpoint. The reader-printer may include an imaging device for producing an image of the value item when the value item is received by the reader-printer. The security checkpoint may be operable to collect biometric data. The security checkpoint may be operable to compare the biometric data and the image to produce a biometric data comparison result. The security checkpoint may be operable to unlock the exit if at least the biometric data comparison result is accepted by the security checkpoint. The security checkpoint may be operable to collect user information which includes the image. The security checkpoint may be operable to unlock the exit if at least the user information is accepted by the security checkpoint. The reader-printer may be operable to produce a plurality of the images of the value item. The security checkpoint may be operable to collect user information which includes at least one of the plurality of the images. The security checkpoint may be operable to unlock the exit if at least the biometric data comparison result and the user information are both accepted by the security checkpoint. The security checkpoint may be operable to collect behavioral data and to analyze the behavioral data to produce behavioral analysis results. The security checkpoint being operable to unlock the exit if at least the biometric data comparison result, the user information and the behavioral analysis results are all accepted by the security checkpoint. The security checkpoint may be operable to unlock the exit if at least the biometric data comparison result, the user information, the behavioral analysis results and the authentication result are all accepted by the security checkpoint. The reader system may be operable to produce a security signature comprising a digital representation of a material characteristic of a security feature of the value item and operable to determine whether the security signature matches a stored security signature. The reader-printer may include a printer-system imaging device for producing a printer-system image of the value item when the value item is received by the printer system. The security checkpoint may be operable to receive as user input a printing area in response to displaying the printer-system image. The reader-printer may include a printer inlet and a printer outlet coinciding with the printer inlet.

In accordance with another aspect of the invention, there is provided a method of recording data concerning a person at a security checkpoint. The method involves: (a) concealingly permitting by a one-way mirror of the security checkpoint the automated recordation of data concerning the person; (b) recording the data by recording equipment of the security checkpoint when the recording equipment is being concealed by the one-way mirror; (c) scanning a document by a reader-printer of the security checkpoint so as to produce a security signature comprising a digital representation of a material characteristic of a security feature of the document; (d) printing on the document by clamping the document along one edge only of the document by a transport system of the reader-printer and transporting the document while being clamped during printing; and (e) unlocking at least one of an exit gate and an exit doorway of the security checkpoint if at least the data and the security signature are both accepted by the security checkpoint.

In accordance with another aspect of the invention, there is provided an apparatus for reading and printing on an object. The apparatus includes: (a) a reader system for reading the object to obtain a digital signature representing a unique feature of the object; and (b) a printer system for printing on the object if the digital signature matches a reference digital signature associated with the object.

The apparatus may include a processor for receiving the digital signature. The apparatus may include a processor for sending a signal to the printer system, if the digital signature matches the reference digital signature, to cause the printer system to print on the object. The apparatus may include a processor for both receiving the digital signature and sending a signal to the printer system, if the digital signature matches the reference digital signature, to cause the printer system to print on the object. The processor may be operable to control operations of the reader system. The processor may be operable to control operations of the printer system. The digital signature may include at least a digital representation of a material characteristic associated with the object. The material characteristic may be a characteristic of a feature of the substrate of the object. The feature may include a security feature of the substrate. The feature may be a security feature of the substrate. The reference digital signature may include a previously stored digital signature. The reference digital signature may be a previously stored digital signature. The digital signature may be a security signature. The reference digital signature may be a security signature. Both the digital signature and the reference digital signature may each be a security signature. The reader system may be operable to capture a reader-system image of the object. The apparatus may be operable to generate the digital signature in response to the reader-system image. The apparatus may be operable to obtain the digital signature by extracting the digital signature. The apparatus may be operable to obtain the digital signature by receiving a transmission containing the digital signature. The reader system may be operable to generate the digital signature. The reader system may be operable to extract the digital signature. The reader system may be operable to receive the digital signature. The printer system may include a transport system for transporting the object. An apparatus for printing on an object includes a transport system for transporting the object. The transport system may be operable to clamp the object. The transport system may be operable to clamp the object along one edge only of the object. The transport system may be operable to clamp the object along one edge only of the object when transporting the object. The transport system may include a roller for contacting the object at a distance from the one edge. The transport system may include a transport frame and a platen. The transport frame may include an upper frame plate. The transport system may be operable to clamp the object between the platen and the upper frame plate. The transport system may be operable to move the transport frame longitudinally relative to the roller. The apparatus may include an entrance feeder hingedly coupled at the transport system. The entrance feeder may include the roller. The apparatus may be operable to raise the entrance feeder so as to inhibit contact between the entrance feeder and the object. The entrance feeder may include a hinge connection for hingedly coupling the entrance feeder. The entrance feeder may include another roller parallel and spaced-apart from the roller. The apparatus may include a printer inlet. The apparatus may be operable to sense the presence of the object at the printer inlet. The entrance feeder may be dimensioned for guiding the object when the object is being inserted into the printer system through the printer inlet. The printer system may be operable to release the object via the printer inlet. The printer system may be operable to eject the object via the printer inlet. The transport system may include a stopper for inhibiting longitudinal movement of the object beyond the stopper. The apparatus may be operable to cause the transport system to clamp the object when the object is proximate the stopper. The apparatus may include an imaging device for producing a printable-area image of the object when the object is clamped by the transport system. The apparatus may include a display. The apparatus may be operable to receive as user input a printing area in response to displaying the printable-area image on the display. The apparatus may include a biometric scanner. The object may be a planar object. The object may be a value item. The object may be a document.

In accordance with another aspect of the invention, there is provided a method of reading and printing on an object. The method involves: (a) reading the object by a reader system of a reader-printer; (b) obtaining by the reader-printer a digital signature representing a unique feature of the object; and (c) printing on the object by a printer system of the reader-printer if the digital signature matches a reference digital signature associated with the object.

In accordance with another aspect of the invention, there is provided an apparatus for verifying whether a user of an object is an authorized user of the object. The apparatus includes: (a) a biometric device for detecting a biometric feature of the user and generating data representing the biometric feature; and (b) a reader-printer for reading and printing on the object, the reader-printer including: (i) a reader system for reading the object to obtain a digital representation of biometric information associated with the authorized user; and (ii) a printer system for printing on the object; and wherein the apparatus is operable to cause the printer system to print on the object if the data matches the digital representation.

The biometric device for detecting a biometric feature of the user and generating data representing the biometric feature may include one or more in any combination of: camera, video camera, IR camera, thermographic camera, UV camera, stereoscopic camera, audio recorder, facial detector, iris detector, fingerprint detector, palm-print detector, motion detector, proximity detector, thermal detector, thermal sensor, tactile sensor, vibration sensor, source of electromagnetic radiation, heat source, ultrasonic transducer, ultrasonic transceiver, metal detector, other biometric device, and other related equipment. The apparatus may include at least one processor for determining whether the data matches the digital representation. The apparatus may include at least one processor for causing the printer system to print on the object if the data matches the digital representation. The apparatus may include at least one processor for both determining whether the data matches the digital representation and causing the printer system to print on the object if the data matches the digital representation. The reader system may be operable to read the object to obtain a digital signature representing a unique feature of the object. The apparatus may be operable to cause the printer system to print on the object only if the digital signature matches a reference digital signature associated with the object. The digital signature may include at least a digital representation of a material characteristic associated with the object. The material characteristic may be a characteristic of a feature of the substrate of the object. The feature may include a security feature of the substrate. The reference digital signature may include a previously stored digital signature. The digital signature may be a security signature. The reference digital signature may be a security signature. Both the digital signature and the reference digital signature may each be a security signature. The reader system may be operable to capture a reader-system image of the object. The apparatus may be operable to generate the digital signature in response to the reader-system image. The reader system may be operable to generate the digital signature. The apparatus may include an exit. The exit may include at least one of an exit gate and an exit doorway. The apparatus may be operable to unlock the exit if the apparatus verifies that the user is the authorized user. The apparatus may be operable to unlock the exit if the data matches the digital representation. The apparatus may be operable to unlock the exit if the digital signature matches the reference digital signature. The apparatus may be operable to unlock the exit if the data matches the digital representation and the digital signature matches the reference digital signature. The reader-printer may include an imaging device for producing an image of the object when the object is received by the reader-printer. The reader system may be operable to generate the digital representation comprising the image. The apparatus may be operable to collect user information which includes the image. The apparatus may include a one-way mirror. The one-way mirror may be operable to conceal from the user's view the biometric device for detecting the biometric features. The printer system may include a transport system for transporting the object. The transport system may be operable to clamp the object along one edge only of the object when transporting the object. The transport system may include an entrance feeder hingedly coupled at the transport system. The entrance feeder may include a roller for contacting the object at a distance from the one edge. The reader-printer may be operable to raise the entrance feeder so as to inhibit contact between the entrance feeder and the object. The transport system may include a platen and a transport frame having an upper frame plate. The transport system may be operable to clamp the object between the platen and the upper frame plate. The transport system may be operable to move the transport frame longitudinally relative to the entrance feeder. The transport system may include a stopper for inhibiting longitudinal movement of the object beyond the stopper. The reader-printer may be operable to cause the transport system to clamp the object when the object is proximate the stopper. The printer system may include a printer-system imaging device for producing a printable-area image of the object when the object is clamped by the transport system. The apparatus may include a display. The apparatus may be operable to receive as user input a printing area in response to displaying the printable-area image on the display. The object may be a planar object. The object may be a value item. The object may be a document.

In accordance with another aspect of the invention, there is provided a method for verifying whether a user of an object is an authorized user of the object. The method involves: (a) detecting by an apparatus a biometric feature of the user; (b) generating data representing the biometric feature; (c) reading the object by a reader system of the apparatus so as to obtain a digital representation of biometric information associated with the authorized user; (d) determining whether the data matches the digital representation; and (e) printing by a printer system of the apparatus on the object if the data matches the digital representation.

In accordance with any one or more aspects of the invention, the security signature may be a sequence of numerical values representing one or more material characteristics associated with the document, value item or other object. Each material characteristic may be a characteristic of a feature of the substrate of the object. The characteristic may be any one or more in any combination of: size, location, embedded depth, shade and color of the feature. The feature may include a security feature of the substrate of the object. The feature may be a security feature of the substrate of the object. The substrate of a document, value item or other object may be made out of any suitable material, including any one or more in any combination of: paper, wood, metal, cloth, glass, fiberglass, plastic, rubber, and other solid material which can be painted, printed on, dyed, etc. The security feature may be any one or more in any combination of: ink of any colour, including fluorescent ink, non-fluorescing ink and iridescent ink; coating; one or more fibers, including fluorescent and non-fluorescing fibers, metallic fiber and heat-sensitive fiber; one or more planchettes; and one or more magnetic particles. The security feature may be inherent to the substrate, such as in the case of natural imperfections occurring incidentally as a result of manufacturing or otherwise processing the substrate, or be deliberately introduced to the substrate. The security feature may be applied to the substrate before, during or after manufacturing the substrate. The security feature may be blended into a raw material from which the substrate is subsequently made. The security feature may be applied to the outer surface of the substrate. The security feature may be embedded at a depth within the substrate. The security feature may be distributed randomly on or within the substrate, such as may inherently result from manufacturing or otherwise processing the substrate. The security feature may be deliberately arranged in a random distribution on or within the substrate.

Other aspects and features of the present invention will become apparent to those of ordinary skill in the art upon review of the following description of embodiments of the invention in conjunction with the accompanying figures and claims.

BRIEF DESCRIPTION OF THE DRAWINGS

In drawings which illustrate by way of example only embodiments of the invention:

FIG. 11 is a perspective view of a portion of the integrated reader-printer of FIG. 7, showing the transport system in accordance with a second reader-printer embodiment of the invention;

FIG. 12 is a perspective view of the transport system of FIG. 11, showing insertion of a booklet;

DETAILED DESCRIPTION

An apparatus for verifying whether a user of an object is an authorized user of the object includes: (a) a biometric detector for detecting a biometric feature of the user and generating data representing the biometric feature; and (b) a reader-printer for reading and printing on the object. The reader-printer may include: (i) a reader system for reading the object to obtain a digital representation of biometric information associated with the authorized user; and (ii) a printer system for printing on the object. The apparatus may operable to cause the printer system to print on the object if the data matches the digital representation. The reader-printer may include: (i) a reader for reading the object to obtain a digital signature representing a unique feature of the object; and (ii) a printer for printing on the object if the digital signature matches a reference digital signature associated with the object.

Figure 1:
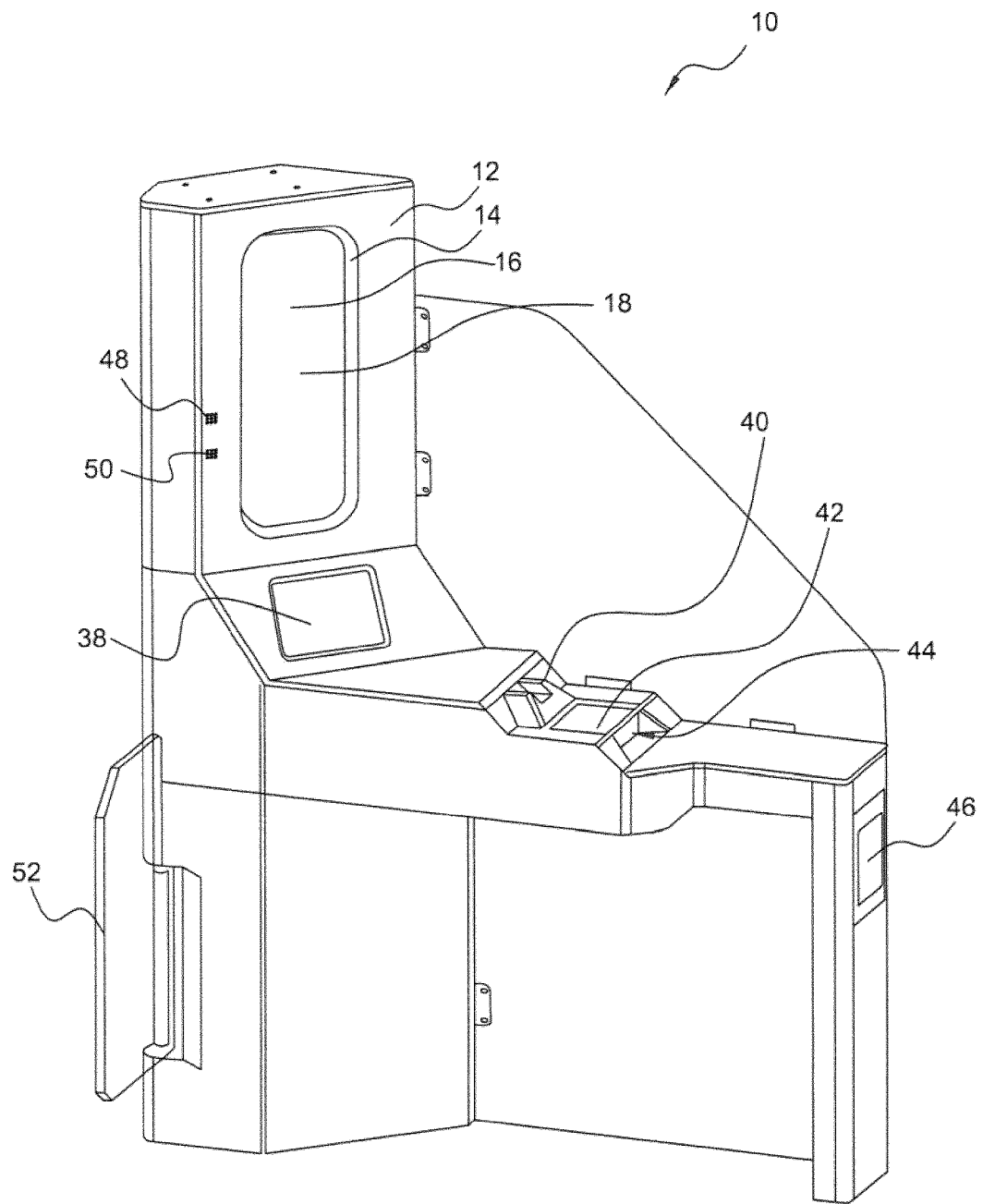
FIG. 1 is a perspective view of a security checkpoint according to a first embodiment of the invention.
Figure 2:
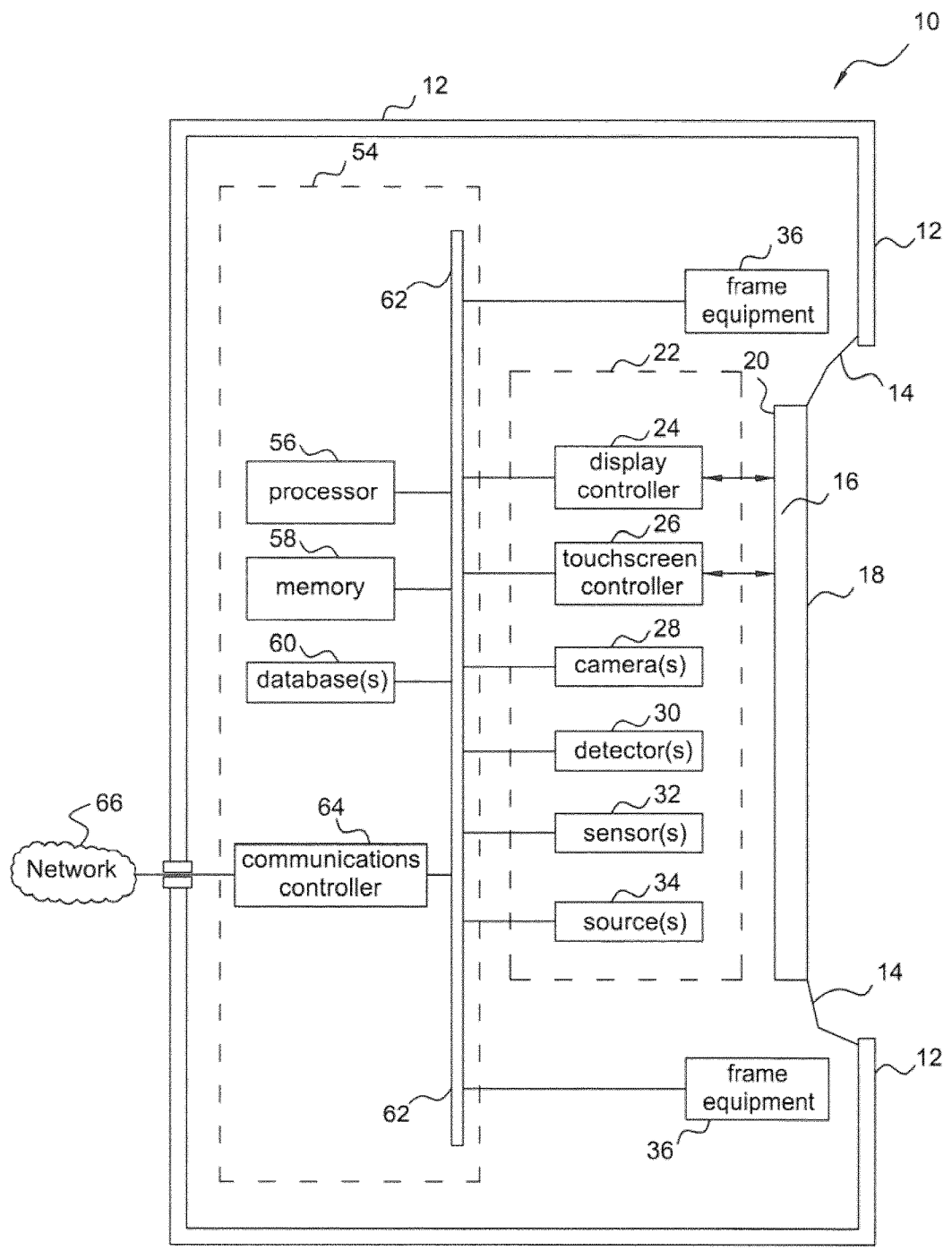
FIG. 2 is a sectional view of the security checkpoint shown in FIG. 1, showing by block diagram equipment inside a housing of the security checkpoint.

Referring to FIGS. 1 and 2, the security checkpoint apparatus according to a first embodiment of the invention is shown generally at 10. The security checkpoint 10 includes a housing 12 that includes a mirror frame 14 for supporting a one-way mirror 16.

The one-way mirror 16 is typically a half-silvered mirror. In general, the one-way mirror 16 can be any object or device that functions to reflect light at its outer side 18 external to the housing 12; and to pass light through the one-way mirror 16 in the direction from its outer side 18 to its inner side 20 inside of the housing 12. Thus, the one-way mirror 16 permits various equipment 22 disposed within the housing 12 behind the one-way mirror 16 to record data about objects and persons (not shown) external to the housing 12 at the security checkpoint 10 without allowing the equipment 22 to be seen from outside the housing 12. A person (not shown) at the security checkpoint 10 standing in front of the one-way mirror 16 would see their own reflection instead of seeing the equipment 22 hidden behind the one-way mirror 16. The use of a one-way mirror 16 advantageously encourages persons at the security checkpoint 10 to reveal their faces to the hidden equipment 22 to the extent that a mirror psychologically attracts the gaze of a person. The use of a one-way mirror 16 also advantageously permits the automated detection of evasiveness to the extent that it is considered unnatural for a person to avoid eye-contact with a reflective mirror, thus attempts to avoid looking at the one-way mirror 16 can be detected by the hidden equipment 22 and recorded for security purposes as an indicator of evasiveness.

In the first embodiment, the security checkpoint 10 is operable to display information on the one-way mirror 16 so that the information is visible to persons present at the security checkpoint 10. As shown in FIG. 2, the hidden equipment 22 includes a display controller 24 for controlling the display of output information on the one-way mirror 16. The information may include instructions to a person at the security checkpoint 10, prompts or questions intended for the person to respond to, and status information, for example. In the first embodiment, the display controller 24 is enclosed within the housing 12. In some embodiments, however, the display controller 24 is not hidden behind the one-way mirror 16.

In the first embodiment, the security checkpoint 10 is operable to receive user input in the form of finger or stylus pressure on the one-way mirror 16. As shown in FIG. 2, the hidden equipment 22 includes a touchscreen controller 26 for receiving touchscreen user input via the one-way mirror 16. By way of example, a person at the security checkpoint 10 may provide a response to a query by selecting a multiple-choice answer presented to the person on the one-way mirror 16. In the first embodiment, the touchscreen controller 26 is enclosed within the housing 12. In some embodiments, however, the touchscreen controller 26 is not hidden behind the one-way mirror 16.

In the first embodiment, the generally reflective view of a person standing in front of the one-way mirror 16 need not be disrupted by the display of information and acceptance of user input by touchscreen technique. In some cases, however, portions of the one-way mirror 16 may be obscured by the use of the one-way mirror 16 for input/output functions.

In the first embodiment, the hidden equipment 22 includes at least one camera 28 for capturing video images of the person at the security checkpoint 10. In some embodiments, multiple cameras 28 at different heights are installed behind the one-way mirror 16 to better capture features, such as the faces, of persons of different heights. In some embodiments, multiple cameras 28 oriented at different angles are installed behind the one-way mirror 16 to better capture features of persons at the security checkpoint 10. Additionally or alternatively, one or more cameras 28 may be installed at other concealed and/or unconcealed locations of the security checkpoint 10 for capturing images at a variety of positions and locations within and/or around the security checkpoint 10.

One or more of the cameras 28 may include filtering or otherwise be particularly suitable for capturing images and/or video within particular regions of the electromagnetic spectrum. For example, one or more of the cameras 28 may be a thermal or IR (infrared) camera 28 suitable for detecting and imaging electromagnetic radiation in the IR (infrared) region of the electromagnetic spectrum. The IR camera 28 may be used to produce images associated with the black body radiation emitted by the person at the security checkpoint 10. In some embodiments, the IR camera 28 is operable to produce a measurement of the body temperature of the person at the security checkpoint 10 or of particular parts of the person (not shown).

One or more cameras 28 may be an UV (ultraviolet) camera 28 operable to detect and image electromagnetic radiation in the UV (ultraviolet) region of the electromagnetic spectrum. In some embodiments, the camera 28 is a stereoscopic camera operable to capture three-dimensional images such as 3D still-images and/or 3D video information. In the first embodiment, at least one camera 28 is a visible light camera 28 operable to detect and image electromagnetic radiation in the visible light region of the electromagnetic spectrum. In variations, the visible light camera 28 is operable to capture still-images, video information, or both still-images and video information. Additionally, the visible light camera 28 is typically operable to record audio information.

In some embodiments, the hidden equipment 22 includes one or more detectors of electromagnetic radiation, such as the detector(s) 30 shown in FIG. 2. Typically, a detector 30 produces an indication of detected radiation which is not an image, and thus the detector 30 is not a camera 28. Indications produced by the detector 30 may include an electronic signal which may be a digital or analog signal, for example. Various detectors 30 may be operable to detect electromagnetic radiation in wide or narrow ranges of wavelengths of the electromagnetic radiation. For example, the detectors 30 may include one or more IR (infrared) detectors 30 operable to detect electromagnetic radiation in the IR region of the electromagnetic spectrum. The detectors 30 may include one or more visible light detectors 30 operable to detect electromagnetic radiation in the visible light region of the electromagnetic spectrum. The detectors 30 may include one or more UV (ultraviolet) detectors 30 operable to detect electromagnetic radiation in the UV region of the electromagnetic spectrum. The detectors 30 may include one or more proximity detectors operable to detect the presence, including possibly the distance, between the one-way mirror 16 and external objects or persons at the security checkpoint 10. The detectors 30 may include one or more motion detectors operable to detect the motion of external objects or persons at the security checkpoint 10.

The detectors 30 may include one or more magnetic energy detectors operable to detect magnetic energy emanating from outside of the housing 12. The detectors 30 of the hidden equipment 22 may be installed at various positions and locations behind the one-way mirror 16 to suit particular uses of the security checkpoint 10. Additionally or alternatively, one or more detectors 30 may be installed at other concealed and/or unconcealed locations of the security checkpoint 10 for detecting electromagnetic radiation at a variety of positions and locations within and/or around the security checkpoint 10.

In some embodiments, the hidden equipment 22 includes one or more sensors, such as the sensor(s) 32 shown in FIG. 2. Typically, a sensor 32 is disposed at the inner side 20 of the one-way mirror 16 for sensing measurable physical phenomena other than electromagnetic radiation. The sensors 32 may be or may include transducers, and may produce an electronic signal which may be a digital or analog signal. For example, the sensors 32 may include one or more vibration sensors for sensing vibrations of the one-way mirror 16. In some embodiments, the sensors 32 include one or more tactile sensors disposed at the outer side 18 of the one-way mirror 16 for sensing force or pressure applied to the one-way mirror 16 at its outer side 18. In some embodiments, the sensors 32 include one or more thermal sensors for sensing heat, including possibly measuring temperature.

The sensors 32 of the hidden equipment 22 may be installed at various positions and locations behind the one-way mirror 16 to suit particular uses of the security checkpoint 10. Additionally or alternatively, one or more sensors 32 may be installed at other concealed and/or unconcealed locations of the security checkpoint 10 for sensing measurable physical phenomena at a variety of positions and locations within and/or around the security checkpoint 10.

The hidden equipment 22 in the first embodiment includes at least one source of lighting or other electromagnetic radiation, such as the source(s) 34 shown in FIG. 2. For example, one or more IR (infrared) sources 34 of electromagnetic radiation in the IR region of the electromagnetic spectrum may emit IR (infrared) radiation from its concealed location behind the one-way mirror 16 outwardly from the housing 12. Emitting IR radiation by an IR source 34 advantageously permits one or more cameras 28 and/or one or more detectors 30, including possibly one or more IR cameras 28 and/or one or more IR detectors 30, to image and/or detect, respectively, external objects or persons at the security checkpoint 10 under exposure to IR radiation. As a further example, one or more sources 34 may produce visible light, such as for backlighting of the one-way mirror 16. In some embodiments, one or more UV (ultraviolet) sources 34 are operable to produce electromagnetic radiation in the UV region of the electromagnetic spectrum, which advantageously permits one or more cameras 28 and/or one or more detectors 30 to image and/or detect, respectively, external objects or persons at the security checkpoint 10 under exposure to UV (ultraviolet) radiation. By way of example, in some embodiments one or more UV cameras 28 and/or one or more UV detectors 30 image and/or detect, respectively, electromagnetic radiation in the UV region of the electromagnetic spectrum while the UV sources 34 are emitting UV radiation. By way of further example, in some embodiments one or more visible light cameras 28 and/or visible light detectors 30 image and/or detect, respectively, electromagnetic radiation in the visible light region of the electromagnetic spectrum while the UV sources 34 are emitting UV radiation, so as to capture visible light fluorescent reflections from external objects and persons at the security checkpoint 10.

In the first embodiment, one or more sources 34 are implemented as light-emitting diodes (LEDs). Additionally or alternatively, various sources 34 may be implemented as lasers, incandescent lighting, halogen lighting, neon lighting, fluorescent lighting, other implementations of lighting, or any combination thereof for example.

The sources 34 of the hidden equipment 22 may be installed at various positions and locations behind the one-way mirror 16 to suit particular uses of the security checkpoint 10. Additionally or alternatively, one or more sources 34 may be installed at other concealed and/or unconcealed locations of the security checkpoint 10 for providing illumination at a variety of positions and locations within and/or around the security checkpoint 10.

Still referring to FIGS. 1 and 2, the security checkpoint 10 includes frame equipment 36 installed within the housing 12 adjacent or proximate the mirror frame 14. In variations, the frame equipment 36 includes one or more pieces of equipment similar or analogous to the pieces of equipment 22 such as the camera(s) 28, detector(s) 30, sensor(s) 32 and source(s) 34 in any number and combination thereof to suit particular uses of the security checkpoint 10.

In variations, all or various portions of the mirror frame 14 may be made of transparent, translucent or one-way mirror type material, for example to suit various security purposes. By way of example, all or a portion of the mirror frame 14 may be made of a transparent material permitting at minimal energy loss the outward transmission of electromagnetic radiation, such as visible light, from one or more sources 34 disposed proximate to the mirror frame 14. For example, different colored LED lighting may be employed to indicate status conditions, such as solid red lighting around the perimeter of the one-way mirror 16 when a person is not permitted to advance toward the one-way mirror 16, solid or flashing green lighting around the one-way mirror 16 perimeter when a person is being requested to advance toward the one-way mirror 16, solid or flashing blue lighting when the person has successfully completed a process at the security checkpoint 10, and flashing red lighting when a process has failed or a person is being flagged for further intervention by security officials. Other color coding combinations are possible. For example, in some embodiments only a silent alarm is triggered to security officials and no indication to the person is made that a process has failed or that further intervention by security officials is required.

Additionally or alternatively, non-transparent material may be used for all or portions of the mirror frame 14 to better conceal the frame equipment 36. In the first embodiment, the mirror frame 14 is angled relative to the one-way mirror 16. In variations, the mirror frame 14 may extend at any angle, including multiple angles, and may be curved for example. The mirror frame 14 may include one or more apertures, such as for accommodating flush-mounted or outwardly projecting frame equipment 36.

In some embodiments, the frame equipment 36 includes one or more of an ultrasound detector, an ultrasound transducer, an ultrasonic transceiver, other sound-based data recordation equipment, and any combination thereof. Each of the ultrasound detector, ultrasound transducer, ultrasonic transceiver or similar may be concealed or unconcealed as suits particular uses of the security checkpoint 10. In some embodiments, ultrasound or ultrasonic frame equipment 36 is flush-mounted at an aperture in the mirror frame 14.

In some embodiments, the frame equipment 36 includes a proximity detector 30 for detecting the presence of an external object or person at the security checkpoint 10. In some embodiments, the proximity detector 30 is operable to provide an indication of the distance between the proximity detector 30 and the sensed object or person. The proximity detector 30 may be flush-mounted at an aperture in the mirror frame 14, for example.

In some embodiments, the frame equipment 36 includes a motion detector 30 for detecting the motion of an external object or person at the security checkpoint 10. The motion detector 30 may be flush-mounted at an aperture in the mirror frame 14, for example.

In some embodiments, various types of sources 34 of the frame equipment 36 are paired with corresponding cameras 28, detectors 30 and/or sensors 32 of the frame equipment 36 to provide imaging, detecting and/or sensing, respectively, of reflected electromagnetic radiation. For example, a source 34 disposed proximate to the mirror frame 14 along one vertical or horizontal side of the one-way mirror 16 may be paired with a corresponding camera 28 and/or detector 30 disposed proximate to the mirror frame 14 along an opposing vertical or horizontal side of the one-way mirror 16. The source 34 and the corresponding camera 28 and/or detector 30, and possibly the mirror frame 14, are angled such that an external object or person at an appropriate location within the security checkpoint 10 will reflect electromagnetic radiation produced by the source 34 toward the corresponding camera 28 and/or detector 30. By such opposing side arrangement, electromagnetic radiation received by the corresponding camera 28 and/or detector 30 is electromagnetic radiation reflected from the external object or person at the security checkpoint 10 under exposure to illumination by the source 34. The pairings of sources 34 and corresponding cameras 28 and/or detectors 30 can be of a variety of types to suit particular uses of the security checkpoint 10. For example, an IR source 34 may be paired with an IR camera 28 and/or IR detector 30; an UV source 34 may be paired with an UV camera 28 and/or UV detector 30; an UV source 34 may be paired with a visible light camera 28 and/or visible light detector 30; an ultrasonic transceiver may be paired with a corresponding ultrasonic transceiver and/or ultrasound detector; etc. Multiple arrays of frame equipment 36 pairs may be employed simultaneously or in sequence for data recordation associated with various distances from the one-way mirror 16, for example.

In some embodiments, one or more cameras 28 of the frame equipment 36 are installed inside the housing 12 at the lower section of the mirror frame 14 just below the one-way mirror 16 and directed upwardly and externally, so as to attempt to capture an image of the face of a person who avoids looking directly at the one-way mirror 16 by looking downwardly. Such upwardly directed cameras 28, which may be visible light cameras 28 for example, may be concealed by virtue of their small size, by configuring such cameras 28 to capture images through small-sized apertures in the mirror frame 14, by at least a portion of the mirror frame 14 being made of a semi-opaque material, by at least a portion of the mirror frame 14 being made of a half-silvered glass material, by other ways or elements of concealment, or any combination thereof for example.

The security checkpoint 10 in various embodiments includes various concealed equipment to suit particular uses of the security checkpoint 10 at positions and locations other than behind the one-way mirror 14 and other than near the mirror frame 14. While not visible in FIG. 1, the security checkpoint 10 may include any combination of one or more of the cameras 28, detectors 30, sensors 32 and sources 34 at any position and location of the security checkpoint 10. For example, various cameras 28, proximity detectors 30 and/or motion detectors 30 may be employed to determine the location of each object or person within or near the security checkpoint 10.

The security checkpoint 10 in various embodiments includes various unconcealed equipment at various positions and locations throughout the security checkpoint 10 to suit particular uses of the security checkpoint 10. In the embodiment shown in FIG. 1, the security checkpoint 10 includes a display 38, which can be used in addition or alternatively to the display features of the one-way mirror 16. Typically, the display 38 is a liquid crystal display (LCD). In some embodiments, the display 38 is a touchscreen display providing both user input and output functions. As can be seen in FIG. 1, the position of the display 38 advantageously permits touchscreen user input at a non-vertical angle which may be more comfortable for certain users and purposes. For example, the display 38 may be used for receiving as touchscreen user input the signature of a person at the security checkpoint 10. Additionally or alternatively, a fully horizontal user input device (not shown) may be used for receiving signatures.

In the embodiment shown in FIG. 1, the security checkpoint 10 includes a fingerprint scanner 40. Typically, the fingerprint scanner 40 is operable to scan a finger being received by the fingerprint scanner 40 and to produce an indication of the fingerprint associated with the person at the security checkpoint 10. Additionally or alternatively, an unconcealed palm-print scanner may be employed to scan the entire palm-print of the person. Additionally or alternatively, one or more cameras 28 and/or detectors 30 of the hidden equipment 22 may be employed to image and/or detect, respectively, the fingerprint and/or palm-print of a person placing their finger and/or palm, respectively, against the one-way mirror 16.

In the embodiment shown in FIG. 1, the security checkpoint 10 includes a document scanner 42. Typically, the document scanner 42 is operable to receive a document (not shown) through its input slot 44 and to scan the document to produce recorded data associated with the person at the security checkpoint 10. In variations, the document scanner 42 may be dimensioned to receive and scan a paper document (e.g. ticket, custom clearance form or other travel document, birth certificate), a card which may be a plastic card (e.g. driver's license, identification card, credit or debit card), a booklet (e.g. passport), other document, other value item, or any combination thereof for example. In some embodiments, the security checkpoint 10 includes multiple document scanners 42 dimensioned for different types of documents or other value items. In some embodiments, the input slot 44 also acts as an output slot for ejection and/or removal of the document from the document scanner 42. Additionally or alternatively, one or more cameras 28 and/or detectors 30 of the hidden equipment 22 may be employed to image and/or detect, respectively, a document placed against the one-way mirror 16 by a person at the security checkpoint 10.

In some embodiments, the document scanner 42 includes an integrated printer operable to print on the document after the document has been received by the document scanner 42. The printer may be of any suitable type, including being a stamp printer for printing official stamps. In some embodiments, the security checkpoint 10 includes a printer that is operable to print a certificate of authenticity or other issued document separate from the scanned document being presented by the person, for example.

In embodiments in which the one-way mirror 16 is operable to display information, the display 38 can be replaced by a printer (not shown in FIG. 1) such as a stamp printer, for example.

In the embodiment shown in FIG. 1, the security checkpoint 10 includes an entrance display 46 near the entrance to the main area of the security checkpoint 10. Typically, the entrance display 46 is a LCD. The entrance display 46 may be employed to provide instructions for a person to enter the main area of the security checkpoint and to instruct others not to approach the security checkpoint 10 when someone else is already present in the security checkpoint 10, for example.

In variations, the security checkpoint 10 includes visible lighting, such as LEDs, at or around the perimeter of one or more of the display 38, fingerprint scanner 40, document scanner 42 and entrance display 46. In the first embodiment, various colored LEDs are located proximate to each of the display 38, fingerprint scanner 40, document scanner 42 and entrance display 46, such that a person at the security checkpoint 10 can be guided by the simultaneous or sequential use of colored LEDs. For example, the entrance display 46 may be framed by solid or flashing green lighting when a person is being requested to advance toward the security checkpoint 10. Upon detecting that the person has advanced some distance toward the main area of the security checkpoint 10, the document scanner 42 may become lit up with solid or flashing green lighting while instructions to insert a specified document into the document scanner 42 is displayed. Upon completion of a process at the document scanner 42, the document scanner 42 lighting may then be de-activated and the fingerprint scanner 40 become lit up with solid or flashing green lighting to assist in guiding the person to use the fingerprint scanner 40. It will be appreciated that by sequential, color-coded lighting a person may be guided through the complete security checkpoint 10 process (described further herein below). Additionally or alternatively, lighting can be employed at other positions and locations of the security checkpoint 10, such as overhead for general lighting and/or along a floor of the security checkpoint 10 to guide a person's footsteps as the person advances toward and/or through the security checkpoint 10.

In the embodiment shown in FIG. 1, the security checkpoint 10 includes a speaker 48 for producing audio, such as voice commands, instructions and/or requests. In the embodiment shown in FIG. 1, the security checkpoint 10 also includes a microphone 50 for receiving audio, such as speech or other sounds made by a person at the security checkpoint 10. In the first embodiment, the security checkpoint 10 is operable to record audio received by the microphone 50.

Still referring to FIG. 1, the security checkpoint 10 includes an exit gate 52 for denying or granting access to exit the security checkpoint 10. Typically, the exit gate 52 is operated automatically upon completion of the security checkpoint 10 process (described further herein below).

In some embodiments, the one-way mirror 16 is full length (not shown in FIG. 1) and extends from adjacent or near the floor of the security checkpoint 10 to a height that it at least slightly greater than the tallest expected height of a typical person (not shown). A full length one-way mirror 16 advantageously permits measurements and other data recordation along the full height of the person, for example. In embodiments where the one-way mirror 16 is full length, unconcealed peripherals such as a printer and/or a secondary display, for example, can be positioned at a suitable height beside the full length one-way mirror 16 (not shown).

Referring to FIG. 2, the security checkpoint 10 in the first embodiment includes a controller 54 having a processing circuit, such as the processor 56, memory circuitry such as the memory 58, optionally one or more databases 60, a connection bus 62, and optionally a communications controller 64.

The controller 54 may be any computing device such as a general purpose computer, microcomputer, minicomputer, mainframe computer, distributed network for computing, functionally equivalent discrete hardware components, etc. and any combination thereof, for example.

As shown in FIG. 2, the connection bus 62 facilitates connections between the controller 54 and the hidden equipment 22 and frame equipment 36. While not shown in the Figures, in at least some embodiments other cameras 28, detectors 30, sensors 32 and sources 34 of the security checkpoint 10, wherever located in or around the security checkpoint 10, are connected to the controller 54 via the connection bus 62.

The processor 56 is typically a processing circuit that includes one or more circuit units, such as a central processing unit (CPU), digital signal processor (DSP), embedded processor, etc., and any combination thereof operating independently or in parallel, including possibly operating redundantly. The processor 56 may be implemented by one or more integrated circuits (IC), including being implemented by a monolithic integrated circuit (MIC), an Application Specific Integrated Circuit (ASIC), a Field Programmable Gate Array (FPGA), etc. or any combination thereof. Additionally or alternatively, the processor 56 may be implemented as a programmable logic controller (PLC), for example. The processor 56 may include circuitry for storing memory, such as digital data, and may comprise the memory 58 or be in wired communication with the memory 58, for example.

The memory 58 in the first embodiment is operable to store digital representations of data or other information, including measurement results and automated analysis results, and to store digital representations of program data or other information, including program code for directing operations of the processor 56.

Typically, the memory 58 and the databases 60 are each all or part of a digital electronic integrated circuit or formed from a plurality of digital electronic integrated circuits. The memory 58 and the databases 60 may be implemented as Read-Only Memory (ROM), Programmable Read-Only Memory (PROM), Erasable Programmable Read-Only Memory (EPROM), Electrically Erasable Programmable Read-Only Memory (EEPROM), flash memory, one or more flash drives, universal serial bus (USB) connected memory units, magnetic storage, optical storage, magneto-optical storage, etc. or any combination thereof, for example. Additionally or alternatively, the memory 58 may be implemented as Random-Access Memory (RAM), variations of RAM such as static RAM (SRAM), Dynamic RAM (DRAM), variations of DRAM such as Synchronous DRAM (SDRAM) and Double Data Rate SDRAM (DDR SDRAM), Video RAM (VRAM), similar or related dynamic memory technologies, or any combination thereof, for example. The memory 58 and the databases 60 may be operable to store digital representations as non-volatile memory, volatile memory, dynamic memory, etc., or any combination thereof.

One or more databases 60 may be implemented as part of the processor 56, the memory 58, and/or as part of the controller 54 (as shown in FIG. 2). Additionally or alternatively, one or more databases 60 may be implemented separately from the controller 54. Each database 60 typically functions to store information, typically in the form of recordable and retrievable data for use by the controller 54, including data records stored in association with other data records.

The controller 54 is typically operable to run any one or more operating systems, including real-time operating systems such as WinCE, Symbian, OSE, Embedded LINUX, non-real time operating systems such as Windows, Mac OS, Unix, Linux, and any combination thereof. The controller 54 may be operable to implement multi-tasking methods involving multiple threads of executable code, for example.

The communications controller 64 facilitates the transmission of data and/or information between the controller 54 and other computing systems via a network 66, which may be the Internet for example. Connection to the network 66 may be implemented by any wired or wireless connection, including a copper wire link, a coaxial cable link, a fiber-optic transmission link, a radio link, a cellular telephone link, a satellite link, a line-of-sight free optical link, and any combination thereof, for example.

Thus, there is provided an apparatus for verifying whether a user of an object is an authorized user of the object, the apparatus comprising: (a) a biometric detector for detecting a biometric feature of the user and generating data representing the biometric feature; and (b) a reader-printer for reading and printing on the object, the reader-printer including: (i) a reader system for reading the object to obtain a digital representation of biometric information associated with the authorized user; and (ii) a printer system for printing on the object; and wherein the apparatus is operable to cause the printer system to print on the object if the data matches the digital representation.

Security Checkpoint Method of Operation

Figure 3:
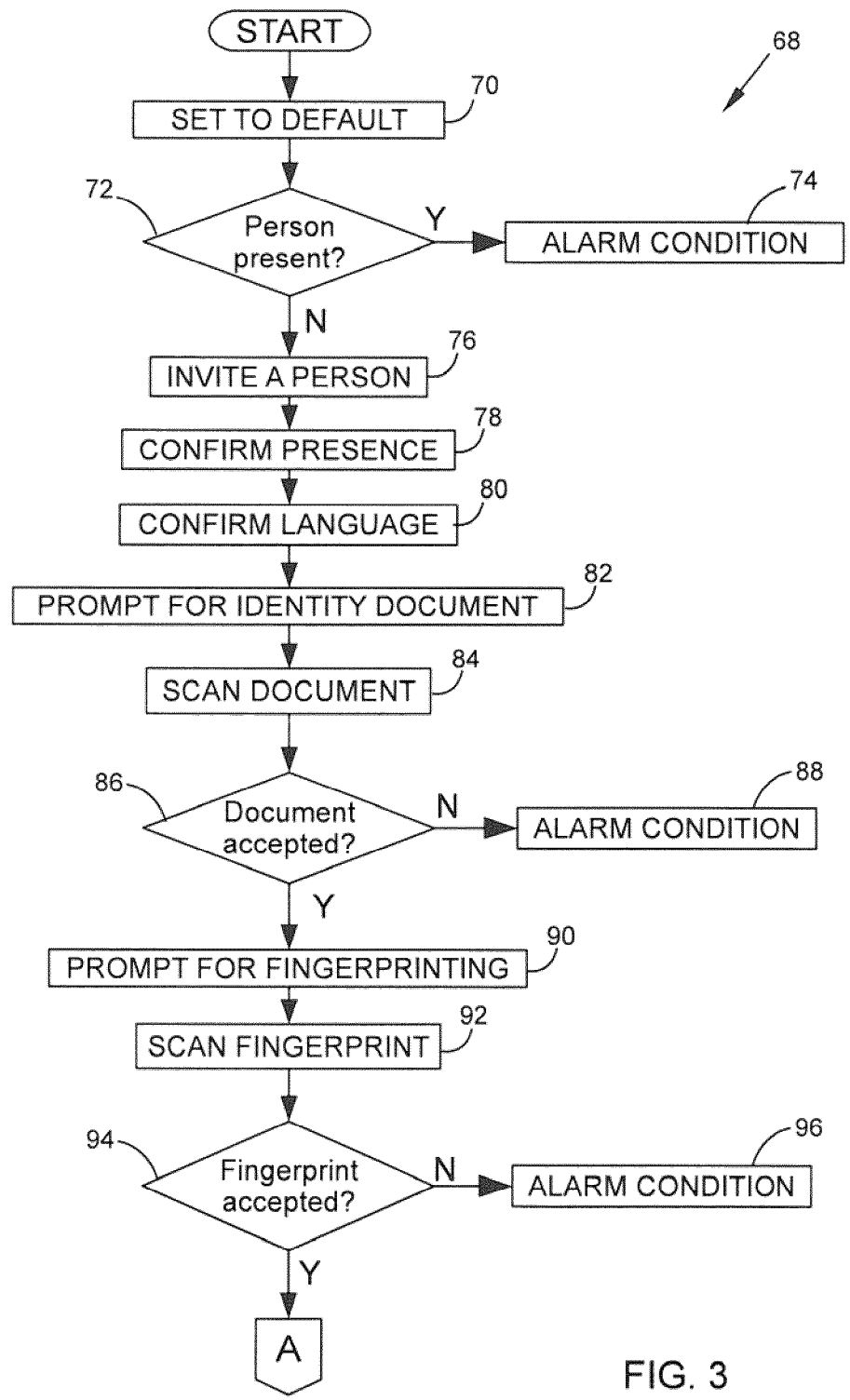
FIG. 3 is a first part of a flow diagram of a method of operation of the security checkpoint shown in FIG. 1.
Figure 4:
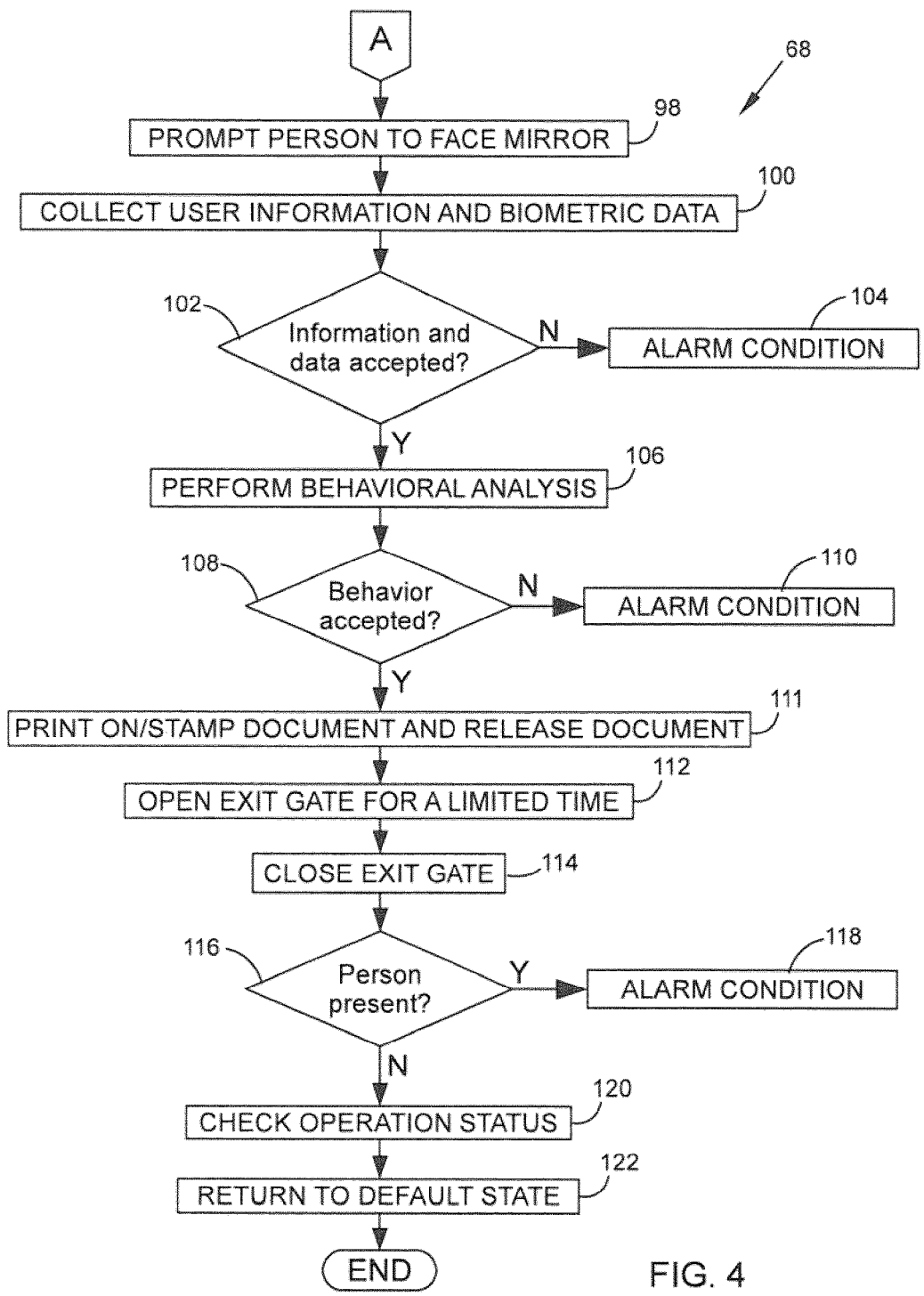
FIG. 4 is a second part of the flow diagram of FIG. 3.

Referring to FIGS. 3 and 4, the memory 58 (FIG. 2) in accordance with the first embodiment of the invention contains blocks of code comprising computer executable instructions for directing the processor 56 (FIG. 2) to perform a method shown generally at 68. Additionally or alternatively, such blocks of code may form part of a computer program product comprising computer executable instructions embodied in a signal bearing medium, which may be a recordable computer readable medium or a signal transmission type medium, for example.

When electrical power is being supplied to the processor 56 and the memory 58, the processor 56 is directed to begin executing the instructions of block 70. Block 70 then directs the processor 56 to set the controller 54 to a default state. Typically, in the default state: 1. the exit gate 52 is locked in its closed position (FIG. 1); 2. general overhead and floor lighting is on, which is typically white; 3. back-lighting of the one-way mirror 16 is off; 4. lighting at the mirror frame 14 is off or neutral (e.g. white); 5. the display 38 is displaying a default image (e.g. a logo or other checkpoint identifying information); 6. lighting at the fingerprint scanner 40 is off or neutral (e.g. white); 7. lighting at the document scanner 42 is off or neutral (e.g. white); and 8. the entrance display 46 is displaying a do-not-enter symbol (e.g. large red cross or red circle with angled red line therethrough).

After block 70 has been executed, the processor 56 is then directed to execute block 72 by which the processor 56 is directed to determine whether any person or unauthorized object (not shown) is present at the security checkpoint 10. An unauthorized object can be any object recognized by the controller 54 as not being part of the security checkpoint 10 itself, for example. The controller 54 causes various cameras 28, detectors 30, sensors 32 and other equipment of the security checkpoint 10 to capture images and other indications of presence, then the processor 56 determines on the basis of the images and other indications whether any person or unauthorized object is present at the security checkpoint 10. In some embodiments, the controller 54 is operable to count the number of persons and unauthorized objects present within the security checkpoint 10.

If by block 72 the processor 56 determines that a person or unauthorized object is present at the security checkpoint 10, then block 74 directs the processor 56 to trigger an alarm condition. Triggering an alarm condition may involve delivering an automated communication to a human-operated security station that human intervention is required. Additionally or alternatively, an alarm condition may result in the automated issuance of a voice command (e.g. instructing a person to exit the security checkpoint 10 or to remain in place), for example. In some embodiments, an alarm condition results in a change in the lighting of the security checkpoint 10, such as by producing red lights indicating an error condition and/or displaying error messages or other instructions on various displays of the security checkpoint 10. In the first embodiment, if an alarm is triggered when the exit gate 52 is unlocked or open, the processor 56 will cause the exit gate 52 to close and lock. Other responses to an alarm condition are possible.

If the processor 56 determines that no person and no unauthorized object is present at the security checkpoint 10, then block 76 directs the processor 56 to invite a person into the security checkpoint 10. Inviting a person into the security checkpoint 10 may involve causing the entrance display 38 to display instructions for the next person to advance toward the security checkpoint 10 and cause lighting around the entrance display 38 to be solid or flashing green, for example.

Block 78 then directs the processor 56 to confirm the presence of a person at the security checkpoint 10, such as by causing the controller 54 to perform actions similar or analogous to those associated with block 72 described herein above.

If the processor 56 is not able to confirm the presence of a person at the security checkpoint 10 after a certain specifiable amount of time, in some embodiments the controller 54 will trigger an alarm condition such as by communicating a request for assistance from human security personnel, for example. In some embodiments, however, the processor 56 will cause the security checkpoint 10 to wait an indefinite amount of time for the next person to enter the security checkpoint 10.

When and if the processor 56 determines that an acceptable number of persons has entered the security checkpoint 10, then block 80 directs the processor 56 to confirm the language selection of the person who entered the security checkpoint 10. Confirming language selection may involve using one or more displays of the security checkpoint 10 and/or audio output to prompt the person to select one of multiple available languages and/or confirm a language selection, including possibly confirming acceptance of a single default language, and receiving audio (e.g. spoken agreement in a language that is recognizable to the controller 54), visual (e.g. nodding), and/or tactile (e.g. touchscreen menu selection) user input related to the person's choice of language. After block 80 has been executed, the processor 56 is directed in the first embodiment to execute block 82.

Block 82 directs the processor 56 to prompt for an identity document, such as an identification card, passport, driver's license, event ticket, credit or debit card, etc. Prompting for an identity document may involve setting lighting at the document scanner 42 to solid or flashing green or other suitable color, displaying on a display of the security checkpoint 52 a prompting display, and/or issuing a voice command via the speaker 48, for example. Prompting for an identity document may also involve, if the processor 56 is not able to confirm the presence of a document being presented at the document scanner 42 after a specifiable amount of time, including possibly after repeatedly prompting for the identity document, triggering an alarm condition. While block 82 relates to an identity document, the present invention contemplates that other types of documents may be requested in addition to or instead of an identity document.

When and if the document has been received by the document scanner 42, block 84 directs the processor 56 to cause the document scanner 42 to scan the received document. Typically, scanning a document involves generating data concerning the document, including possibly data useable to verify and/or authenticate the document, detect fraudulent or counterfeit documents, obtain identification information concerning the owner of the identity document, and other security-related data. In the first embodiment, the security checkpoint 10 is operable to store data produced by the document scanner 42 in the memory 58, database 60 and/or transmit the data via the network 66 to a remote computer (not shown) and/or remote database (not shown), for example.

In some embodiments, the one-way mirror 16 is functional to provide document scanning, such as by having the person place the document against the one-way mirror 16 and by imaging and/or detecting the placed document using one or more cameras 28 and/or detectors 30, respectively. In some embodiments, instructions for placing the document against a specified area of the one-way mirror 16 are displayed on the one-way mirror 16. Additionally or alternatively, audio instructions may be provided for this purpose.

When the document scanning is completed, the processor 56 is directed to execute block 86.

Block 86 directs the processor 56 to determine whether the document scanned by block 84 is accepted by the security checkpoint 10. In the first embodiment, determining whether a document is to be accepted involves comparing data produced by the document scanner 42 with previously stored data. For example, one or more database 60 queries and/or remote database queries can result in the controller 54 receiving or determining by comparison confirmation of authenticity of the scanned document, for example.

If the processor 56 determines that the scanned document is not accepted, then block 88 directs the processor 56 to trigger an alarm condition in a manner similar or analogous to block 74.

If the processor 56 determines that the scanned document is accepted, then the method proceeds to block 90.

Block 90 directs the processor 56 to prompt for fingerprinting of the person who is present at the security checkpoint 10. Prompting the person for fingerprinting may involve de-activating the lighting at the document scanner 42 and activating lighting at the fingerprint scanner 40, displaying at a display of the security checkpoint 10 instructions for using the fingerprint scanner 40, and/or issuing a voice command via the speaker 48, for example. In some embodiments, the processor 56 will trigger an alarm condition if no finger is received by the fingerprint scanner 40 within a specifiable amount of time.

When and if a finger has been received by the fingerprint scanner 40, block 92 directs the processor 56 to cause the fingerprint scanner 42 to scan the received finger. Typically, scanning a finger for its fingerprint involves generating data concerning the fingerprint, including possibly data useable to verify and/or authenticate the fingerprint, detect fraudulent or counterfeit fingerprint patterns, detect fingerprint tampering, and other security related data. In some embodiments, the fingerprint scanner 42 is operable to measure temperature and/or detect the presence of heat generated by living human tissue of a finger, so as to determine whether a fake fingerprint from a non-living material is being presented at the fingerprint scanner 42. In the first embodiment, the security checkpoint 10 is operable to store data produced by the fingerprint scanner 42 in the memory 58, database 60 and/or transmit the data via the network 66 to a remote computer (not shown) and/or remote database (not shown), for example.

In some embodiments, the security checkpoint 10 is operable to provide fingerprint scanning at the one-way mirror 16, such as by having the person place their finger against the one-way mirror 16 (such as at a particular area of the one-way mirror 16 as indicated by a display appearing on the one-way mirror 16 and/or audio instructions outputted by the speaker 48) and by imaging and/or detecting the placed finger using one or more cameras 28 and/or detectors 30, respectively. In such embodiments, the security checkpoint 10 may also be operable to employ a thermal camera 28, IR detector 30 and/or thermal sensor 32 to detect and/or measure heat generated by the finger placed against the one-way mirror 16.

Additionally or alternatively, the processor 56 may be directed to prompt for a palm-print and to cause scanning by a palm-print scanner, which may be the one-way mirror 16, for example. The security checkpoint 10 is also in some embodiments operable to detect and/or measure heat generated by a palm placed at the palm-print scanner (e.g. the one-way mirror 16).

When the fingerprint (or palm-print) scanning is completed, the processor 56 is directed to execute block 94.

Block 94 directs the processor to determine whether the fingerprint scanned by block 92 is accepted by the security checkpoint 10. In the first embodiment, determining whether a fingerprint is to be accepted involves comparing data produced by the fingerprint scanner 42 with previously stored data. For example, one or more database 60 queries and/or remote database queries can result in the controller 54 receiving confirmation of or determining by comparison the authenticity of the scanned fingerprint, for example.

If the processor 56 determines that the scanned fingerprint is not accepted, then block 96 directs the processor 56 to trigger an alarm condition in a manner similar or analogous to block 74.

If the processor 56 determines that the scanned fingerprint is accepted, then the method proceeds to block 98.

Block 98 directs the processor 56 to prompt the person at the security checkpoint 10 to face the one-way mirror 16. Prompting the person to face the one-way mirror 16 may involve de-activating the lighting at the fingerprint scanner 42 and activating lighting at the mirror frame 14, displaying instructions on proper positioning and behavior (e.g. whether smiling or excessive movement is prohibited, etc.), and/or issuing a voice command via the speaker 48, for example. In some embodiments, the processor 56 will trigger an alarm condition if the security checkpoint 10 is unable to confirm proper positioning of the person within a specifiable amount of time.

When and if the person becomes properly positioned for biometric identification, block 100 directs the processor 56 to cause the hidden equipment 22 to collect user information and biometric data.

In the first embodiment, collecting user information involves displaying instructions, questions, multiple choice answer selections, menu selections, user input text boxes, prompting text, prompting graphics and other indicia on the one-way mirror 16 or via the document scanner 42; issuing voice commands or other voice prompts in the person's selected language via the speaker 48; presenting other suitable user-interface output; or any combination thereof for example. Collecting user information further involves receiving as user input touchscreen manipulations; audio information (e.g. voice commands issued by the person); visual user input (e.g. sign language communications captured by video imaging for processing by an automated sign language recognition program and/or by a human interpreter providing interpreted input to the controller 54); other suitable user input; or any combination thereof for example.

In some embodiments, collecting user information includes prompting for and receiving as user input the person's signature via touchscreen user input. The person may write their signature using their finger and/or be given the opportunity to use a stylus to write their signature, for example. The person may be required to provide their signature at a specified area of the touchscreen portion of the one-way mirror 16, for example. In some embodiments, a dedicated touchscreen pad, which is typically oriented horizontally, is provided for obtaining signatures.

In some embodiments, collecting user information includes receiving a payment from the person at the security checkpoint 10. For example, in circumstances where a person wishing to attend an event is permitted to buy an event ticket "at the door", the security checkpoint 10 may be configured to screen potential attendees (e.g. employ automated detection techniques for detecting excessive intoxication or other anti-social behaviors) and to confirm payment prior to granting access to the event. Payment processing may involve the use of dedicated payment processing equipment (not shown) and/or the document scanner 42 dimensioned to receive payment (e.g. cheques and/or wallet-sized cards such as credit or debit cards), for example.

In the first embodiment, collecting biometric data involves imaging and/or detecting facial and/or other bodily features of the person. Typically, collecting biometric data involves generating data concerning biometric features of the person, including possibly data useable to identify and/or verify credentials of the person, detect persons of interest to law enforcement agencies, and other security related data. Biometric data collected by the hidden equipment 22 via the one-way mirror 16 may include, but is not necessarily limited to, any one or more of: visible light images of the face of the person, including images useable for facial recognition and/or images useable to perform gait recognition on a person (that is, to analyse the way in which a person walks); visible light images of the iris or other body parts of the person (including geometrical recognition of the fingers and/or palms and/or ear lobes); images captured while the person is under exposure to IR radiation; images captured while the person is under exposure to UV radiation; temperature and/or heat measurements associated with the person; audio recordings of the voice and/or other sounds produced by the person, including audio recordings useable for voice recognition and voice analysis (e.g. determining the level of anxiety demonstrated by a person on the basis of their voice and speech patterns); other biometric data useable for security purposes, and any combination thereof for example.

Other biometric data may also be collected, such as bone density, vascular patterns and oxygen content of the blood. For example, it is known to use ultrasonic transducers to detect bone density and the amount of oxygen in the blood can be measured using a pulse oximeter. For vascular patterns, near-infrared light can be used to obtain reflected or transmitted images of blood vessels in parts of the body, such as the hands or fingers, typically using a monochrome camera. An example of a suitable monochrome camera is a monochrome charge-coupled device (CCD) array camera however, other types of monochrome camera could also be used. The equipment to collect this biometric data may be behind the one-way mirror or could be located in an alternative part of the checkpoint 10.

In the first embodiment, the security checkpoint 10 is operable to store user information and biometric data produced by the hidden equipment 22 or other equipment of the security checkpoint 10 in the memory 58, database 60 and/or transmit the data via the network 66 to a remote computer (not shown) and/or remote database (not shown), for example.

When the user information and biometric data collection is completed, the processor 56 is directed to execute block 102.

Block 102 directs the processor to determine whether the user information and biometric data collected by executing block 100 is accepted by the security checkpoint 10.

In the first embodiment, determining whether the collected user information is accepted involves analysis of the collected user information. In the first embodiment, analyzing the collected user information involves comparing the collected user information to previously stored information concerning the person. For example, in some embodiments the person is prompted by block 100 to state their name audibly, which is recorded and processed by voice recognition software for automated comparison with text appearing on an identity document which was previously scanned by block 84. Discrepancies between the audibly stated name and the name appearing in the presented identity document may be recorded as an indication of a risk factor associated with that person for the security purposes of the security checkpoint 10.

In the first embodiment, determining whether the collected biometric data is accepted involves analysis of the collected biometric data. In the first embodiment, analyzing the collected biometric data involves comparing the collected biometric data to previously stored data. For example, one or more database 60 queries and/or remote database queries can result in the controller 54 receiving confirmation of and/or determining by comparison the authenticity of the collected biometric data, for example.

While FIGS. 3 and 4 shows the collection of user information and biometric data as occurring at block 100 of the method 68, in general the collection of user information and biometric data may occur at any time and may be continuously or periodically occurring the entire time the person is within measurement range of the security checkpoint 10. For example, hidden and/or unconcealed cameras 28 and/or microphones 50 at various positions and locations throughout the security checkpoint 10 may be employed for continuous monitoring of persons within the vicinity of the security checkpoint 10.

In embodiments where continuous or periodic collection of user information and biometric data is occurring, it may in some circumstances be unnecessary to execute block 98 as sufficient user information and biometric data may already be collected for block 102 to be executed before the need arises to prompt the person to face the one-way mirror 16.

If the processor 56 determines that the collected user information and biometric data is not accepted, then block 104 directs the processor 56 to trigger an alarm condition in a manner similar or analogous to block 74.

If the processor 56 determines that the collected user information and biometric data is accepted, then the method proceeds to block 106.

Block 106 directs the processor 56 to cause the controller 54 to perform behavioral analysis or otherwise obtain results of one or more behavioral analyses. In the first embodiment, the automated behavioral analysis is performed on the basis of behavioral data collected while the person is within the vicinity of the security checkpoint 10, possibly in conjunction with previously stored data associated with the person. Such collection of behavioral data may be ongoing throughout the process the method 68, and may consist entirely of or include data collected by executing blocks 84, 92 and 100 for example. Automated behavioral analysis may involve artificial intelligence, signal processing, vision analysis, facial recognition, voice recognition, speech analysis or other automated processing to detect suspicious or threatening patterns of behavior (e.g. avoidance of eye-contact with the mirror, voice and speech patterns associated with elevated levels of emotions such as anxiety or anger, body positions that suggest concealment of products under clothing, aggressive behavior, etc.). In some embodiments, executing automated behavioral analysis involves comparing data collected about the person's behavior with data previously stored in a database 60 and/or remote database, such as known behavioral templates or known history of the person. In the first embodiment, the automated behavioral analysis results in a quantification of risk factors associated with the person's behavior.

While FIGS. 3 and 4 shows the automated behavioral analysis as occurring at block 106, in general automated behavioral analysis may occur as behavioral data is being collected, including possibly on an ongoing basis whenever the person is at or within the vicinity of the security checkpoint 10.

When the automated behavioral analysis is completed, the processor 56 is directed to execute block 108.

Block 108 directs the processor to determine whether the automated behavioral analysis results obtained by executing block 106 are accepted by the security checkpoint 10. In the first embodiment, determining whether the results are accepted involves comparing the quantification of risk factors associated with the person's behavior to one or more specifiable risk factor threshold values, and may include an algorithmic combination of results obtained by executing blocks 86, 94, 102 and 108 for example.

If the processor 56 determines that the automated behavioral analysis results are not accepted, then block 110 directs the processor 56 to trigger an alarm condition in a manner similar or analogous to block 74.

If the processor 56 determines that the automated behavioral analysis results are accepted, then the method proceeds to block 111.

Block 111 directs the processor 56 to cause the document scanner 42 to print on or stamp the document in accordance with printing and/or stamping functions of the document scanner 42. Block 111 may direct the processor 56 to cause the document scanner 42 to print an official stamp onto a passport booklet, for example. Printing on or stamping the document may involve retrieving data from the memory 58 and/or the database 60, and may involve processing the retrieved data prior to printing information onto the document in accordance with such processed data. Additionally or alternatively, printing on or stamping the document may involve receiving data via the network 66 from a remote computer (not shown) and/or remote database (not shown), for example.

By way of non-limiting example, the document scanner 42 may be employed solely to perform printing and/or stamping functions in some embodiments, such as embodiments in which the one-way mirror 16 is employed to scan documents.

When all printing and/or stamping, if any, has been completed, block 111 further directs the processor 56 to cause the document scanner 42 to release the document. Releasing the document may involve ejecting the document from an exit port of the document scanner 42, for example.

While FIG. 4 shows block 111 being executed after block 108, in general block 111 may be executed at any time after the document has been received by the document scanner 42 and prior to the document being released from the document scanner 42. In some embodiments and circumstances, it is not necessary to execute block 111 at all. When block 111 has been executed or skipped, the method proceeds to block 112.

Block 112 directs the processor 56 to unlock, including possibly opening such as by swinging open or sliding (e.g. horizontally and/or vertically) out of the way, the exit gate 52 for a specifiably limited amount of time. Typically, the amount of time the exit gate 52 is unlocked is determined by the slowest expected exit time of a typical person exiting the security checkpoint 10. In some embodiments, the security checkpoint 10 is operable to monitor the progress of movement of the person as the person exits the security checkpoint 10, and to permit the exit gate 52 to remain unlocked while the person is exiting. In some embodiments, unlocking the exit gate 52 involves producing an indication, such as an output signal, of acceptance by the security checkpoint 10 for subsequent confirmation by a human operator, such as by actuating a button (not shown) for example, prior to the exit gate 52 becoming unlocked. Typically, however, unlocking of the exit gate 52 is fully automated such that the block 112 directs the processor 56 to directly unlock the exit gate without human intervention.

Block 114 then directs the processor 56 to lock the exit gate 52 closed. Locking the exit gate 52 closed involves in some embodiments automatedly closing the exit gate 52 such as by swinging or sliding the exit gate 52 closed.

Block 116 then directs the processor 56 to determine whether any person or unauthorized object is present at or within the security checkpoint 10, in a manner similar or analogous to the execution of block 72 described herein above.

If the processor 56 determines that a person or unauthorized object is present at or within the security checkpoint 10, then block 118 directs the processor 56 to trigger an alarm condition, in a manner similar or analogous to block 74.

If the processor 56 determines that no person and no unauthorized object is present at the security checkpoint 10, then the method proceeds to block 120.

Block 120 directs the processor 56 to cause the controller 54 to check the operating status of the security checkpoint 10. In the first embodiment, the operating status check is a controller 54 housekeeping operation that involves checking controller 54 parameter values to ensure continued reliable operation of the controller 54.

Block 122 then directs the processor 56 to cause the security checkpoint 10 to return to its default state, which is typically identical to that produced by executing block 70 described herein above.

After block 122 has been executed, the processor 56 is directed to return processing to block 72, or end the method 68.

While the method 68 is illustrated and described herein as being performed in a specified sequence, in general various features of the method 68 may be performed in any suitable sequence. For example, block 80 may be executed before block 76 so that the person's language selection is confirmed before the person is invited to enter the security checkpoint 10. Also, various features of the method 68 are optional depending on the particular uses of the security checkpoint 10. For example, in the circumstances of an automated gateway to the entrance of a sports arena or concert hall, fingerprinting may not be necessary and the documents prompted for by the security checkpoint 10 may only be a previously issued event ticket, for example. In circumstances where both fingerprinting (and/or palm-printing) and document scanning are employed, such a method may be performed in different sequential orders depending on the process flow selected for a particular use of the security checkpoint 10. In general, a variety of method features in a variety of sequences are possible.

Thus, there is provided a method for verifying whether a user of an object is an authorized user of the object. The method involves: (a) detecting by an apparatus a biometric feature of the user; (b) generating data representing the biometric feature; (c) reading the object by a reader system of the apparatus so as to obtain a digital representation of biometric information associated with the authorized user; (d) determining whether the data matches the digital representation; and (e) printing by a printer system of the apparatus on the object if the data matches the digital representation.

Second Embodiment of Security Checkpoint

Figure 5:
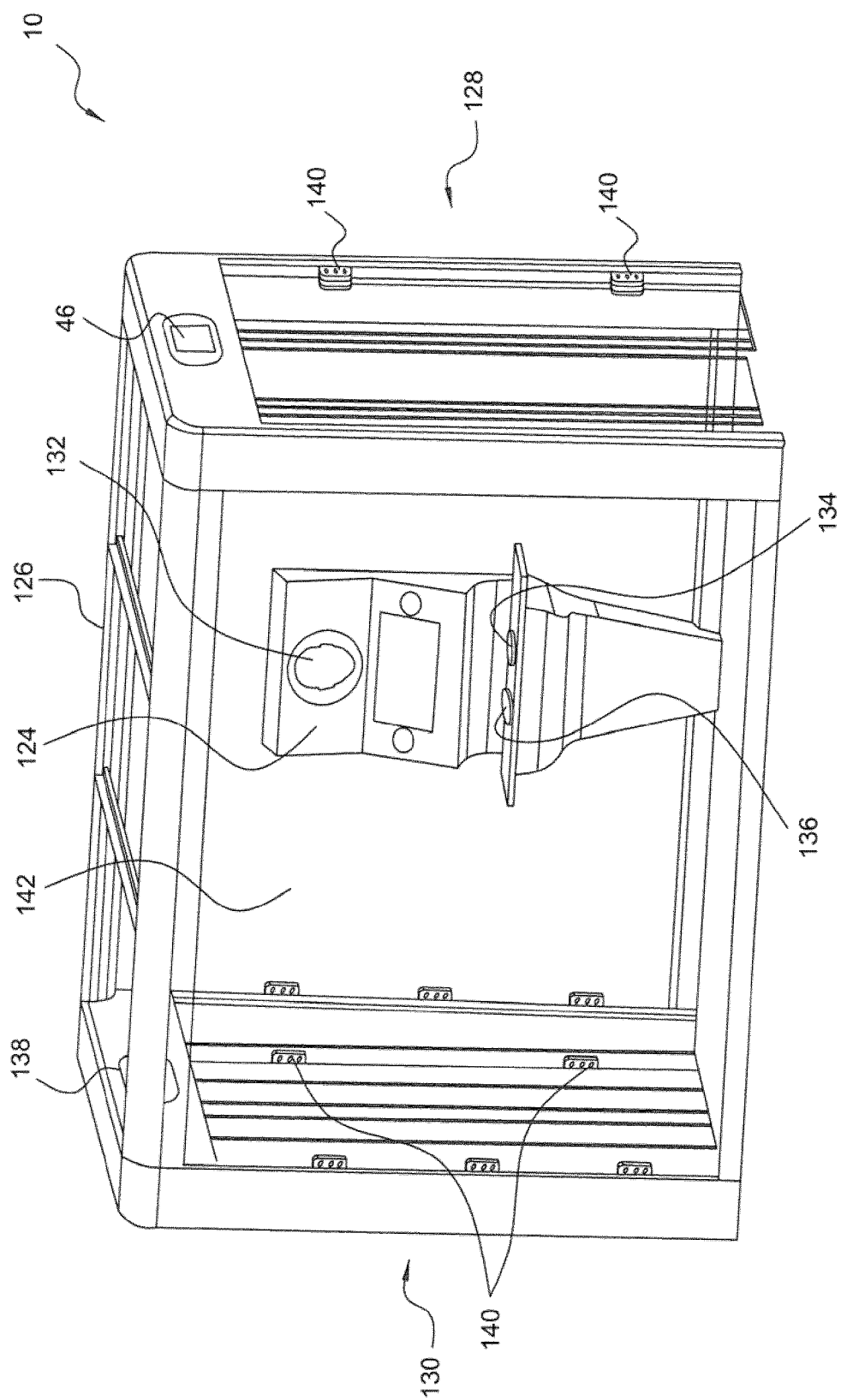
FIG. 5 is a perspective view of the security checkpoint according to a second embodiment of the invention.
Figure 6:
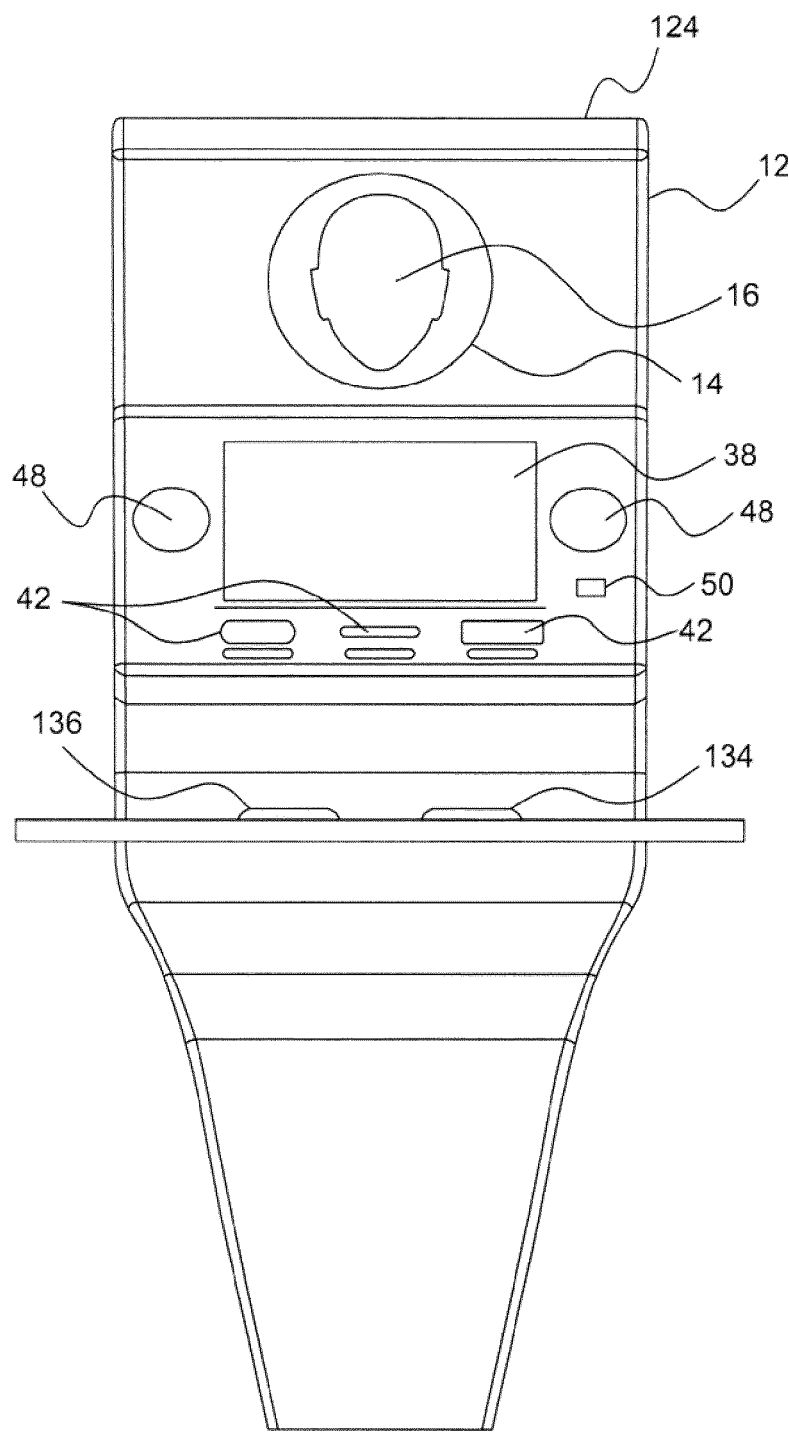
FIG. 6 is a front view of a security console of the security checkpoint shown in FIG. 5, showing a printer.

Referring to FIGS. 5 and 6, in a variation of the first embodiment, the security checkpoint 10 in accordance with a second embodiment of the invention includes a security console 124 disposed within an enclosure 126 having an entrance doorway 128 and an exit doorway 130.

The security console 124 includes a one-way mirror 132, behind which is the hidden equipment 22 (not visible in FIGS. 5 and 6). The one-way mirror 132 is shown in FIGS. 5 and 6 as having a generally circular shape, although any suitable shape may be used including oval, square, polygonal, irregular, other shapes, and any combination thereof for example. In some embodiments, a plurality of one-way mirrors 16 may be used.

Referring to FIG. 6, the security console 124 also includes the display 38, which in the second embodiment is a touchscreen LCD; a pair of speakers 48; and a microphone 50. The security console 124 includes three document scanners 42 dimensioned to accept documents of three different sizes (e.g. driver's license, credit cards, debit cards and other wallet-sized cards, and/or single-sheet documents such as custom clearance forms, birth certificates and event tickets). In variations, any number of differently dimensioned document scanners 42 may be suitably used in various embodiments. The security console 124 of the second embodiment includes a passport reader 134 for reading passport booklets and a printer 136, which in at least some embodiments is a stamp printer 136 for printing official stamps on passport booklets.

Referring back to FIG. 5, in the second embodiment the entrance display 46 is mounted on the enclosure 126 above the entrance doorway 128. The security checkpoint 10 of the second embodiment also includes an exit display 138 mounted on the inside of the enclosure 126 above the exit doorway 130. In the second embodiment, the security checkpoint 10 is operable to coordinate the information displayed on the entrance display 46 and the status of the entrance doorway 128 (e.g. locked or unlocked status) such that a person is permitted to enter the security checkpoint 10 through the entrance doorway 128 when the entrance display 46 is displaying an invitation for a next person to enter the security checkpoint 10. Similarly, the security checkpoint 10 in the second embodiment is operable to coordinate the information displayed on the exit display 138 and the status of the exit doorway 130 such that a person is permitted to exit the security checkpoint 10 through the exit doorway 130 when the exit display 138 is displaying an invitation for the person currently inside the enclosure 126 to exit the security checkpoint 10.

While FIG. 5 shows the entrance doorway 128 and the exit doorway 130 as having hinges 140 to permit the doorways 128 and 130 to open and close by swinging horizontally, other doorway types are possible. For example, in some embodiments the doorways 128 and 130 open and close by swinging vertically. In some embodiments, the doorways 128 and 130 open and close by sliding horizontally and/or vertically. In some embodiments, the doorways 128 and 130 open and close automatically, such as under the control of the controller 54 for example.

While FIGS. 5 and 6 show the one-way mirror 16 disposed at approximately head-height, the one-way mirror 16 may have any suitable size and be installed at any suitable height. For example, the security checkpoint 10 may include a full height one-way mirror 16, which may be adjacent the security console 124 such as being disposed along the side wall 142 of the enclosure 126.

In some embodiments (not shown), the exit doorway 130 may include a one-way mirror 16, including possibly a full length one-way mirror 16, for collecting user information, biometric data, behavioral analysis data, other security data relating to the person at the security checkpoint 10, or any combination thereof for example.

In such embodiments where the exit doorway 130 includes a one-way mirror 16 operable to display information and accept user input, including accepting touchscreen user input, scanning fingerprints and/or palm-prints and scanning documents, one or more functional elements of the security console 124 may not be needed at the security console 124. It is contemplated, however, that printer functions would typically remain at the security console 124 or at a similar wall-mounted or table-mounted printing device. In such embodiments, the exit doorway 130 would preferably be of the automatically-controlled, horizontally-sliding type (including possibly being a split doorway that opens and closes by two half-doors sliding in opposing horizontal directions), but all types of doorways are possible. Also in such embodiments, the entrance doorway 128 is optional as is the extended distance between the entrance doorway 128 and the exit doorway 130.

Reader-Printer Device

Figure 7:
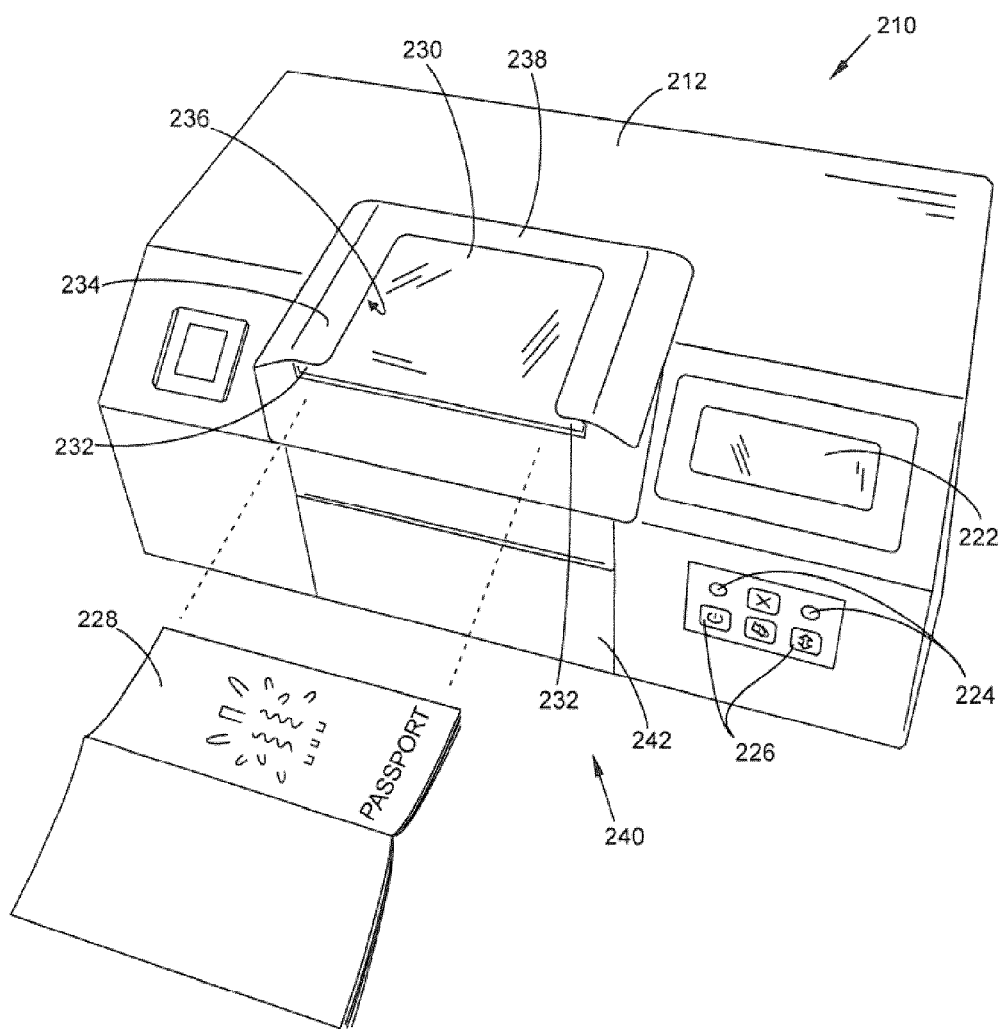
FIG. 7 is a perspective view of an integrated reader-printer according to a first reader-printer embodiment of the invention.
Figure 8:
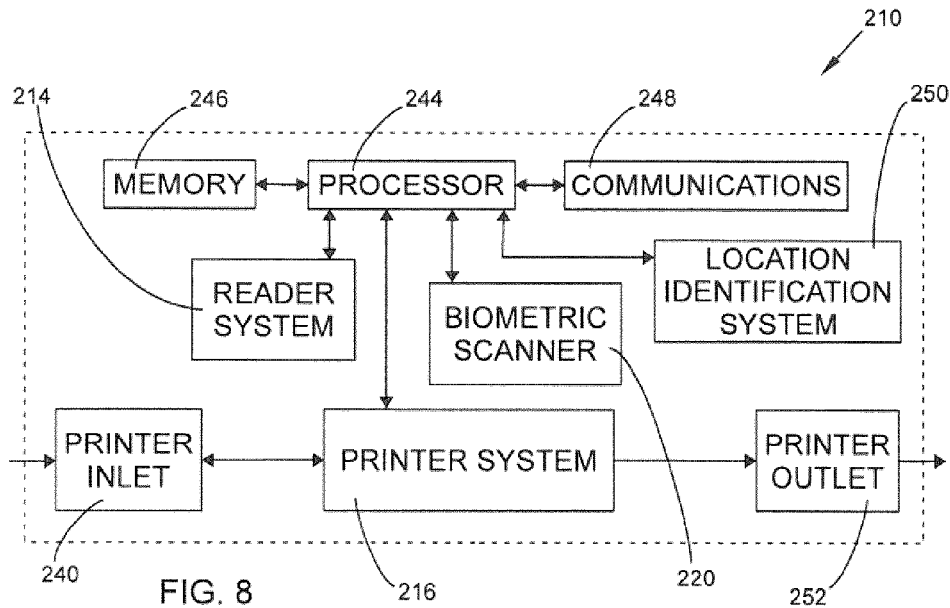
FIG. 8 is a block diagram of system components of the integrated reader-printer of FIG. 7, showing a reader-printer processor and a reader-printer memory.

Referring to FIGS. 7 and 8, a reader-printer device according to a first reader-printer embodiment of the invention is shown generally at 210. The reader-printer 210 is an integrated reader-printer having both reading for authentication, including verification, and printing capabilities. The reader-printer 210 includes a reader-printer housing 212 for housing various components of a reader system 214 and a printer system 216 described further herein below. The reader-printer housing 212 may be made of any suitable material. In some reader-printer embodiments, the reader system 214 is removable such that the reader-printer 210 is configurable in a printer-only version.

The reader-printer housing 212 shown in FIG. 7 includes a biometric scanner window 218, which in the first reader-printer embodiment is dimensioned for receiving and supporting a finger of a user of the reader-printer 210. The reader-printer 210 includes a biometric scanner 220 (not directly visible in FIG. 7) for biometrically scanning through the biometric scanner window 218. For example, the biometric scanner 220 in the first reader-printer embodiment is operable to scan a finger of the user when presented at the biometric scanner window 218. Additionally or alternatively, other biometric scanning techniques are possible, including scanning or imaging the user's eye or eyes, face, or any combination thereof for example. In some reader-printer embodiments, the biometric scanner 220 may be a fingerprint scanner, an eye scanner, including possibly an iris scanner, a facial scanner, including possibly a facial recognition scanner, a voiceprint scanner, other biometric scanning devices, or any combination thereof for example. The biometric scanner 220 may produce a code in response to its scanning operation. The code produced by the biometric scanner 220 may be used by the reader-printer 210 in the manner of a passcode, for example, to permit or deny operation of any or all of its functions and/or permit or deny access to any feature of the reader-printer 210, including permitting or denying access to open the reader-printer 210 for maintenance or other servicing for example.

In some embodiments, the biometric scanner 220 of the reader-printer 210 is operable to perform biometric scanning functions associated with the security checkpoint 10. In some embodiments, the biometric scanner 220 of the reader-printer 210 is operable to perform some or all of the scanning functions of the fingerprint scanner 40 of the security checkpoint 10. In some embodiments, the biometric scanner 220 of the reader-printer 210 is operable to perform some or all of the scanning functions of the palm-print scanner of the security checkpoint 10.

The reader-printer 210 in the first reader-printer embodiment includes a reader-printer display 222 attached to the reader-printer housing 212. The reader-printer 210 is operable to display on the reader-printer display 222 operational information relating to the various functions of the reader-printer 210. In the first reader-printer embodiment, the reader-printer display 222 is a liquid-crystal display (LCD). Additionally or alternatively, the reader-printer 210 may include a connector for connecting an externally connected monitor (not shown) to the reader-printer 210 for displaying such operational information. Additionally or alternatively, the reader-printer 210 may include any number of indicator lights, such as the indicators 224 shown in FIG. 7.

In some reader-printer embodiments, the reader-printer display 222 is a touch-screen display and the reader-printer 210 is operable to receive user input via the touch-screen reader-printer display 222. In some reader-printer embodiments, the reader-printer 210 includes both a non-touch screen display and a touch-screen display, one of which is the reader-printer display 222 shown in FIG. 7. Additionally or alternatively, the reader-printer 210 may include keys, a keyboard, buttons, such as the pushbuttons 226 shown in FIG. 7, mouse connector, a communications port such as an Ethernet and/or USB hub, any combination thereof for example, or other suitable devices for receiving user input.

In some embodiments, the reader-printer display 222 is operable to perform display functions associated with the security checkpoint 10. In some embodiments, the reader-printer display 222 is operable to perform some or all of the display functions of the display 38 of the security checkpoint 10.

In general, the operation of the reader-printer 210 may be controlled by the user via the user interface components of the reader-printer 210, including the indicators 224, reader-printer display 222 and the pushbuttons 226; via an external computer (not shown) connected to the reader-printer 210; remotely via any wired or wireless communications channel between the reader-printer 210 and the remote device; via user interface components of the security checkpoint 10; or any combination thereof for example. The remote device may be a central server (not shown), desktop computer (not shown) or any mobile device (not shown), for example. In variations, the user interface components of the reader-printer 210 and those of the security checkpoint 10 may be the same or different components, for example. In some embodiments, the security checkpoint 10 includes one or more of the user interface components of the reader-printer 210.

The reader-printer 210 is operable to read, authenticate and print on documents and other value items, such as the booklet 228 shown in FIG. 7, and to print on documents and other value items, such as the booklet 228. While FIG. 7 shows a booklet 228 and reference is made herein to the booklet 228 by way of example, it will be appreciated by a person of ordinary skill in the art that the present invention is equally applicable to any value item of known or otherwise determinable dimensions, including documents of various sizes, documents having specific known dimensions, bound documents, booklet-type documents, unbound documents, sheet-like documents, single-sheet documents, card-like documents, cards, including financial transaction cards, driver's licenses, identification documents, birth certificates, official papers, paper sheets, product labels, tags, stickers, products, or other value items.

The reader-printer 210 is configured to receive the booklet 228 for reading and authentication, such as by receiving the booklet 228 at the booklet support 230 shown in FIG. 7. In the first reader-printer embodiment, the reader-printer 210 is operable to receive the booklet 228 at the booklet support 230 by the user presenting the booklet 228 at the booklet support 230. In some reader-printer embodiments, however, the reader-printer 210 is operable to receive the booklet 228 from an automated feeder of value items, including for example sheet feeders and/or booklet feeders either or both of which may be a stacking feeder.

In some embodiments, the reader system 214 of the reader-printer 210 is operable to perform reading, verification and/or authentication functions associated with the security checkpoint 10. In some embodiments, the reader system 214 of the reader-printer 210 is operable to perform some or all of the scanning functions of the document scanner 42 of the security checkpoint 10. In some embodiments, the reader system 214 of the reader-printer 210 is operable to perform some or all of the reading functions of the passport reader 134 of the security checkpoint 10.

In the first reader-printer embodiment, the booklet support 230 is transparent, thereby permitting an imaging device (not visible in FIG. 7) of the reader system 214 to produce images of a booklet 228 being supported by the booklet support 230 when one or more sources (not visible in FIG. 7) of electromagnetic radiation housed within the reader-printer housing 212 are emitting electromagnetic radiation of selectable wavelengths toward the booklet support 230. In the first reader-printer embodiment, the reader system imaging device and the sources have line-of-sight positioning within the reader-printer housing 212 relative to the booklet support 230, such as by having internal walls (not visible in FIG. 7) projecting inwardly from around the perimeter of the booklet support 230, the sources being attached to such internal walls and directed toward the booklet support 230, the reader system imaging device being mounted within the reader-printer housing 212 adjacent ends of such walls and generally facing the booklet support 230. In some reader-printer embodiments, the reader system imaging device is mounted adjacent the bottom inner surface of the reader-printer housing 212. In some reader-printer embodiments, the reader-printer 210 includes redirecting mirrors for redirecting the path of electromagnetic radiation produced by the sources, reflected from the booklet 228 positioned at the booklet support 230, and received by the reader system imaging device. In such reader-printer embodiments, redirecting mirrors advantageously permit greater flexibility of location and position within the reader-printer housing 212 of the sources and the reader system imaging device. In general, the reader system imaging device may be mounted anywhere and directed in any direction provided the reader system imaging device is operable to capture images of the booklet 228 when it is being supported by the booklet support 230.

In some reader-printer embodiments, the reader-printer 210 includes a receiving slot 232 defined by an upper flange 234 for slidably receiving a booklet 228 at the booklet support 230. The upper flange 234 shown in FIG. 7 is three-sided to form the receiving slot 232. In the first reader-printer embodiment, the reader-printer 210 includes one or more reader sensors 236 (not directly visible in FIG. 7) for sensing the presence of a booklet 228 at the booklet support 230, such as by sensing the presence of a booklet 228 having been slid a sufficient distance into the receiving slot 232. The reader sensor 236 may be any suitable sensor such as a laser, LED, microwave or infrared presence sensor, motion detector, proximity sensor, similar detection sensor, ultra-sound sensor, mechanical sensor, or any combination thereof for example.

In the first reader-printer embodiment, at least one reader sensor 236 is located at a distal end 238 of the booklet support 230 so as to indicate when the booklet 228 has been fully inserted into the receiving slot 232 as far as the distal end 238. In various reader-printer embodiments, one or more reader sensors 236 may be located anywhere along the upper flange 234 and/or anywhere around the perimeter of the booklet support 230. Some reader-printer embodiments include multiple reader sensors 236 spaced apart along the perimeter of the booklet support 230 so as to define a grid on the booklet support 230, thereby advantageously facilitating identification of the type of document (e.g. passport, identification card, etc.) or other value item being received at the booklet support 230 on the basis of the size of the value item being received. Additionally or alternatively, the reader system imaging device (not shown) or other imaging camera (not shown) disposed within the reader-printer housing 212 and directed toward the booklet support 230 may be employed to sense the presence of the booklet 228 at the booklet support 230, thereby acting as a reader sensor 236.

In some reader-printer embodiments, the reader-printer 210 includes an enclosure (not shown) for enclosing the reader system 214. The enclosure may be dimensioned such that the reader system 214 is separate, including possibly being removable, from the remainder of the reader-printer housing 212.

In the first reader-printer embodiment, the reader-printer 210 includes an inlet, such as the printer inlet 240 shown in FIGS. 7 and 8, for receiving the booklet 228 or other value item. The reader-printer 210 in the first reader-printer embodiment also includes an access door, such as the inlet flap 242 shown in FIG. 7, through which the booklet 228 can pass when being received by the printer inlet 240. In some reader-printer embodiments, the inlet flap 242 includes a transparent window for viewing into the reader-printer housing 212. In some reader-printer embodiments, the inlet flap 242 will not open for access unless appropriate identification credentials are obtained, such as by one or more of: (a) the operation of the biometric scanner 220; (b) the entry of a suitable passcode; and (c) the authentication of the booklet 228 or other value item, including a document that may be the same as or different from the booklet 228, by operation of the reader system 214, for example.

In some reader-printer embodiments, the reader-printer 210 includes an imaging device (not shown) such as a camera disposed within the reader-printer housing 212 and directed toward the typical location of the face of a technician opening the housing 212 for servicing, and the reader-printer 210 is operable to capture an image, including possibly a streaming video of images, whenever the housing is opened in the manner of servicing, and operable to record the image or images in a record log associated with the reader-printer 210.

In some reader-printer embodiments, the reader-printer 210 includes an imaging device (not shown) such as a camera disposed within the reader-printer housing 212 and directed toward the value item after printing has occurred. In such reader-printer embodiments, the reader-printer 210 may be operable to perform any or all of the following quality assurance functions: (a) capturing quality assurance images, including possibly a streaming video of images, of the printing that has occurred; (b) displaying the quality assurance images on the reader-printer display 222 or other connected display (not shown); (c) receiving as user input an indication of the user's acceptance or rejection of the quality of the printing that has occurred; (d) performing automated image analysis for determining an indication of quality associated with the quality assurance images; (e) transmitting the indication of quality received or determined by the reader-printer 210 to a remote device (e.g. central server); (f) transmitting the quality assurance images to a remote device (e.g. central server); and (g) receiving from the remote device an indication of the quality of the printing that has occurred.

In some reader-printer embodiments, the reader-printer 210 is operable to receive as user input a request to eject the booklet 228 any time after it has been inserted, and to eject, including possibly reverse ejecting out the printer inlet 240, the booklet 228.

In some reader-printer embodiments, the reader-printer 210 is operable to measure its internal environment, such as by measuring the temperature and/or humidity of components housed within the reader-printer housing 212 and/or the space existing within the reader-printer housing 212. In such reader-printer embodiments, the reader-printer 210 includes one or more of a temperature sensor, humidity sensor, other environmental measuring devices, or any combination thereof for example.

The reader-printer 210 preferably includes a power management system which is configurable to accept specified electrical power, which may be alternating or direct current electricity at a specified voltage, including any specified voltage in the range of 12V to 240V for example. In some reader-printer embodiments, the reader-printer 210 includes one or more batteries for powering the reader-printer 210, including possibly rechargeable batteries. Additionally or alternatively, the reader-printer 210 may include an Uninterruptible Power Supply (UPS) for backup powering of the reader-printer 210. In some embodiments, the power management system of the reader-printer 210 is operable to manage electrical power associated with the security checkpoint 10.

Referring to FIG. 8, the reader-printer 210 includes one or more reader-printer processors 244 having processing circuits (not shown) and corresponding read-printer memory 246 having memory circuits (not shown). In some reader-printer embodiments, the reader system 214 and the printer system 216 include separate reader-printer processors 244 and separate reader-printer memories 246, while in some reader-printer embodiments a single reader-printer processor 244 and one read-printer memory 246 in electronic communication with the single reader-printer processor 244 controls both the reader system 214 and the printer system 216. Each reader-printer processor 244 may have any number processing circuits and each read-printer memory 246 may have any number of memory circuits. Processing and memory circuits of the reader system 214 and the printer system 216 may be in electronic communication with each other. Electronic communication may be wired or wireless, for example.

Each processing circuit typically includes one or more circuit units, such as a central processing unit (CPU), digital signal processor (DSP), embedded processor, etc., and any combination thereof operating independently or in parallel, including possibly operating redundantly. Each processing circuit may be implemented by one or more integrated circuits (IC), including being implemented by a monolithic integrated circuit (MIC), an Application Specific Integrated Circuit (ASIC), a Field Programmable Gate Array (FPGA), programmable logic controller (PLC), etc. or any combination thereof.

The memory circuits in the first reader-printer embodiment are typically operable to store digital representations of data or other information, including images, authentication codes, representations of security features and/or control information, and to store digital representations of program data or other information, including program code for directing operations of one or more of the processing circuits. One or more memory circuits of the reader-printer 210 may constitute a database (not shown), and/or be in electronic communication with a database.

Typically, the memory circuits are each all or part of a digital electronic integrated circuit or formed from a plurality of digital electronic integrated circuits. The memory circuits may be implemented as Read-Only Memory (ROM), Programmable Read-Only Memory (PROM), Erasable Programmable Read-Only Memory (EPROM), Electrically Erasable Programmable Read-Only Memory (EEPROM), flash memory, one or more flash drives, universal serial bus (USB) connected memory units, magnetic storage, optical storage, magneto-optical storage, etc. or any combination thereof, for example. The memory circuits may be operable to store digital representations as volatile memory, non-volatile memory, dynamic memory, etc. or any combination thereof.

The reader-printer processor 244 in conjunction with its corresponding read-printer memory 246 is typically operable to run any one or more operating systems, including real-time operating systems such as WinCE, Symbian, OSE, Embedded LINUX, non-real time operating systems such as Windows, Unix, Linux, and any combination thereof. The reader-printer processor 244 in conjunction with its corresponding read-printer memory 246 may be operable to implement multi-tasking methods involving multiple threads of executable code, for example.

In some embodiments, the reader-printer processor 244 is operable to perform processing functions associated with the security checkpoint 10. In some embodiments, the reader-printer processor 244 is operable to perform some or all of the processing functions associated with the controller 54 of the security checkpoint 10. In some embodiments, the reader-printer processor 244 is operable to perform some or all of the processing functions associated with the processor 56 of the security checkpoint 10. In variations, the processor 56 and the reader-printer processor 244 may be identical to, similar to or different from each other. In some embodiments, the reader-printer memory 246 is operable to perform data storage functions associated with the security checkpoint 10. In some embodiments, the reader-printer memory 246 is operable to perform some or all of the data storage functions associated with the memory 58 of the security checkpoint 10. In variations, the memory 58 and the reader-printer memory 246 may be identical to, similar to or different from each other.

In the first reader-printer embodiment, the reader-printer 210 includes a communications system 248 operable to effect communications with electronic devices which are external to the reader-printer 210. In some reader-printer embodiments, the reader-printer 210 is operable to effect communications via a Local Area Network (LAN), a Wide Area Network (WAN), private communications network, a Virtual Private Network (VPN), a secure (i.e. encrypted) communications network, the Internet, or any combination thereof. For example, the communications system 248 may be operable to provide communications between the reader-printer 210 and a remote device such as a central server (not shown), including a central server having a database which is accessible to the reader-printer 210. Communications between the reader-printer 210 and the remote device may include communications for the purpose of user control, including shared user control, reporting of logged records, other purposes, and any combination thereof for example.

The communications system 248 of the reader-printer 210 includes in various reader-printer embodiments any number of devices (not shown) for effecting such communications. By way of example, the communications system 248 may include any type of computer, including any general purpose digital computer, a modem, portable communications device, facsimile machine, telephone, including a land-line-connected or a wireless telephone such as a cellular or satellite telephone, radio, including a two-way radio, personal digital assistant or other equipment unit suitable for electronic communications. In various reader-printer embodiments, the communications system 248 may be operable to effect electronic communications via any wired or wireless connection, including a copper wire link, a coaxial cable link, a fiber-optic transmission link, a radio link, a cellular telephone link, a satellite link, a line-of-sight free optical link, and any combination thereof, for example. The communications system 248 may be controlled by the reader-printer processor 244 in conjunction with its corresponding read-printer memory 246. Additionally or alternatively, the communications system 248 may have its own processing circuits (not shown) and/or its own memory circuits (not shown).

In some embodiments, the communications system 248 of the reader-printer 210 is operable to effect communications functions associated with the security checkpoint 10. In some embodiments, the communications system 248 of the reader-printer 210 is operable to effect some or all of the communications functions associated with the communications controller 64 of the security checkpoint 10.

As shown in FIG. 8, the reader-printer 210 includes in at least some reader-printer embodiments a location identification system 250 for identifying the location of the reader-printer 210. The location identification system 250 is operable to determine the location of the reader-printer 210, and may be operable to periodically or continuously monitor the location of the reader-printer 210. In some reader-printer embodiments, the location identification system 250 is operable to produce an alarm signal if the location of the reader-printer 210 is not within a user definable permitted zone, for example. In such reader-printer embodiments, the reader-printer 210 is operable to communicate the alarm signal and/or the current location of the reader-printer 210, such as by transmitting an indication of the alarm signal and/or the current location to the remote device (e.g. central server) using the communications system 248.

In some embodiments, the location identification system 250 of the reader-printer 210 is operable to determine location(s) associated with the security checkpoint 10.

As shown in FIG. 8, the printer system 216 receives a booklet 228 (FIG. 7) via the printer inlet 240 and releases the booklet 228 after printing via the printer outlet 252. In some embodiments, the printer system 216 of the reader-printer 210 is operable to perform printing functions associated with the security checkpoint 10. In some embodiments, the printer system 216 of the reader-printer 210 is operable to perform some or all of the printing functions associated with the printer 136 of the security checkpoint 10.

Figure 9:
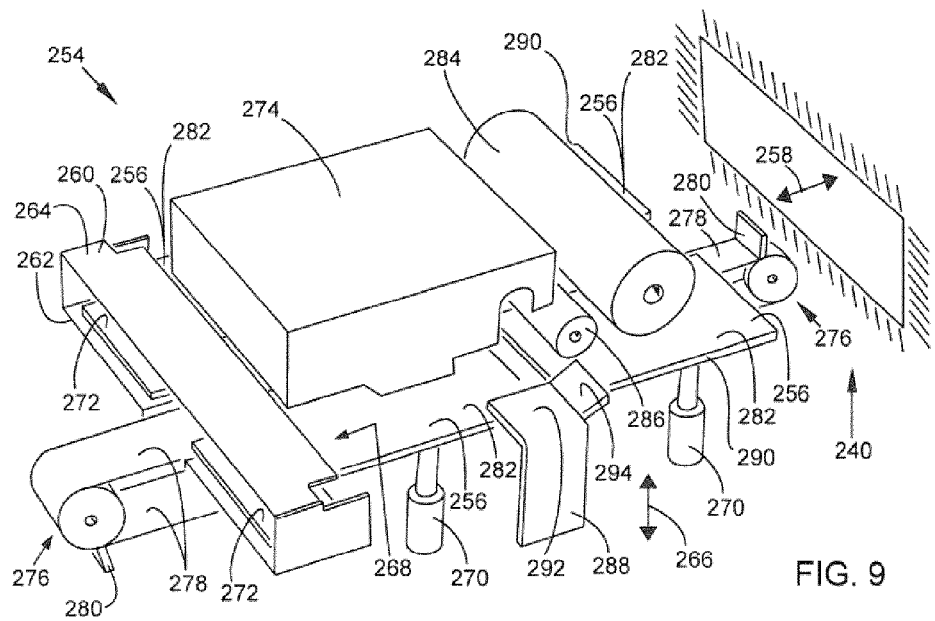
FIG. 9 is a perspective view of a portion of a transport system of the integrated reader-printer of FIG. 7, showing a platen and a transport frame.
Figure 10:
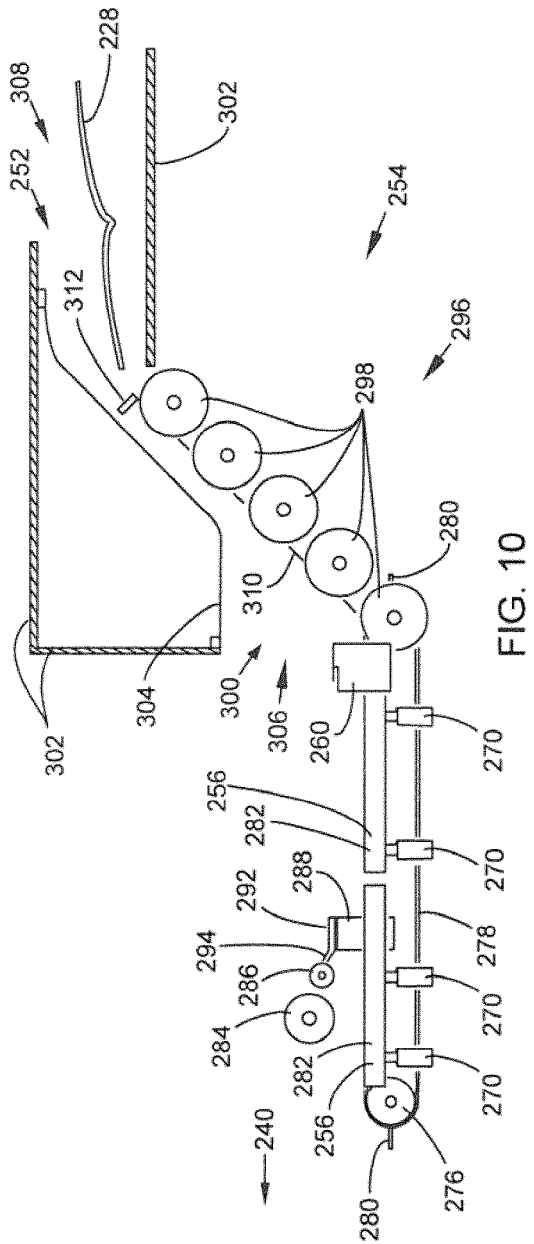
FIG. 10 is a side view of the transport system portion shown in FIG. 9, showing an exit conveyor.

Referring to FIGS. 9 and 10, the reader-printer 210 in the first reader-printer embodiment includes a transport system 254 for transporting the booklet 228 from the printer inlet 240 to the printer outlet 252 including during printing by the reader-printer 210. In some reader-printer embodiments, the reader system imaging device (not shown) is mounted above the transport system 254 between the transport system 254 and the booklet support 230. In some reader-printer embodiments, the reader system imaging device (not shown) is mounted below the transport system 254, which is dimensioned and positionable such that line-of-sight is achieved from the reader system imaging device to at least a portion of the booklet support 230 when the transport system 254 is so positioned.

In some reader-printer embodiments, the transport system 254 includes one or more of a tray, conveyor, rollers or the like for supporting the booklet 228 or other value item. The transport system 254 may be operable to extend such tray, conveyor, roller or the like outward through the printer inlet 240 for receiving the booklet 228 and transporting the booklet 228 into the reader-printer housing 212 through the printer inlet 240. In some reader-printer embodiments, the transport system 254 is operable to receive the booklet 228 being pushed by the user through the printer inlet 240 into the reader-printer housing 212. In some reader-printer embodiments, the transport system 254 is operable to receive the booklet 228 from an automated feeder (not shown).

The transport system 254 in the first reader-printer embodiment includes a platen 256 for supporting the booklet 228 (FIG. 7) received by the transport system 254.

In the first reader-printer embodiment, the platen 256 extends in a longitudinal direction (shown in FIG. 9 by the longitudinal arrow 258) from the printer inlet 240 to the transport frame 260. In some reader-printer embodiments, the platen 256 extends only midway between the printer inlet 240 and the transport frame 260. In some reader-printer embodiments, the platen 256 extends partway into the space defined by the transport frame 260 above a lower frame member, such as the lower frame plate 262 shown in FIG. 9, and below an upper frame member, such as the upper frame plate 264 shown in FIG. 9, of the transport frame 260. In such reader-printer embodiments, the platen 256 is moveable along a vertical direction (shown in FIG. 9 by the vertical arrow 266) such that the distal end 268 (not fully visible in FIG. 9) of the platen 256 is moveable between the lower frame plate 262 and the upper frame plate 264. In the first reader-printer embodiment, the platen 256 includes one or more platen posts 270 useable for effecting vertical movement of the platen 256.

In the first reader-printer embodiment, the transport frame 260 also includes a barrier, such as the stopper gate 272 shown in FIG. 9, which preferably can rotate from a horizontal position (shown in FIG. 9) to a vertical position (not shown). When the stopper gate 272 is in its vertical position, the stopper gate 272 can act to prevent the booklet 228 from being inserted into the reader-printer 210 past the stopper gate 272 or transported by the transport system 254 from the printer inlet 240 in the longitudinal direction 258 past the stopper gate 272.

In the first reader-printer embodiment, the reader-printer 210 includes one or more printer sensors (not directly visible in FIGS. 9 and 10) disposed in proximity to the stopper gate 272 for sensing the presence of the fully inserted booklet 228 having a leading edge thereof (i.e. the first edge of the booklet 228 to be inserted at the printer inlet 240) adjacent or otherwise proximate to the stopper gate 272 in its vertical position. In some reader-printer embodiments, the reader-printer 210 includes at least one printer sensor in proximity to the stopper gate 272 and at least two printer sensors disposed along opposing sides of the platen 256.

When the booklet 228 has been inserted into the reader-printer 210 and/or transported above the platen 256 until contacting or otherwise being proximate the stopper gate 272 in its vertical position, then upward movement of the platen 256 can be effected by the reader-printer 210 to clamp the booklet 228 at one edge thereof between the distal end 268 of the platen 256 and the upper frame plate 264. In some reader-printer embodiments, the upward movement of the platen 256 is effected in response to an indication from one or more printer sensors that the booklet 228 is in its fully inserted position, including possibly in response to at least two out of three printer sensors. In various reader-printer embodiments, the printer-reader 210 includes a mechanically-driven mechanism for effecting upward movement of the platen 256, an electronically actuated mechanism for effecting upward movement of the platen 256, or any combination thereof for example. In reader-printer embodiments having multiple platen 256 plates, the clamping platen 256 plates extending longitudinally into the space defined between the lower frame plate 262 and the upper frame plate 264 of the transport frame 260 are moved vertically to clamp the booklet 228 edge between the those platen 256 plates and the upper frame plate 264. Additionally or alternatively, one or more of the remaining platen 256 plates which do not extend longitudinally into the space defined between the lower frame plate 262 and the upper frame plate 264 may also be moved vertically in conjunction with the clamping platen 256 plates.

In the first reader-printer embodiment, the reader-printer 210 is operable to cause the platen 256 and the transport frame 260 to move together longitudinally so as to expose different portions of the clamped booklet 228 to printing by operation of the printhead 274. For example, the transport system 254 may include a motor (not shown) for driving an output gear (not shown) engaged to a toothed rail (not shown in FIGS. 9 and 10) such that rotation of the output gear causes movement of the platen 256 and the transport frame 260 along the toothed rail.

In reader-printer embodiments having multiple platen 256 plates, the clamping platen 256 plates move longitudinally together with the transport frame 260. Additionally or alternatively, one or more of the remaining platen 256 plates may also be moved longitudinally in conjunction with the clamping platen 256 plates.

In some reader-printer embodiments, the transport frame 260 includes a ramp (not shown in FIGS. 9 and 10) to assist directing the booklet 228 when it is exiting the transport frame 260 past the stopper gate 272 in a direction away from the printer inlet 240 and toward the printer outlet 252. In some reader-printer embodiments, the ramp extends at an angle upwardly and away from the lower frame plate 262.

Preferably, the stopper gate 272 and the platen 256 are dimensioned to avoid overlapping when the stopper gate 272 is in the horizontal position shown in FIG. 9. In addition or alternative to the horizontal position shown in FIG. 9, the stopper gate 272 in some reader-printer embodiments is rotatable to an exiting position (not shown in FIG. 9), which may be at an angle extending upwardly and away from the lower frame plate 262. In such reader-printer embodiments, the stopper gate 272 acts as a ramp to assist directing the booklet 228 when it is exiting the transport frame 260 along the angled stopper gate 272 in a direction away from the printer inlet 240 and toward the opposing-end printer outlet 252. Additionally or alternatively, in such reader-printer embodiments the stopper gate 272 need not be rotatable into the horizontal position shown in FIG. 9, provided the stopper gate 272 is operable to be placed in a position blocking further longitudinal movement of the booklet 228 past the stopper gate 272 and operable to be placed in a position permitting further longitudinal movement of the booklet 228 past the stopper gate 272 and away from the printer inlet 240.

In the first reader-printer embodiment shown in FIG. 9, the reader-printer 210 includes a transport conveyor 276 for conveying the booklet 228 from the printer inlet 240 toward the printer outlet 252 (FIG. 8), including either or both of toward and away from the printhead 274.

The transport system 254 of the first reader-printer embodiment is operable to receive the booklet 228 (not shown in FIG. 9) via the printer inlet 240. In variations, the transport system 254 of the first reader-printer embodiment may be operable to release or eject the booklet 228 at the same or opposing end of the transport system 254 as the printer inlet 240, or the transport system 254 of the first reader-printer embodiment may be operable to release or eject the booklet 228 at both the same and opposing ends of the transport system 254 as the printer inlet 240.

In some reader-printer embodiments, the printhead 274 is a commercially available printhead 274. In some reader-printer embodiments, the printer system 216 is a magnetic printer having a magnetic source of a magnetic field as part of the printhead 274 and/or mounted proximate the printhead 274 for example. In the first reader-printer embodiment, the printhead 274 is operable to print using a security ink having security features to assist in authenticating documents such as the booklet 228. In the first reader-printer embodiment, the transport conveyor 276 includes a conveyor belt 278 having a push-plate 280 projecting from the conveyor belt 278 for pushing the booklet 228 in the longitudinal direction 258 along a transport path defined by the transport conveyor 276.

In the first reader-printer embodiment, each transport conveyor 276 includes a pair of push-plates 280 projecting from the conveyor belt 278 at separated locations along the conveyor belt 278, thereby advantageously providing a second push-plate 280 at a receiving position when the first push-plate 280 has completed its role in ejecting the booklet 228. However, in some reader-printer embodiments only one push-plate 280 is employed for each conveyor belt 278. The printer system 216 may be operable to advance the transport conveyor 276 in one direction only, or the transport conveyor 276 may be reversible with the printer system 216 being operable to selectably advance the transport conveyor 276 in either opposing direction.

In some reader-printer embodiments as shown in FIG. 9, the transport conveyor 276 extends from adjacent the printer inlet 240 to a point proximate the transport frame 260. In some reader-printer embodiments, however, the transport conveyor 276 extends only mid-way between the printer inlet 240 and the transport frame 260. In some reader-printer embodiments as shown in FIG. 9, the transport conveyor 276 is vertically positioned such that its upper surface is adjacent the upper surface of the platen 256. The transport conveyor 276 may have any suitable length.

In the first reader-printer embodiment, the platen 256 is sectional and includes a number of platen sections 282. In some reader-printer embodiments, however, the platen 256 is not sectional and includes only one platen section 282. In other reader-printer embodiments, the platen 256 includes a pair of left and right platen sections 282, as shown in FIG. 9. In some reader-printer embodiments, one or both of the left and right platen sections 282 include fore and aft platen sections 282 such that the reader-printer 210 includes four platen sections 282 in total as shown in FIG. 9. Having left and right platen sections 282 advantageously permits the transport conveyor 276 to be disposed between such left and right platen sections 282. Having fore and aft platen sections 282 advantageously permits the fore and aft platen sections 282 to be resiliently disposed at different heights, possibly due to different thicknesses of different halves of the booklet 228 for example.

In the first reader-printer embodiment, the reader-printer 210 includes one or more feeding rollers of the same or different diameters and of the same or different lengths, such as the first feeding roller 284 and the smaller second feeding roller 286 shown in FIG. 9. As shown in FIG. 9, the feeding rollers 284 and 286 need not extend across the entire width of the platen 256. In the first reader-printer embodiment, the feeding rollers 284 and 286 preferably do not extend to the longitudinal edges 290 of the platen 256, and preferably do not extend to within 2.5 cm (1 inch) of the longitudinal edges 290 of the platen 256 and correspondingly not within 2.5 cm (1 inch) of the side edges of the booklet 228 (FIG. 7). In the first reader-printer embodiment, the first feeding roller 284 advantageously inhibits the booklet 228 from being inserted above the first feeding roller 284 and preferably guides the booklet 228 to extend between the second roller 286 and the platen 256 without adversely folding pages of the booklet 228. The second roller 286 advantageously holds central regions of pages of the booklet 228 against the platen 256 for better printing on the booklet 228 by operation of the printhead 274. In some reader-printer embodiments, one or both of the feeding rollers 284 and 286 are attached to the reader-printer housing 212. In some reader-printer embodiments, one or both of the feeding rollers 284 and 286 are attached to the printhead 274, which is typically attached to the reader-printer housing 212 via a printhead shaft (not shown) upon which the printhead 274 is operable to slide in transverse directions (i.e. perpendicular to the longitudinal directions and perpendicular to the vertical directions).

In the first reader-printer embodiment, the reader-printer 210 includes an edge bracket 288 extending vertically adjacent a longitudinal edge 290 of the platen 256. Additionally or alternatively, the edge bracket 288 includes a cantilevered bracket section 292 which advantageously inhibits the upward extension of the inserted booklet 228 while not clamping the inserted booklet 228 at its side edges (not shown). Typically, the edge bracket 288 is attached to the reader-printer housing 212. In some reader-printer embodiments, the cantilevered bracket section 292 is horizontally disposed and flat. Additionally or alternatively, the cantilevered bracket section 292 may include an inclined portion 294 which faces toward the printer inlet 240 as shown in FIG. 9. In some reader-printer embodiments, a pair (not visible in FIG. 9) of edge brackets 288 are disposed adjacent both opposing longitudinal edges 290 of the platen 256.

In some reader-printer embodiments, the edge bracket 288 includes a pair of upper and lower cantilevered bracket sections 292 at opposing upper and lower ends of the edge bracket 288, so as to form a U-shaped bracket (not shown). In some reader-printer embodiments, the edge bracket 288 is extended longitudinally, including forming a U-shaped channel along one or both side edges of the platen 256.

In the first reader-printer embodiment, the printer system 216 includes an imaging system (not shown) for imaging the inserted and clamped booklet 228 for the purposes of either or both of machine-vision and human vision inspection. Such inspection can occur before, during or after printing by the printer system 216 onto the booklet 228. The imaging system is operable in the first reader-printer embodiment to produce images of the booklet 228, including producing images at a printable area of the booklet 228. In the first reader-printer embodiment, the reader-printer 210 is operable to display images produced by the imaging system on the reader-printer display 222 for viewing by the user. In some reader-printer embodiments, the imaging system includes a printer system imaging device and/or quality assurance imaging device such as a camera disposed adjacent to or otherwise in proximity to the printhead 274, including possibly between the printhead 274 and the printer inlet 240. The imaging system may be operable to produce still images, video images, or any combination thereof for example. In some reader-printer embodiments, the reader-printer 210 is operable to effect visible wavelength lighting directed at the inserted booklet 228 by operation of selected sources of electromagnetic radiation of the reader system 214, other sources of the printer system 216, or any combination thereof for example. In some reader-printer embodiments, visible wavelength lighting is directed at the inserted booklet 228 during imaging of the inserted booklet 228 by the imaging system. The sources of visible wavelength lighting may be mounted within the reader-printer housing 212 on one or more sides around the printhead 274, for example. Such sources may also be employed to assist drying or curing of the ink following printing on the booklet 228.

In some reader-printer embodiments, the reader-printer 210 is operable to receive user input indicating a location or area of the booklet 228 upon which printing should occur, and to print at the indicated location or area. By way of example in the case of a touch screen, the user may be permitted to indicate a desired location for printing by touching the touch-screen at location thereof corresponding to the user's desired location when the touch-screen is displaying a printable page of the booklet 228.

The reader-printer 210 in the first reader-printer embodiment is operable to cause downward movement of the platen 256 so as to release from clamping the booklet 228, including releasing the booklet 228 after printing and/or stamping on the booklet 228 is completed. In some reader-printer embodiments, the reader-printer 210 is operable to release the booklet 228 only when the transport system 254 is at a specifiable longitudinal position.

Referring to FIG. 10, the transport system 254 in the first reader-printer embodiment may include an exit conveyor 296 for conveying the inserted booklet 228 out of the reader-printer 210 at the printer outlet 252 when the printer outlet 252 is disposed at the opposing end of the transport system 254 from the printer inlet 240.

The exit conveyor 296 in the first reader-printer embodiment includes a number of rollers 298 disposed along an incline 300 between the transport frame 260 (at its distal extent of longitudinal movement) and the opposing-end printer outlet 252 of the reader-printer 210. As shown in FIG. 10, the printer outlet 252 is defined by walls 302 of the reader-printer housing 212 and may have any suitable shape or size. In the first reader-printer embodiment, the transport system 254 includes an upper exit guide 304 for guiding the booklet toward the printer outlet 252. Preferably, the upper exit guide 304 is dimensioned to contact the booklet 228 only along side edges of the booklet 228, thereby advantageously avoiding contact with recently printed areas of the booklet 228. In some reader-printer embodiments, the transport system 254 includes a pair of upper exit guides 304 mounted proximate opposing side edges of the booklet 228. In some reader-printer embodiments, the distance between the opposing upper exit guides 304 is adjustable, including possibly being manually adjustable and/or automatically adjustable such as in response to imaging or other sensing by the reader-printer 210 of the booklet 228. In the first reader-printer embodiment, the upper exit guide 304 and the rollers 298 are dimensioned to not clamp the booklet 228. Additionally or alternatively, the transport system 254 may include upper rollers (not shown) to assist movement of the booklet 228 toward the printer outlet 252. Preferably, such upper rollers are dimensioned to contact the booklet 228 only along side edges of the booklet 228, thereby advantageously avoiding contact with recently printed areas of the booklet 228.

In some reader-printer embodiments, the upper exit guide 304, upper rollers, or both the upper exit guide 304 and the upper rollers are dimensioned to permit card-like documents made of rigid or semi-rigid materials, such as booklets having at least one page thereof made of a rigid material such as a polycarbonate sheet such that one-half of an open booklet is rigid, to exit the reader-printer 210 via the opposing-end printer outlet 252. For example, the transport system 254 may be dimensioned to provide sufficient lower clearance 306 between the upper exit guide 304 and the exit conveyor 296 at the bottom of the incline 300 and sufficient upper clearance 308 between the upper exit guide 304 and the exit conveyor 296 at the top of the incline 300 to permit a booklet having a rigid page to exit the reader-printer 210 via the opposing-end printer outlet 252. In some reader-printer embodiments, the minimum lower clearance 306 is 10 cm (3.94 inches) and the minimum upper clearance 308 is 1.5 cm (0.59 inches).

In the first reader-printer embodiment, the reader-printer 210 is dimensioned so as to be suitable for mounting beneath a tabletop proximate an edge of the table (not shown) such that the user can position the booklet 228 for being received by the reader system 214 at the booklet support 230 from beside the table near the tabletop; position the booklet 228 for being received by the printer system 216 via the printer inlet 240 from beside the table below and proximate to the tabletop; and pick up the booklet 228 after printing from the upper surface of the tabletop after exiting the printer outlet 252 to rest on the tabletop. The reader-printer 210 is dimensioned to permit various mounting arrangements such that the printer inlet 240 is aligned with the front edge of the table (not shown); the booklet support 230 is disposed within a notch cut into the front of the table (not shown); the printer outlet 252 is disposed at a cut-out or other aperture through the tabletop of the table (not shown); other mounting arrangements; or any combination thereof for example. Such mounting arrangements advantageously permit reading for authentication and printing of the booklets 228 while occupying minimal tabletop area.

In some reader-printer embodiments, the exit conveyor 296 includes an exit conveyor belt 310 operable to assist movement of the booklet 228 toward the printer outlet 252. In such reader-printer embodiments, the exit conveyor belt 310 may include an exit push-plate 312 to assist in pushing the booklet 228 along the incline 300 and to push the booklet 228 out of the reader-printer 210. The exit conveyor 296 and the exit conveyor belt 310 may have any suitable length.

Additionally or alternatively, the transport system 254 may include one or more exit arms (not shown) reaching downwardly from the top of the reader-printer housing 212 to contact a trailing edge of the booklet 228 and to push, or assist in pushing, the booklet 228 up the incline 300 toward the printer outlet 252.

Additionally or alternatively, the transport system 254 may include a clamping mechanism that clamps the booklet 228 along its leading edge only and pulls the booklet 228 up the incline 300 toward the printer outlet 252. For example, in some reader-printer embodiments the transport frame 260 is operable to be moved up the incline 300 to the printer outlet 252 so as to pull the booklet 228 to the printer outlet 252, including possibly pulling the booklet 228 out of the reader-printer 210. Additionally or alternatively, the reader-printer 210 in some reader-printer embodiments includes a "finger-and-thumb" style clamping arm for clamping the booklet 228 at its leading edge and pulling the booklet 228 to the printer outlet 252, including possibly pulling the booklet 228 out of the reader-printer 210.

While not shown in FIG. 10, the reader-printer 210 in some reader-printer embodiments includes an exit door or exit flap at the printer outlet 252 through which an exiting booklet 228 can pass while advantageously inhibiting the entry of debris and other matter into the reader-printer 210.

While FIG. 10 shows the printer outlet 252 disposed near the top of the reader-printer housing 212, in some reader-printer embodiments the printer outlet 252 is disposed to the rear of the reader-printer 210 substantially level with the transport frame 260. In some reader-printer embodiments, the transport conveyor 276 continues past the printhead 274 toward the rear of the reader-printer housing 212. In some reader-printer embodiments, the exit conveyor 296 is rotatable between an inclined position such as shown in FIG. 10 and a horizontal position substantially level with the transport conveyor 276.

While not shown in FIG. 10, the reader-printer 210 in some reader-printer embodiments includes a U-shaped channel guide extending along the incline 300 and/or extendable longitudinally with the edge bracket 288. In some reader-printer embodiments, the inside height of such U-shaped channel is dimensioned to provide sufficient clearance for permitting rigid or semi-rigid documents to pass therethrough, such as by varying the inside height of such U-shaped channel to provide the minimum clearance throughout and to provide the maximum clearance required at the bends of the booklet 228 path.

Second Reader-Printer Embodiment

Referring to FIG. 11, the transport system 254 in accordance with a second reader-printer embodiment of the invention includes one support plate 400 and a pair of parallel, spaced apart conveyors 402 disposed on opposite sides of the support plate 400. The conveyors 402 may have any suitable length.

A portion only of the reader-printer housing 212 is shown as a cut-out in FIG. 11, for ease of illustration. In the second reader-printer embodiment, inlet guides 404 are attached to the housing at the printer inlet 240 to direct a booklet 228 (not shown in FIG. 11) passing through the printer inlet 240 to the space between the support plate 402 and the first and second feeding rollers 284 and 286. While two inlet guides 404 are visible in FIG. 11, in general any number of inlet guides 404 may be employed. For example, four inlet guides 404 projecting from the printer inlet 240 on all four sides around the perimeter of the printer inlet 240 may be employed. In variations, the reader-printer 210 may include only two inlet guides 404 projecting from above and below the printer inlet 240, only two inlet guides 404 projecting from left and right sides of the printer inlet 240, only one inlet guide 404 projecting from the printer inlet 240 at any one edge thereof, or no inlet guides 404 may be used at all.

The support plate 400 shown in FIG. 11 is similar to the platen 256 (FIGS. 9 and 10), however, the support plate 400 shown in FIG. 11 does not extend beneath the printhead 274 (shown by dotted line in FIG. 11) as far as the printing zone where printing takes place. In some reader-printer embodiments, the support plate 400 does not extend beneath the printhead 274 at all. In other reader-printer embodiments, however, the support plate 400 may extend as far as the printing zone where printing takes place so as to form a supporting surface during printing in the manner of a platen.

The support plate 400 is shown in FIG. 11 as being attached to posts 406. In the second reader-printer embodiment, the reader-printer 210 is operable to cause the support-plate 400 to move vertically up and down to be positioned closer and further from the feeding rollers 284 and 286. In general, any suitable manner of moving the support plate 400 vertically may be employed. For example, any elevator-type mechanism may be employed. Such elevator-type mechanism may include a motor (not shown) with a rotating shaft output, a linear motion motor (not shown), gearbox (not shown), crankshaft (not shown), other components, and any combination thereof for example. The elevator-type mechanism may be computer controlled, electronically controlled, electronically actuated, mechanically actuated, mechanically driven, or any combination thereof for example.

In the second reader-printer embodiment, the support plate 400 and the feeding rollers 284 and 286 are centrally located about a central longitudinal axis of the transport system 254 and extend transversely on either side of the central longitudinal axis of the transport system 254. In the second reader-printer embodiment, the support plate 400, the feeding rollers 284 and 286, or both the support plate 400 and the feeding rollers 284 and 286 do not extend transversely as far as the position of the vertical side inlet guides 404. In the second reader-printer embodiment, the feeding rollers 284 and 286 need not extend across the entire width of the support plate 400. In the second reader-printer embodiment, the feeding rollers 284 and 286 preferably do not extend to the longitudinal edges of the support plate 400, and preferably do not extend to within 2.5 cm (1 inch) of the longitudinal edges of the support plate 400 and correspondingly not within 2.5 cm (1 inch) of the side edges of the booklet 228 (FIG. 7).

Referring to FIGS. 11 and 12, the clamping frame 408 includes an upper clamping plate 410 and a lower clamping plate 412. In the second reader-printer embodiment, the lower clamping plate 412 is moveable vertically by any suitable device so as to provide clamping of the leading edge 414 of the booklet 228 between the upper and lower clamping plates 410 and 412. For example, any elevator-type mechanism may be employed, which may include any suitable components and may be computer controlled, electronically controlled, electronically actuated, mechanically actuated, mechanically driven, or any combination thereof for example. Additionally or alternatively, the clamping frame 408 may include one or more magnets (not shown) of any type to create an attractive magnetic force between the upper and lower clamping plates 410 and 412. By way of example, an electromagnet (not shown) attached to either or both of the upper and lower clamping plates 410 and 412 may be employed to move the lower clamping plate 412 vertically toward the upper clamping plate 410. Additionally or alternatively, one or more magnets may be employed to provide reinforcement of the clamping force between the upper and lower clamping plates 410 and 412. In some reader-printer embodiments, one or more permanent magnets (not shown) are disposed at one of the upper and lower clamping plates 410 and 412 and one or more electromagnets (not shown) are disposed at the other of the upper and lower clamping plates 410 and 412. In operation, the electromagnets (not shown) may be turned on when clamping or reinforcement of clamping is desired.

As shown in FIG. 11, the clamping frame 408 is moveable longitudinally along the rail or rack 416 via a pinion gear (not shown). For ease of illustration, all components of the rack-and-pinion linear drive system for moving the clamping frame 408 longitudinally along the rack 416 are not shown in FIG. 11. In general, any linear motion system may be employed for moving the clamping frame 408 longitudinally, including any pulley system, conveyor system, screw-drive system, other similar system, or any combination thereof for example. In the second reader-printer embodiment, the rack 416 is longer than that shown in FIG. 11, and in general may be of any suitable length.

The transport system 254 of the second reader-printer embodiment is operable to receive the booklet 228 (not shown in FIG. 11) via the printer inlet 240. In variations, the transport system 254 of the second reader-printer embodiment may be operable to release or eject the booklet 228 at the same or opposing end of the transport system 254 as the printer inlet 240, or the transport system 254 of the second reader-printer embodiment may be operable to release or eject the booklet 228 at both the same and opposing ends of the transport system 254 as the printer inlet 240. By way of example, FIG. 11 shows the printer outlet 252 at the opposing end of the transport system 254 as the printer inlet 240.

The exit ramp 418 of the second reader-printer embodiment shown in FIG. 11 has a proximal end 420 adjacent the conveyors 402 and the clamping frame 408, and has a distal end 422 at the printer outlet 252. The exit ramp 418 includes an exit clamp 424 along one side edge of the exit ramp 418. The exit clamp 424 in the second reader-printer embodiment includes an upper clamping finger 426 and a lower clamping finger 428. In some reader-printer embodiments, the lower clamping finger 428 is implemented by the floor 430 itself of the exit ramp 418. The reader-printer 210 in the second reader-printer embodiment is operable to cause the upper and lower clamping fingers 426 and 428 to come together for clamping. In the second reader-printer embodiment, the reader-printer 210 is also operable to cause the exit clamp 424 to move longitudinally along the exit ramp 418, such as along the incline 300 defined by the exit ramp 418. While not shown in FIG. 11, any suitable mechanism for causing linear motion of the exit clamp 424 along the exit ramp 418 may be employed, including any pulley system, conveyor system, screw-drive system, rack-and-pinion system, other similar system, or any combination thereof for example.

In variations, the exit clamp 424 may be located on either side of the exit ramp 418, or there may be two exit clamps 424 with one on each side for example. In some reader-printer embodiments, such as where the exit ramp 418 is sufficiently short or is of sufficiently low height, no exit clamp 424 is included in the reader-printer 210.

In some reader-printer embodiments (not shown), the reader-printer 210 includes a clamping mechanism operable to clamp the leading edge 414 of the booklet 228 and pull the booklet 228 up the exit ramp 418. By way of example, the clamping frame 408 is operable in some reader-printer embodiments to continue longitudinal movement along the exit ramp 418 to the printer outlet 252. Additionally or alternatively in some reader-printer embodiments, one or more fingerlike clamps such as the exit clamp 424 are located centrally, and/or on either side of the central longitudinal axis (not shown) of the exit ramp 418, to clamp the leading edge 414 of the booklet 228 and pull the booklet 228 along the exit ramp 418 to the printer outlet 252.

The exit ramp 418 shown in FIG. 11 includes a left sidewall 432 opposite a right sidewall 434 and overhangs 436 for guiding the booklet 228 into and along the exit ramp 418. As shown in FIG. 11, the vertical distance between the floor 430 of the exit ramp 418 and the overhangs 436 is greatest at the entry of the exit ramp 418 proximate the conveyors 402, which advantageously permits rigid or semi-rigid booklets 228, such as booklets 228 in which one or both of its half-sections are rigid or semi-rigid, to travel through the clamping frame 408 at a vertical angle toward the top of the exit ramp 418 via the bend created at the transition from the clamping frame 408 to the exit ramp 418 without jamming against the overhangs 436.

As shown in FIG. 11, the right sidewall 434 does not extend all the way to the distal end 422 of the exit ramp 418, and a portion of the right side of the floor 430 of the exit ramp 418 is cut away. The cut-away 438 of the exit ramp 418 advantageously provides free space for grasping of the booklet 228 by the user upon ejection of the booklet 228 from the reader-printer 210. The cut-away 438 may be located at either or both of the left and right sides of the exit ramp 418. While FIG. 11 shows the cut-away 438 extending most of the length of the exit ramp 418, in some reader-printer embodiments the cut-away 438 is provided only at one or both distal corners of the exit ramp 418.

In some reader-printer embodiments, the transport system 254 includes one or more hinges (not shown) for permitting the exit ramp 418 to rotate about its proximal end 420, thereby advantageously permitting the booklets 228 to exit the reader-printer 210 at selectable locations. By way of example, the exit ramp 418 may be rotatable to cause the booklet 228 to protrude or exit completely from the reader-printer 210 horizontally, including possibly horizontally proximate the rear of the reader-printer 210; vertically, including possibly vertically proximate the top or bottom of the reader-printer 210; or at any angle therebetween. In some reader-printer embodiments, the exit ramp 418 can be manually rotated by the user. Additionally or alternatively, the transport system 254 may include a motor (not shown) or other driver for causing rotation of the exit ramp 418.

In some reader-printer embodiments, the exit ramp 418 is telescopic, thereby advantageously permitting the printer outlet 252 to be located at a desired distance from the printer inlet 240. In such reader-printer embodiments, the exit ramp 418 may be extendable and retractable manually. Additionally or alternatively, the transport system 254 may include a motor or other driver for causing telescopic extension and/or retraction of the exit ramp 418.

In some reader-printer embodiments, the exit ramp 418 is replaceable and can be replaced by various exit ramps having different slopes of incline 300 or no incline at all and/or different lengths.

In FIG. 12, the printer system 216 is shown in a position for receiving a booklet 228 through the printer inlet 240. In such receiving position of the printer system 216, the clamping frame 408 is positioned to receive a leading edge 414 of the booklet 228, and may be positioned beneath the printhead 274 or otherwise close to the printer inlet 240. In the second reader-printer embodiment, the clamping frame 408 is positioned close to the feeding rollers 284 and 286 when the printer system 216 is in its receiving position. In the second reader-printer embodiment, the support plate 400 does not extend into the space defined by the clamping frame 408. In the receiving position of the printer system 216, the support plate 400 is in its lowered position and the posts 406 are contracted in length, thereby creating a relatively large vertical gap between the support plate 400 and the feeding rollers 284 and 286. The reader-printer 210 preferably includes in the second reader-printer embodiment one or more printer sensors (not directly visible in FIG. 12) for detecting the presence of the leading edge 414 of the inserted booklet 228 when the leading edge 414 is adjacent or otherwise proximate to the stopper gate 272 (not visible in FIG. 12) of the clamping frame 408.

In some reader-printer embodiments, the clamping frame 408 is operable to move to a position between the printer inlet 240 and the second feeding roller 286, such as when a received object is being reverse ejected out the printer inlet 240. In such reader-printer embodiments, either or both of the clamping frame 408 and the second feeding roller 286 may be operable to move vertically so as to permit the clamping frame 408 to pass under the second feeding roller 286 as the clamping frame 408 moves toward the printer inlet 240. However, in some reader-printer embodiments the clamping frame 408 is not permitted to move to a position between the printer inlet 240 and the second feeding roller 286, even if the received object is being reverse ejected out of the printer inlet 240. In some reader-printer embodiments, the reader-printer 210 is not operable to reverse eject a received object out of the printer inlet 240.

When the printer sensors 272 at the stopper gate 272 detect the presence of the leading edge 414 of the booklet 228 within the clamping frame 408, the printer system 216 is operable to cause the upper clamping plate 410 and the lower clamping plate 412 to come together. In the second reader-printer embodiment, the lower clamping plate 412 moves upwardly toward the fixed upper clamping plate 410 to clamp the booklet 228 therebetween along at least a portion of the leading edge 414 of the booklet 228. The printer system 216 is also operable to cause the support plate 400 and at least the second feeding roller 286 to come together. In the second reader-printer embodiment, the support plate 400 moves upwardly toward the fixed second feeding roller 286 until the booklet 228 is clamped at a non-edge area of the booklet 228 between the support plate 400 and the second feeding roller 286. Additionally or alternatively, the booklet 228 may be clamped between the support plate 400 and the first feeding roller 284, or between the support plate 400 and both the first and second feeding rollers 284 and 286. In variations, any number of feeding rollers may be employed and any such feeding roller may be employed for clamping in conjunction with the support plate 400. In some reader-printer embodiments, however, the booklet 228 is not clamped between the support plate 400 and any feeding roller, such as by the support plate 400 not being moved upwardly far enough to clamp the booklet 228 between the support plate 400 and either of the feeding rollers 284 and 286.

Figure 13:
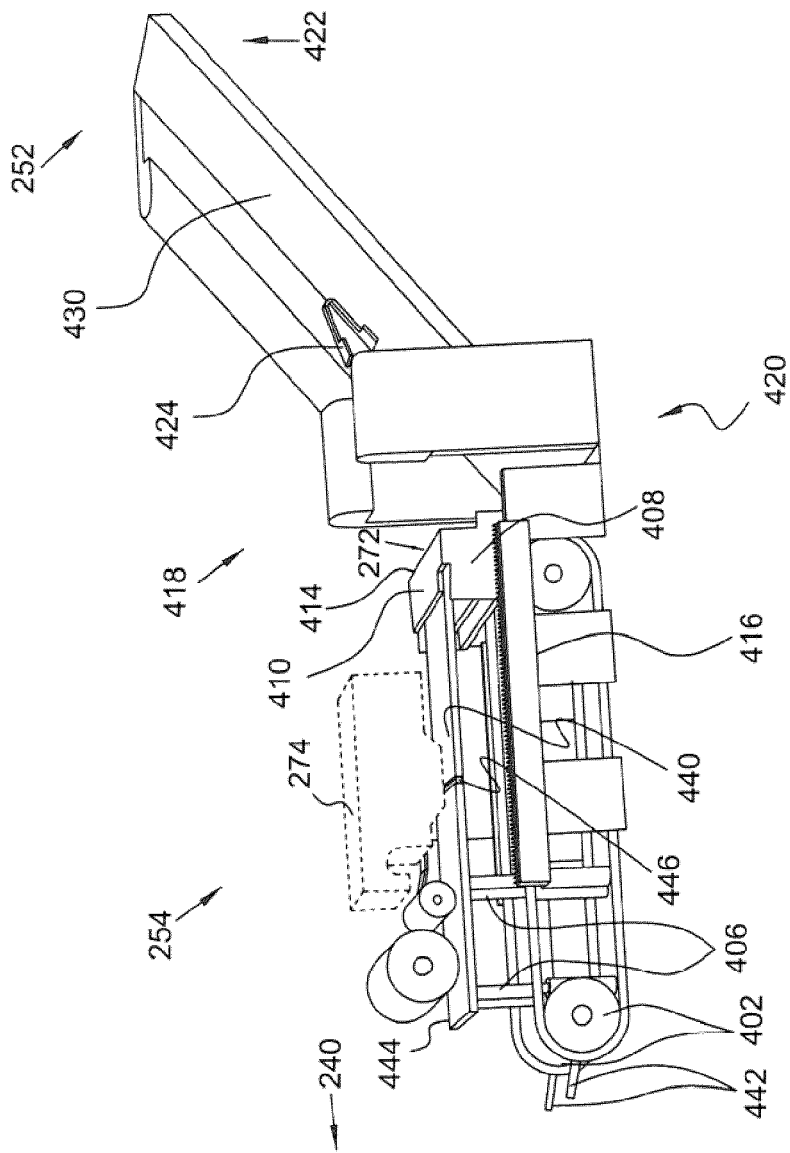
FIG. 13 is a perspective view of the transport system of FIG. 11, showing the booklet during printing.

FIG. 13 shows the printer system 216 in a printing position for printing on the booklet 228. In such printing position, at least a portion of a printable area 440 of the booklet 228 is directly beneath the printhead 274. The printer system 216 is operable to cause the clamping frame 408 to move longitudinally along the rack 416 to permit printing on different lines or areas of the booklet 228. As the clamping frame 408 is moved longitudinally, the clamping frame 408 pulls the booklet 228 in a longitudinal direction away from the printer inlet 240. As the booklet 228 is moved away from the printer inlet 240, the booklet 228 slides longitudinally between the support plate 400, which is in its raised position with the posts 406 being extended, and the feeding rollers 284 and 286. The sliding action of the booklet 228 may cause one or both of the first and second feeding rollers 284 and 286 to rotate. In the second reader-printer embodiment, the first and second feeding rollers 284 and 286 freely rotate. Additionally or alternatively, one or both of the first and second feeding rollers 284 and 286 may be motorized to assist movement of the booklet 228 through the printer system 216 by pushing the booklet 228.

In the second reader-printer embodiment, sliding friction between the booklet 228 and the support plate 400 advantageously acts to straighten the booklet 228 at its printable area 440 during printing. The material of the support plate 400 at its top surface and the clamping pressure applied between the support plate 400 and the feeding rollers 284 and 286 may be optimized to provide adequate but not excessive sliding friction on the booklet 228.

In an alternative reader-printer embodiment (not shown), the support plate 400 may be implemented as a series of parallel, spaced apart rollers substantial in transverse alignment with the feeding rollers 284 and 286.

Figure 14:
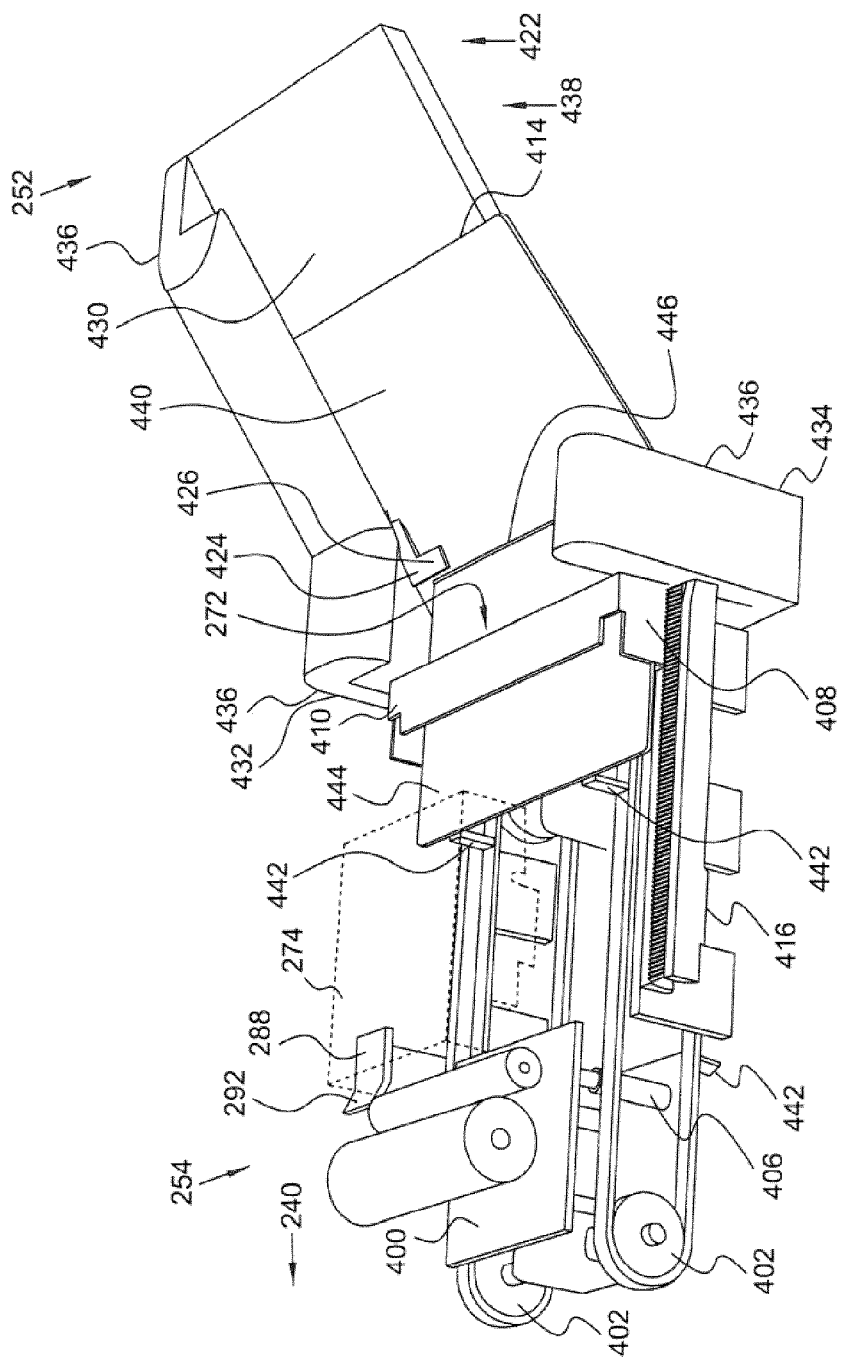
FIG. 14 is a perspective view of the transport system of FIG. 11, showing ejection of the booklet.

FIG. 14 shows the printer system 216 in a an ejection position for ejecting the booklet 228 following printing on the booklet 228 by the reader-printer 210. In such ejection position, the clamping frame 408 is located adjacent the exit ramp 418 and the stopper gate 272 (not directly visible in FIG. 14) is lowered. In the second reader-printer embodiment, the support plate 400 is lowered when the printer system 216 is in its ejection position, however, in general the support plate 400 may be in any vertical position when the printer system 216 is in its ejection position. The printer system 216 is operable to cause the push-plates 442 of the conveyors 402 to push the booklet 228 at its trailing edge 444 toward the printer outlet 252. In the second reader-printer embodiment, the printer system 216 is operable to cause the exit clamp 424 to clamp the booklet 228 at its side edge.

While FIG. 14 shows each exemplary push-plate 442 as being a linearly projecting plate, in general either or both push-plates 442 (and the push-plate 280 of the first reader-printer embodiment) may have any suitable shape, including extending arcuately, having a bend to form a lip at the end of the push-plate 442 distal from the conveyor 402, having a bend to form an L-shaped projection, other shapes, and any combination thereof for example.

The printer system 216 is preferably operable to cause the exit clamp 424 to clamp the booklet 228 proximate the binding 446 of the booklet 228 outside of the printing area of the booklet 228, thereby advantageously avoiding contact with recently printed areas of the booklet 228. In the second reader-printer embodiment, the printer system 216 is operable to cause the push-plates 442 to move longitudinally to a position which, based on the standard dimensions of a known booklet 228 type, places the binding 446 proximate the exit clamp 424. Additionally or alternatively, the printer system 216 includes in some reader-printer embodiments one or more sensors (not visible in FIG. 14) for detecting the leading edge 414 at an appropriate distance along the exit ramp 418 based on the standard dimensions of a known booklet 228 type. In some reader-printer embodiments, the printer system 216 is programmable with the dimensions of several booklet 228 types which can be selected by the user and/or detected by the reader-printer 210.

In the second reader-printer embodiment of the invention, each conveyor 402 may include a pair of push-plates 442 projecting from the conveyor 402 belt at opposite locations along the conveyor 402 belt, thereby advantageously providing a second push-plate 442 at a receiving position when the first push-plate 442 has completed its role in ejecting the booklet 228. However, in some reader-printer embodiments only one push-plate 442 is employed for each conveyor 402 belt. The printer system 216 may be operable to advance the conveyor 402 in one direction only, or the conveyor 402 may be reversible with the printer system 216 being operable to selectably advance the conveyor 402 in either opposing direction.

The reader-printer 210 according to the second reader-printer embodiment includes the edge bracket 288, which may include the cantilevered bracket section 292, as shown in FIG. 14. Variations in number, placement and shape of the edge bracket 288 are possible, and the edge brackets 288 of the first and second embodiments may be the same or different from each other, for example.

Third Reader-Printer Embodiment

Figure 15:
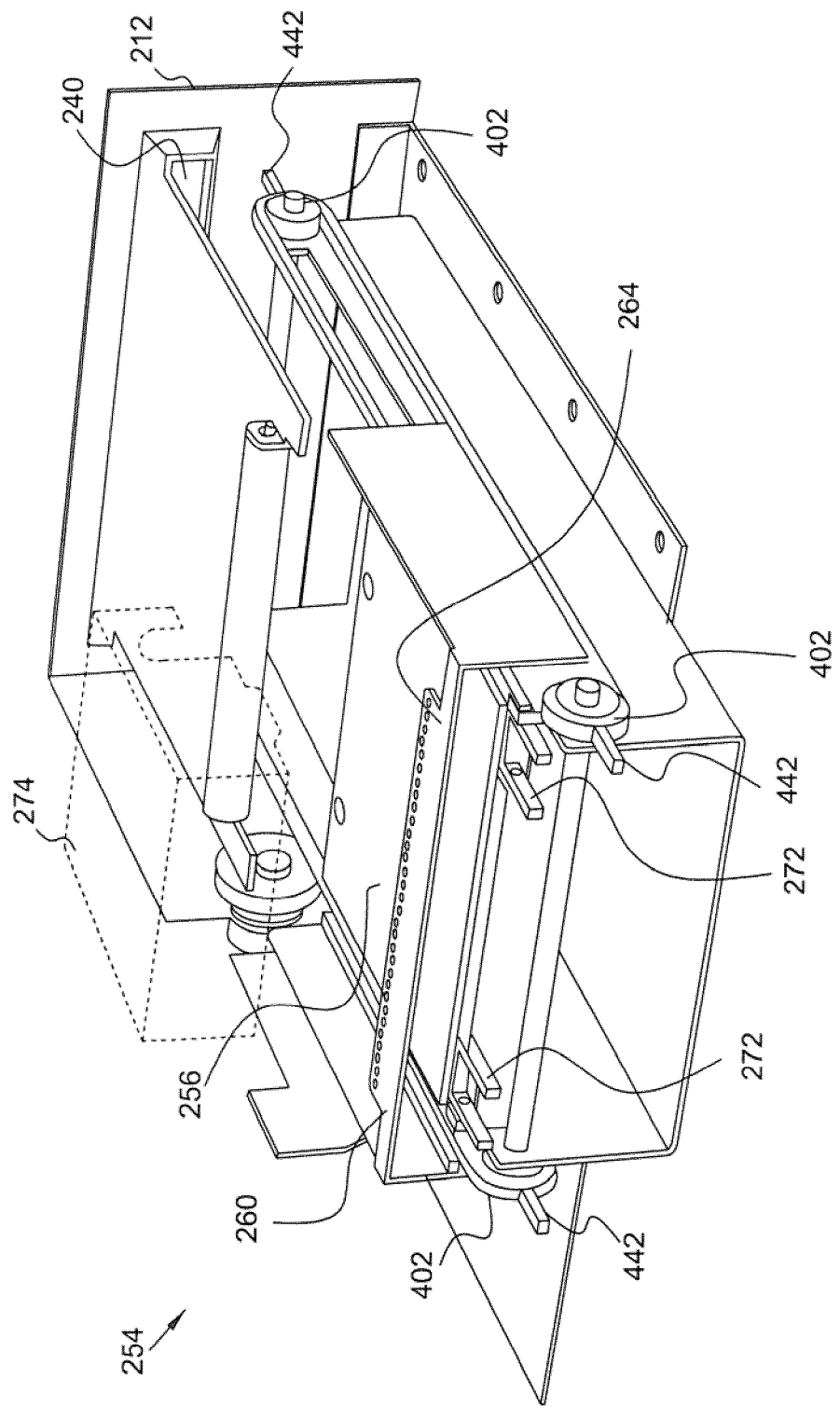
FIG. 15 is a perspective view of a portion of the integrated reader-printer of FIG. 7, showing the transport system in accordance with a third reader-printer embodiment of the invention.

Referring to FIG. 15, the transport system 254 in accordance with a third reader-printer embodiment of the invention includes one platen 256 which extends into the space defined within the transport frame 260, and includes a pair of parallel, spaced-apart conveyors 402 extending along opposing sides of the transport path. Two parallel, spaced-apart stopper gates 272 are also shown in FIG. 15.

The transport system 254 of the third embodiment is operable to receive the booklet 228 (not shown in FIG. 15) via the printer inlet 240. In variations, the transport system 254 of the third embodiment may be operable to release or eject the booklet 228 at the same or opposing end of the transport system 254 as the printer inlet 240, or the transport system 254 shown in FIG. 15 may be operable to release or eject the booklet 228 at both the same and opposing ends of the transport system 254 as the printer inlet 240. The transport system 254 shown in FIG. 15 may include the conveyor 296 (FIG. 10), the exit ramp 418 (FIGS. 11 to 14), the exit clamp 424 (FIGS. 11 to 14), or any combination thereof for example. In embodiments in which the transport system 254 is employed to receive and reverse eject or otherwise release the booklet 228 solely at the printer inlet 240, the transport system 254 need not include conveyors 402.

Generally, features described with respect to the first and second reader-printer embodiments are incorporated to the extent applicable into the third reader-printer embodiment.

Fourth Embodiment of Reader-Printer Apparatus

Referring to FIGS. 16 to 24, a further variation of the transport system 254 of the reader-printer 210 (FIG. 7) in accordance with a fourth reader-printer embodiment of the invention is shown. The transport system 254 of the fourth reader-printer embodiment includes a platen 256 which extends longitudinally into the space defined within the transport frame 260 below the upper frame plate 264. The transport system 254 of the fourth reader-printer embodiment is operable to both receive and release an object, such as the booklet 228 (not shown in FIGS. 16 to 24), at the printer inlet 240, such that in the fourth reader-printer embodiment the printer outlet 252 coincides with the printer inlet 240. In the fourth reader-printer embodiment, the transport system 254 need not include a transport conveyor, push-plate, exit conveyor nor an exit ramp.

While FIGS. 16 to 24 do not show the booklet 228 for improved clarity of viewing corresponding transport system 254 features, reference made herein to the booklet 228, its leading edge 414, trailing edge 444, and/or binding 446 is reference to such booklet 228 features when present in association with the transport system 254.

Figure 21:
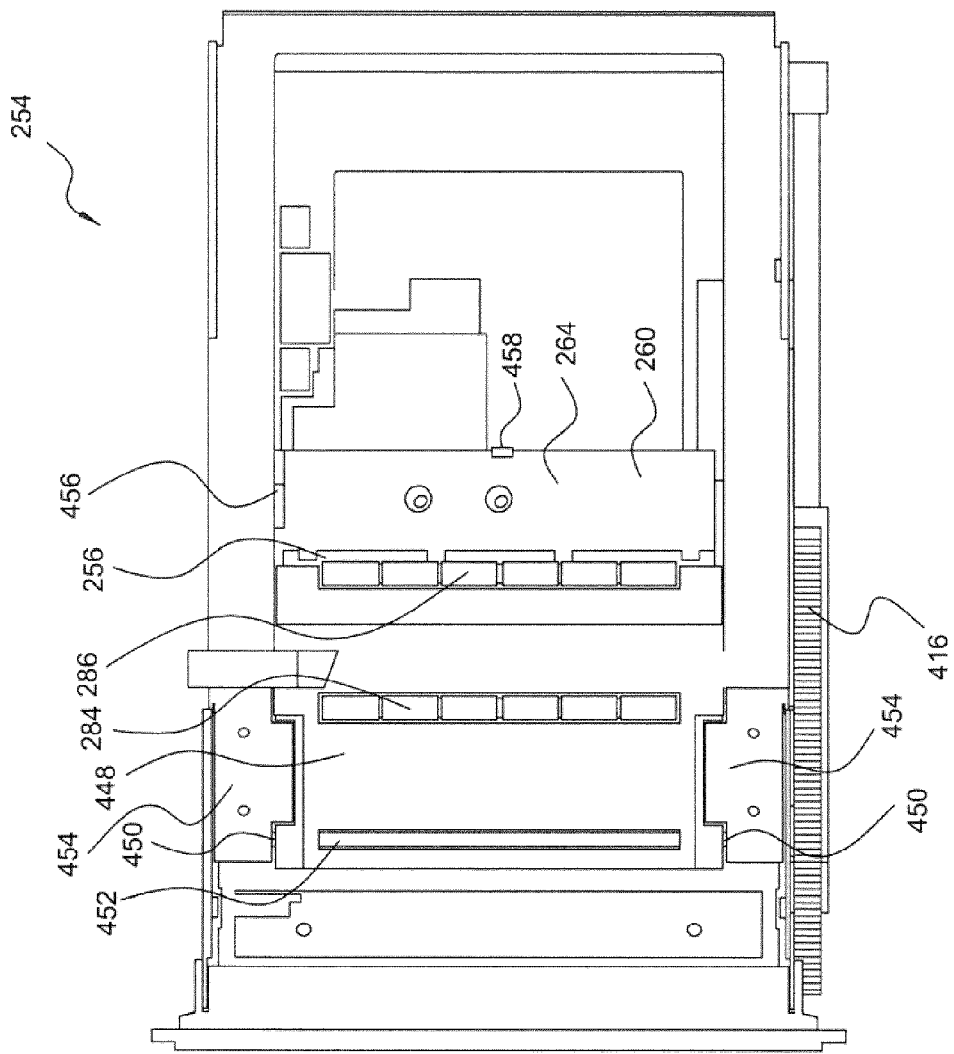
FIG. 21 is a top view of the transport system of FIG. 16, showing a print-start position of the printer system.

In the fourth reader-printer embodiment, the transport system 254 includes an entrance feeder 448 which is rotatably coupled to the remainder of the transport system 254 at a hinge connection 450. The axle 452 of the hinge connection 450 is best seen in FIG. 21. Also visible in FIG. 21 are the first and second feeding rollers 284 and 286. In the fourth reader-printer embodiment, each of the first and second feeding rollers 284 and 286 are made of a set of axially aligned roller members typically all of the same size. The first feeding roller 284 is closer to the printer inlet 240 than the second feeding roller 286. As best seen in FIG. 21, the first and second feeding rollers 284 and 286 generally have the same size and transverse length as each other. The first and second feeding rollers 284 and 286 of the fourth reader-printer embodiment are dimensioned to avoid contact with the booklet 228 near the side edges of the booklet 228. The transport system 254 of the fourth reader-printer embodiment includes an entrance feeder stopper 454 which limits upward rotation of the entrance feeder 448.

Figure 16:
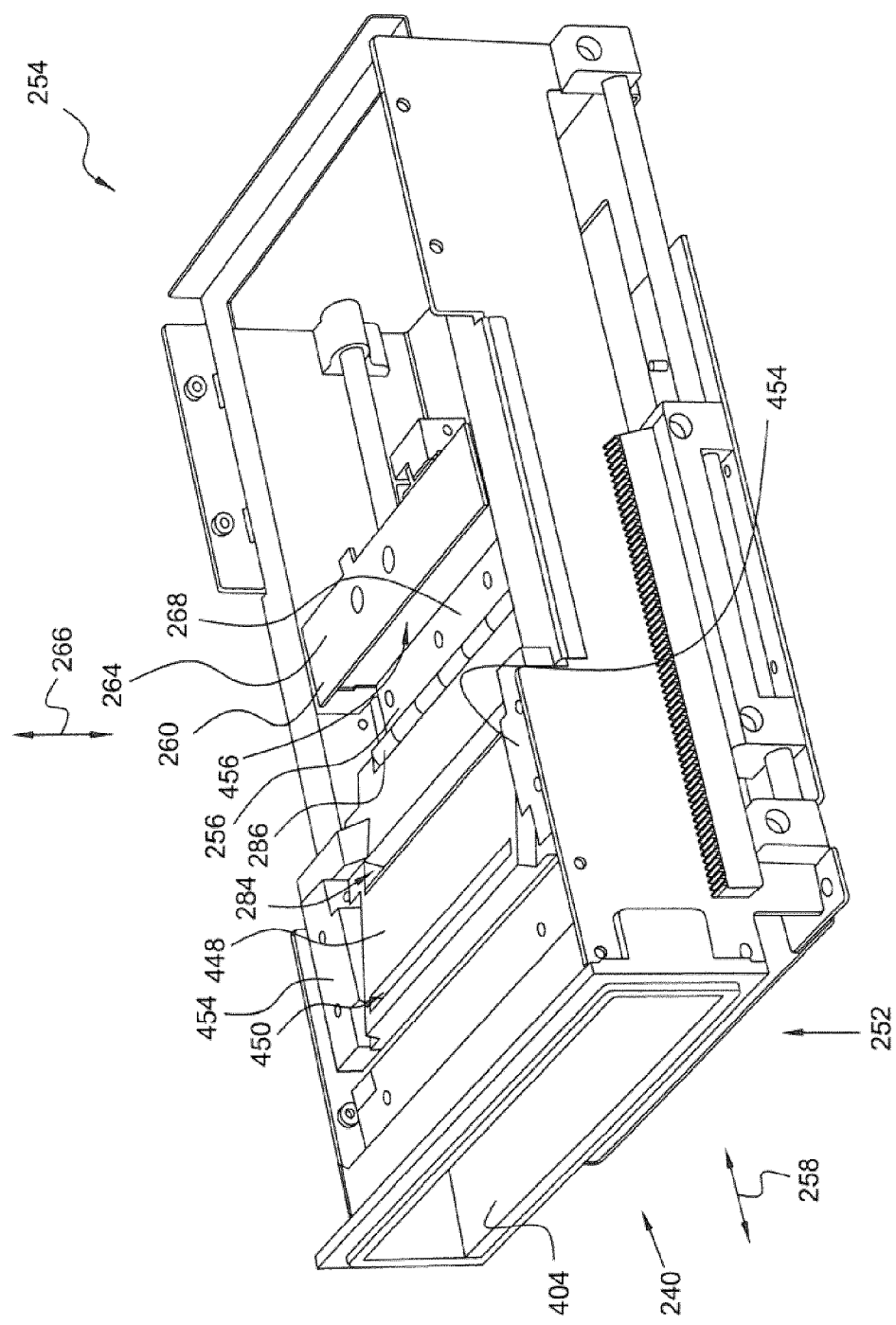
FIG. 16 is a perspective view of a portion of the integrated reader-printer of FIG. 7 when a printer system is in its receiving position, showing the transport system in accordance with a fourth embodiment of the invention.
Figure 17:
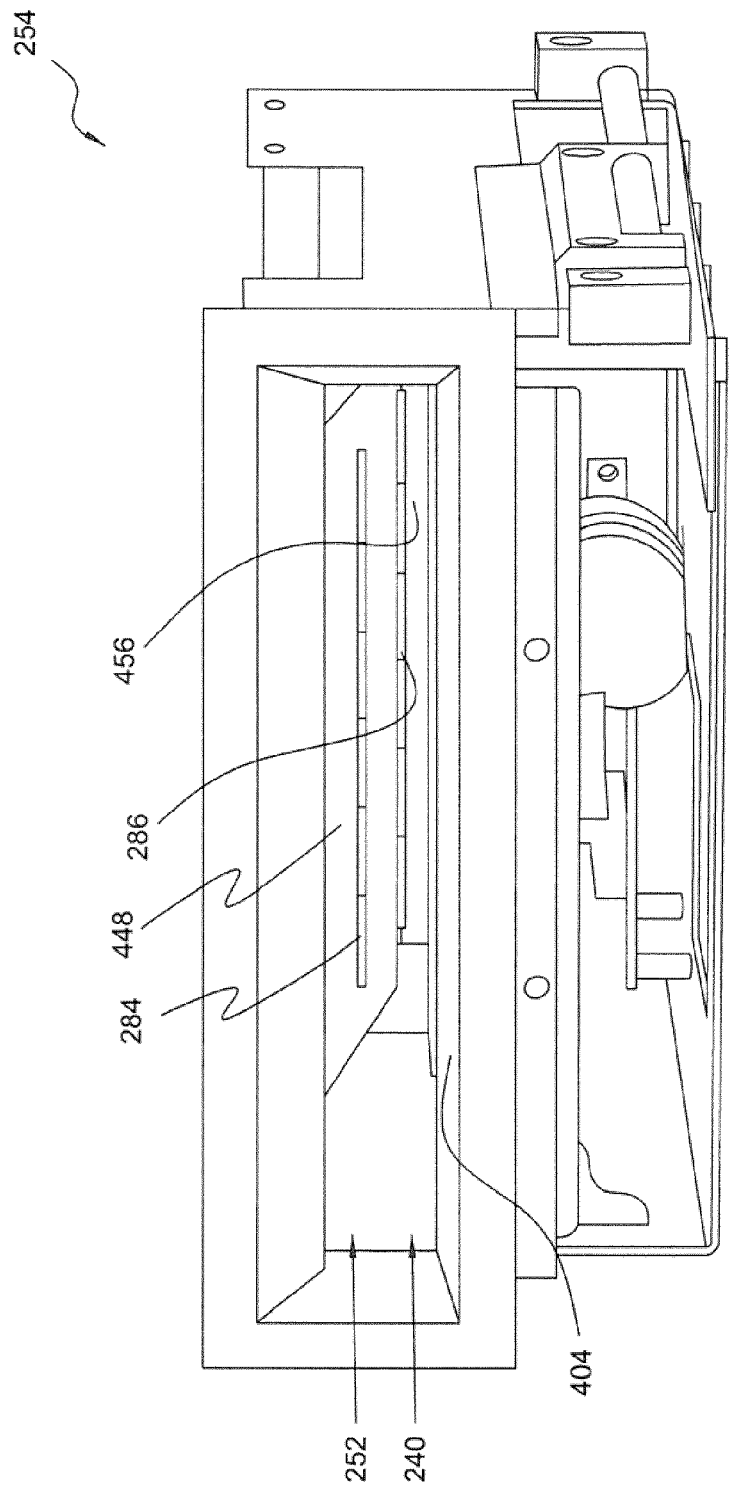
FIG. 17 is a frontal-perspective view of the transport system of FIG. 16, showing the platen and a lower inlet guide.

Referring to FIGS. 16 and 17, the printer system 216 (FIG. 2) of the fourth reader-printer embodiment is shown in its receiving position in which the reader-printer 210 is operable to receive the booklet 228 when the user inserts the booklet 228 at the printer inlet 240 into the reader-printer 210 in the longitudinal direction 258.

When the printer system 216 is in the receiving position, the platen 256 is in its lowered position in which the top surface of the platen 256 is approximately aligned with that of the lower inlet guide 404. Also when the printer system 216 is in the receiving position, the entrance feeder 448 is rotatably released to permit the entrance feeder 448 to lower, such as by force of gravity, until reaching a limit of downward rotation. In the fourth reader-printer embodiment, the hinge connection 450 limits the downward rotation of the entrance feeder 448. In general, however, the transport system 254 may include any suitable mechanism for limiting the downward rotation of the entrance feeder 448, including having a mechanical stopper, an electromechanical stopper, a hinge connection 450 being electromechanical, an adjustable stopper, other techniques or any combination thereof. In some reader-printer embodiments, the downward rotation of the entrance feeder 448 is limited by contact between the entrance feeder 448 and the platen 256, such as by the second feeding roller 286 contacting the platen 256.

In some reader-printer embodiments, the printer system 216 includes one or more entrance sensors (not visible in FIGS. 16 and 17) for sensing the presence of a booklet 228 entering the printer inlet 240. The entrance sensor may be any suitable sensor such as a laser, LED, microwave or infrared presence sensor, motion detector, proximity detector, similar detection sensor, ultra-sound sensor, mechanical sensor, or any combination thereof for example. By way of particular example, mechanical pressure against the entrance feeder 448 may be sensed by the entrance sensor. In reader-printer embodiments having an entrance sensor, the printer system 216 may be operable to bring itself into the receiving position upon sensing the insertion of a booklet 228 into the printer inlet 240 or otherwise sensing the presence of an object at or near the printer inlet 240. Bringing the printer system 216 into the receiving position may involve moving the platen 256 and/or the transport frame 260 longitudinally, moving the platen 256 in the vertical direction 266, rotating the entrance feeder 448, releasing the entrance feeder 448 so as to permit rotation of the entrance feeder 448, other actions of the transport system 254, or any combination thereof for example. By way of particular example, the transport system 254 is operable in some reader-printer embodiments to lower the platen 256 in response to sensing the presence of an object at the printer inlet 240 so as to permit the object to be further inserted via the printer inlet 240 above the platen 256 toward the transport frame 260.

The transport frame 260 of the fourth reader-printer embodiment includes a backstop 456 for preventing the booklet 228 from being pushed past the transport frame 260, and the printer system 216 includes a backstop 456 sensor (not directly visible in the Figures) for sensing the presence of the leading edge 414 (not shown in FIGS. 16 to 24) of the booklet 228 being adjacent or otherwise proximate to the backstop 456. The backstop 456 sensor may be any suitable sensor such as a laser, LED, microwave or infrared presence sensor, motion detector, proximity detector, similar detection sensor, ultra-sound sensor, mechanical sensor, or any combination thereof for example. By way of particular example, the backstop 456 may be resiliently coupled to the transport frame 260 by a backstop spring 458 (FIG. 21) such that mechanical pressure of the leading edge 414 of the booklet 228 pressing against the backstop 456 is sensed by the backstop 456 sensor (e.g. by an electrical contact of the backstop 456 sensor closing).

Figure 18:
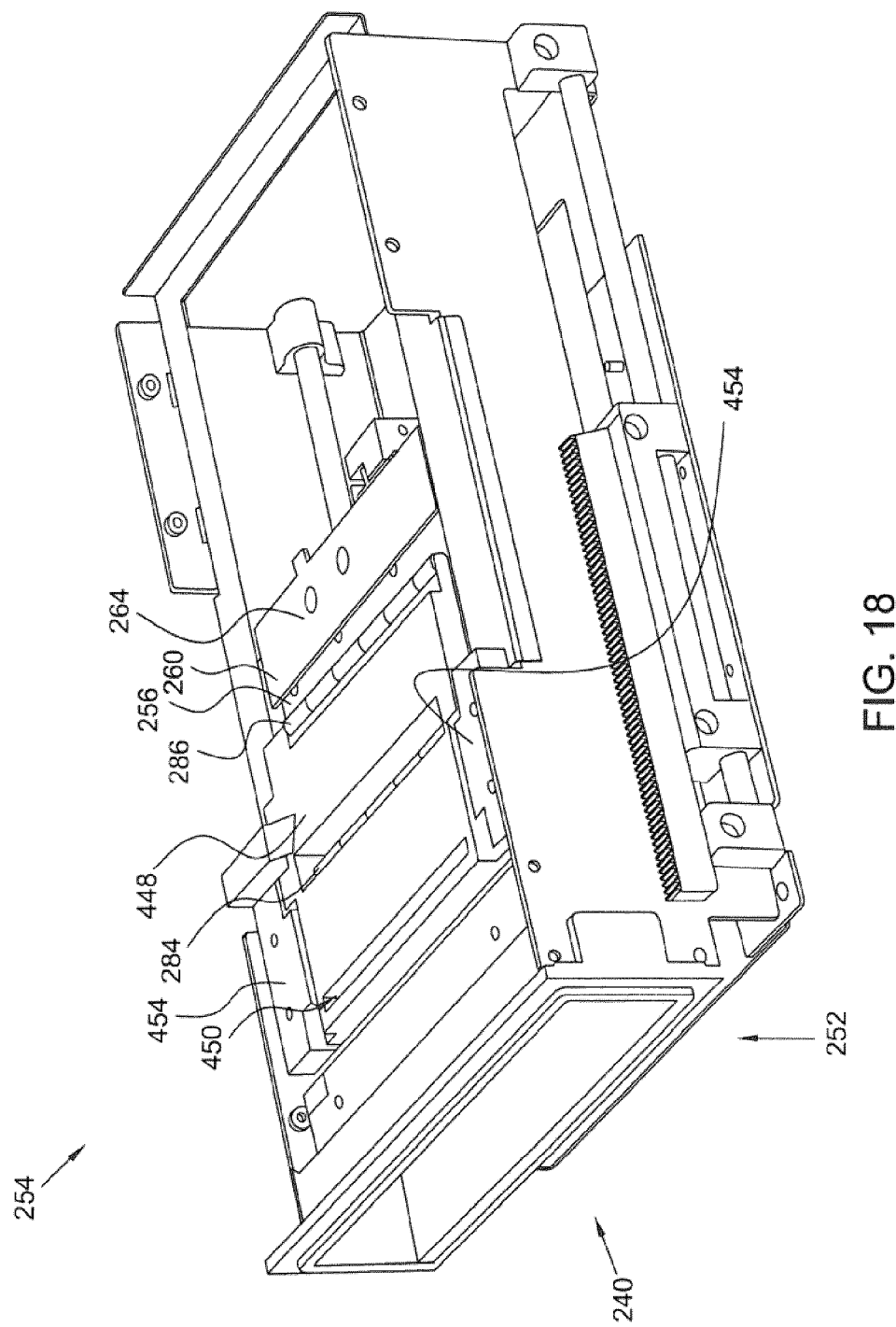
FIG. 18 is a perspective view of the transport system of FIG. 16, showing a received position of the printer system.
Figure 19:
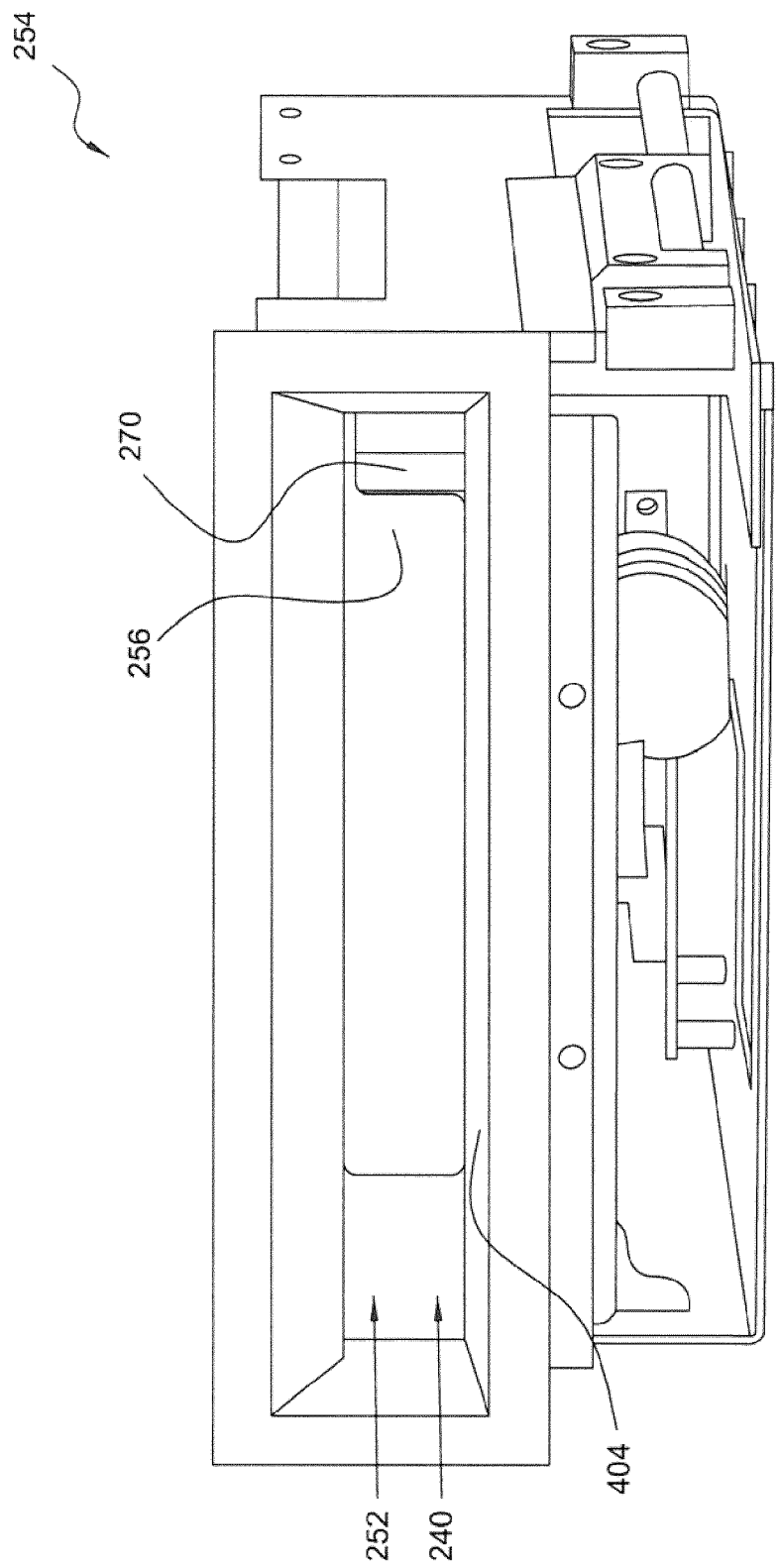
FIG. 19 is a frontal-perspective view of the transport system of FIG. 18, showing a platen post.

Referring to FIGS. 18 and 19, the printer system 216 is operable to move to its received position in response to detecting the presence of an object (e.g. the leading edge 414 of the booklet 228) in proximity to the backstop 456. In the received position shown in FIGS. 18 and 19, the distal end 268 (FIG. 16) of the platen 256 is clamped against the upper frame plate 264. In ordinary use, the leading edge 414 is typically clamped by the transport frame 260 between the platen 256 and the upper frame plate 264 when the printer system 216 is in its received position. In the fourth reader-printer embodiment, clamping the leading edge 414 involves raising the platen 256 until clamping occurs. In the fourth reader-printer embodiment, the platen 256 is raised by effecting vertical movement of platen posts 270, as best seen in FIG. 19. In general, however, any suitable mechanism for effecting movement of the platen 256 relative to the upper frame plate 264 may be employed. In typical circumstances, raising the platen 256 ordinarily causes the entrance feeder 448 to rotate upwardly. In the fourth reader-printer embodiment, the entrance feeder 448 is operable to rotate freely within its limits under the force of gravity such that the second feeding roller 286 and possibly also the first feeding roller 284 make contact with the booklet 228 by resting on non-edge areas of the booklet 228. In some reader-printer embodiments, however, the transport system 254 is operable to cause the entrance feeder 448 to exert a downward clamping force on non-edge areas of the booklet 228.

Figure 20:
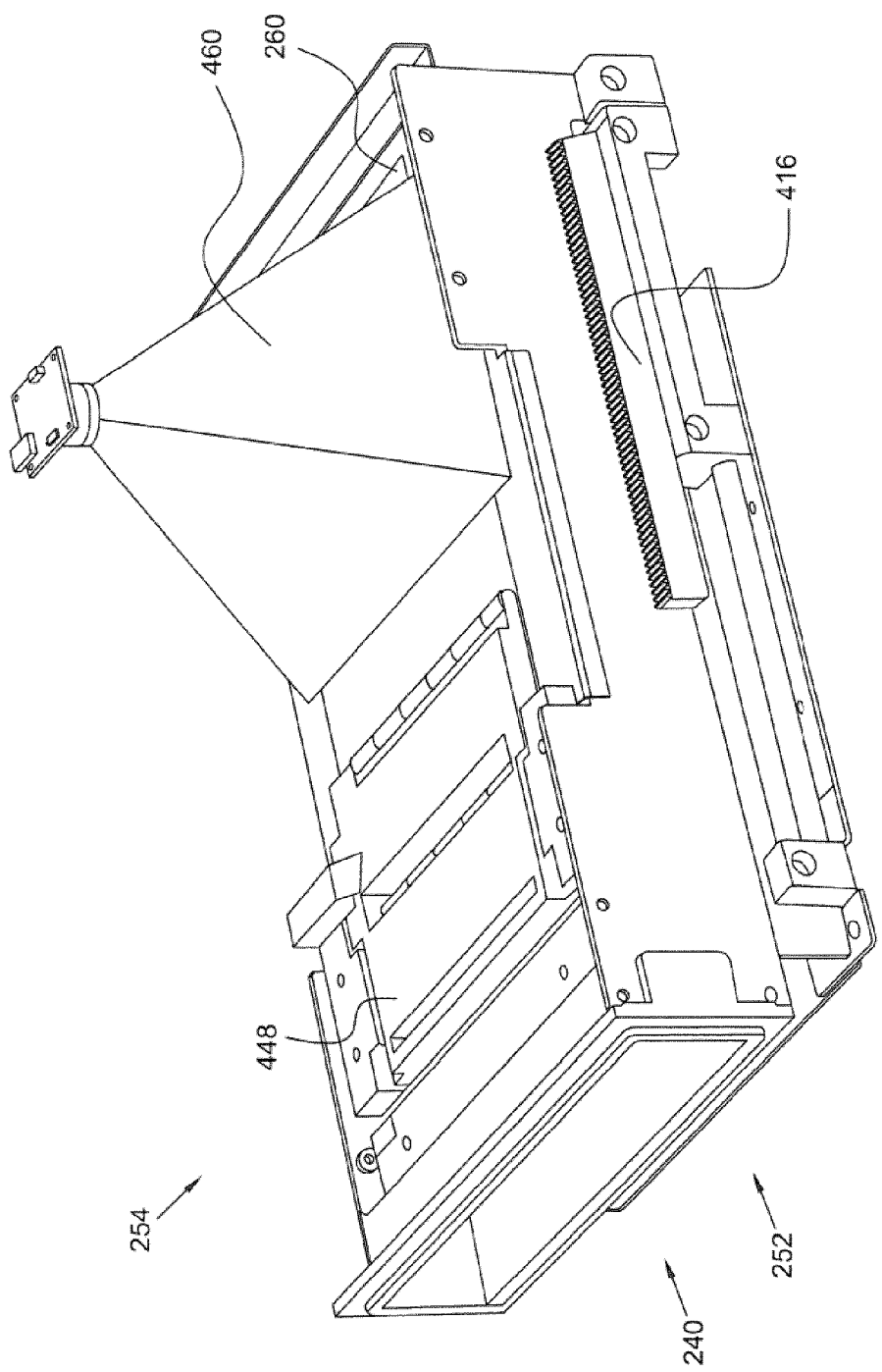
FIG. 20 is a perspective view of the transport system of FIG. 16, showing an imaging position of the printer system and an imaging device.

Referring to FIG. 20, the transport system 254 is shown when the printer system 216 is in its imaging position. The reader-printer 210 of at least the fourth reader-printer embodiment includes an imaging system having an imaging device 460, which may be a camera for example.

When the printer system 216 is in its imaging position, the transport system 254 is preferably positioned so that the printable area 440 (not visible in FIGS. 16 to 24) of the booklet 228 is within the field of view of the imaging device 460. In some reader-printer embodiments employing the imaging device 460, the reader-printer 210 is operable to display images of the printable area 440 produced by the imaging device 460 on the reader-printer display 222 for viewing by the user. Additionally or alternatively, machine-vision processes may be employed to conduct automated image analysis of the printable area 440, or portions thereof. In variations, the imaging device 460 may be operable to produce still images, video images, or both still and video images. In some reader-printer embodiments, the imaging device 460 is operable to produce lighting when producing images.

In some reader-printer embodiments, the reader-printer 210 is operable to receive user input indicating a sub-area of the printable area 440 upon which printing should occur, typically in response to presenting images of the printable area 440 on the reader-printer display 222. By way of example in the case of a touch screen reader-printer display 222, the user may be permitted to indicate a desired location for printing by touching the touch-screen at a location thereof corresponding to the user's desired location when the touch-screen reader-printer display 222 is displaying the printable area 440.

The printer system 216 of the fourth reader-printer embodiment is operable to cause the platen 256 and the transport frame 260 to move together longitudinally from the received position to the imaging position after fully clamping the booklet 228. In the fourth reader-printer embodiment, the platen 256 and the transport frame 260 move longitudinally with longitudinal movement of the rail or rack 416 via a motor-driven pinion gear (not shown). In general, any suitable linear motion system may be employed.

FIG. 21 shows the printer system 216 in a print-start position for printing on the booklet 228. In such print-start position, the portion of the printable area 440 closest to the leading edge 414 of the booklet 228 is positioned between the second feeding roller 286 and the upper frame plate 264. For clarity of illustration, the booklet 228 is not shown in FIG. 21, thereby showing the portion of the platen 256 corresponding to the exposed printable area 440 when the printer system 216 is in its print-start position. In accordance with the fourth and other reader-printer embodiments, the second feeding roller 286 contacts the booket 228 at a distance from the leading edge 414 and the upper frame plate 264. While not shown in FIG. 21, the printhead 274 is positioned to print on a printing line within the exposed portion of the printable area 440.

Figure 22:
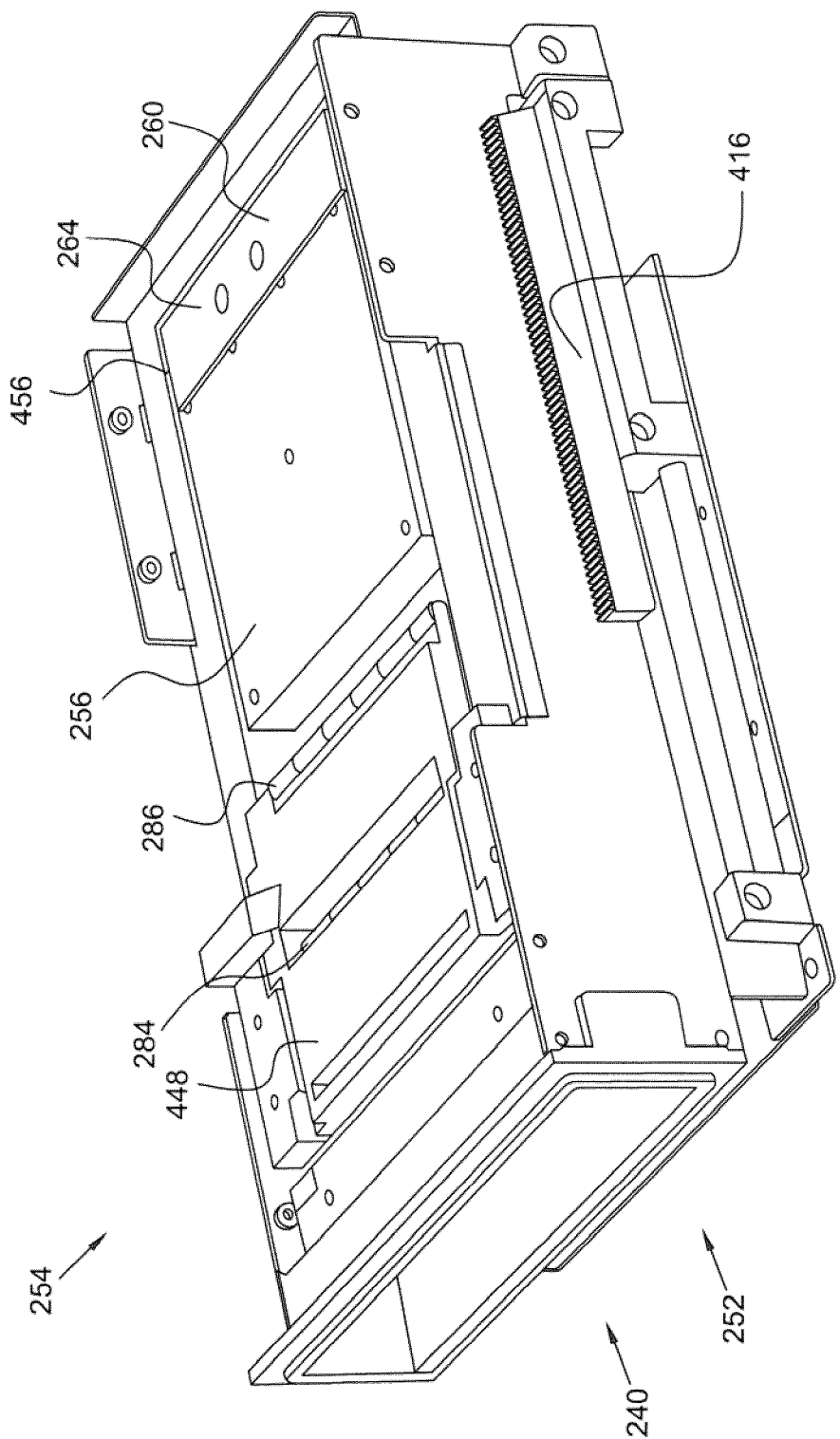
FIG. 22 is a perspective view of the transport system of FIG. 16, showing a printed position of the printer system.

FIG. 22 shows the printer system 216 in a printed position in which the portion of the printable area 440 closest to the trailing edge 444 of the booklet 228 is the portion of the printable area 440 closest to being directly beneath the printhead 274 (not shown).

Referring to FIGS. 21 and 22, the printer system 216 of the fourth reader-printer embodiment is operable to cause the platen 256 and the transport frame 260 to move together in the longitudinal direction away from the print-start position toward the printed position while the printhead 274 is employed to print on the booklet 228 at any desired location within its printable area 440. The printing position of the printer system 216 extends from the print-start position to the printed position. In some reader-printer embodiments, the printer system 216 is placed in its print-start position before printing on the booklet 228 regardless of where printing will take place, thereby advantageously registering the position of the booklet 228 relative to the printhead 274 at the print-start position. In some reader-printer embodiments, however, the printer system 216 is moved from its imaging position only to the point along the printing position where printing begins, thereby advantageously minimizing longitudinal movement of the platen 256 and the transport frame 260. The printhead 274 of the fourth reader-printer embodiment may be similar to or different from that of any of the first to third reader-printer embodiments or any combination thereof, for example. In the fourth reader-printer embodiment the first and second feeding rollers 284 and 286 and the hinge connection 450 are operable to rotate freely as the booklet 228 is pulled by its leading edge 414 as the printer system 216 moves from its print-start to its printed position, thereby advantageously applying gravitationally induced downward pressure on non-edge areas of the booklet 228 during printing. In variations, any one or more of the first and second feeding rollers 284 and 286 and the hinge connection may be motorized, for example.

Figure 23:
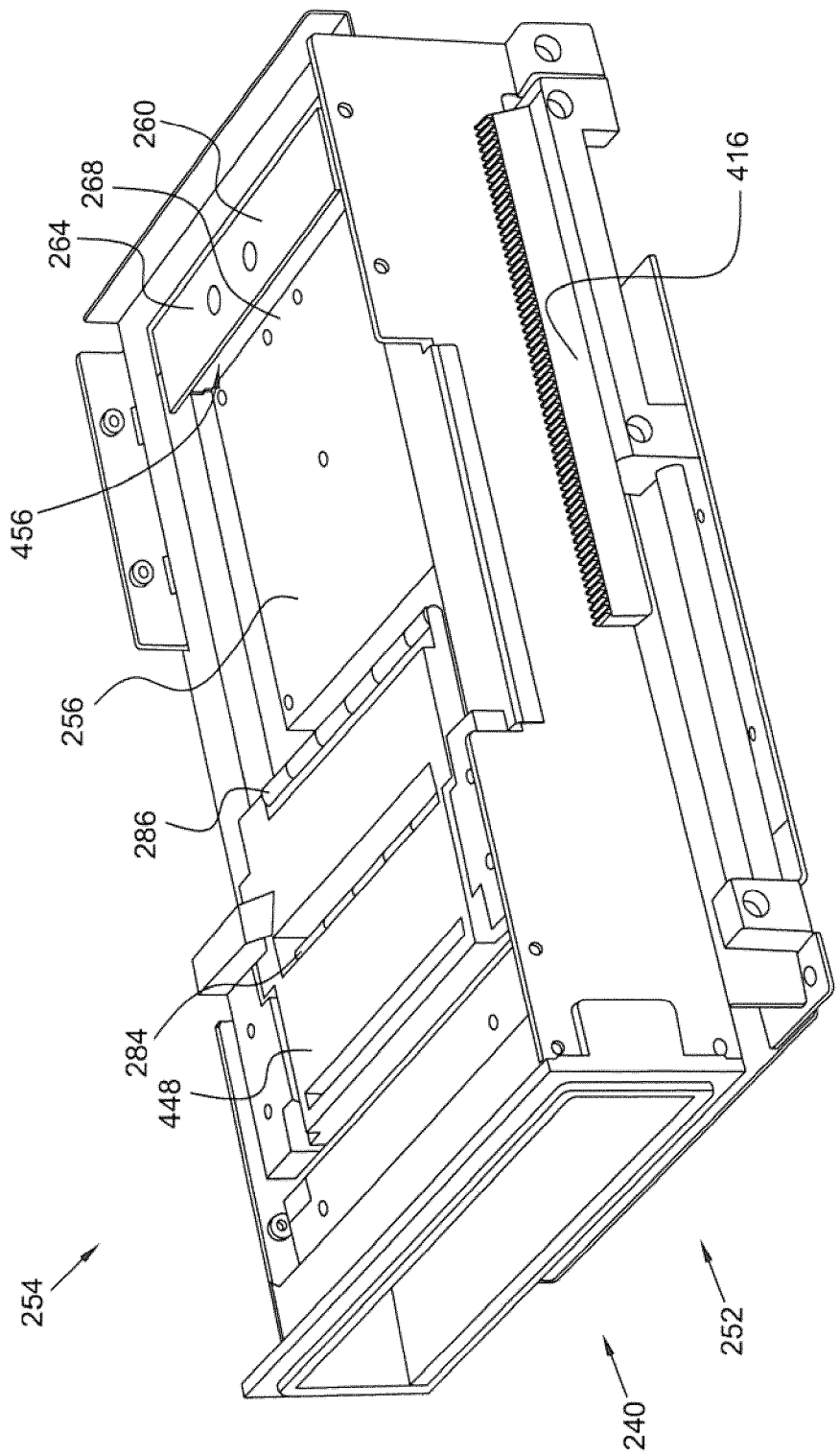
FIG. 23 is a perspective view of the transport system of FIG. 16, showing a released position of the printer system.

FIG. 23 shows the printer system in its released position. In the fourth reader-printer embodiment, the longitudinal position of the platen 256 and the transport frame 260 when the printer system 216 is in its released position is generally the same as when the printer system 216 is in its printed position. In the released position, the platen 256 is lowered sufficiently to release the booklet 228 from clamping. Additionally, the entrance feeder 448 is rotated upwardly so as to advantageously avoid contact with recently printed areas of the booklet 228 when the printer system 216 is moved from its released position to its ejection position shown in FIG. 24. Rotating the entrance feeder 448 upwardly may be effected by any suitable mechanism, including having a solenoid-driven or other electromagnetic plunger, the hinge connection 450 being electromechanical, an adjustable plunger, other techniques or any combination thereof for example.

Figure 24:
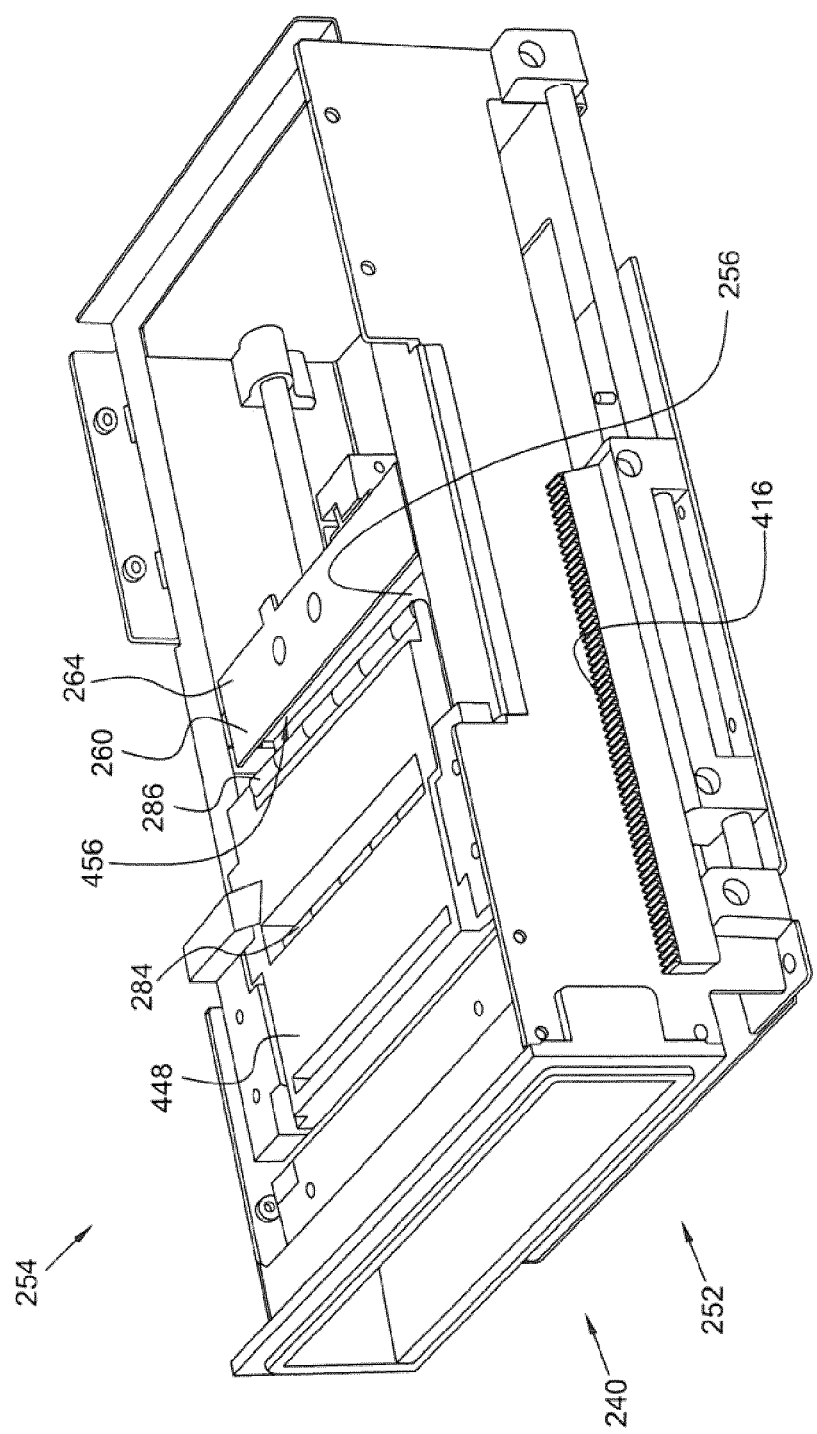
FIG. 24 is a perspective view of the transport system of FIG. 16, showing an ejection position of the printer system.

Still referring to FIG. 24, the platen 256 and the transport frame 260 are moved longitudinally toward the entrance feeder 448 so as to permit the user (not shown) to grasp the booklet 228 at its trailing edge 444 (not shown in FIGS. 16 to 24) and pull the booklet 228 through the printer outlet 252 and out of the reader-printer 210. In some reader-printer embodiments, the printer system 216 includes one or more ejection sensors (not shown) for sensing the removal of the booklet 228 from the transport system 254. The ejection sensors may be of any suitable type, including being the same type, and even possibly the same sensors, as the entrance sensors for example. In reader-printer embodiments having the ejection sensors, the printer system 216 may be operable to release the entrance feeder 448 to permit the entrance feeder to lower under force of gravity upon sensing removal of the booklet 228. Additionally or alternatively, the printer system 216 may be operable to permit or force the platen 256 to rise upon sensing removal of the booklet 228. In some reader-printer embodiments, the printer system 216 is operable to move to the receiving position (FIGS. 16 and 17) upon sensing removal of the booklet 228. In some reader-printer embodiments, the ejection position and the receiving position of the printer system 216 coincide with each other.

While the first and second rollers 284 and 286 are specifically described and illustrated herein with respect to the first and second reader-printer embodiments and the entrance feeder 448 is specifically described herein with respect to the fourth reader-printer embodiment, any of the first roller 284, second roller 286 and the entrance feeder 448 in any combination may be suitably employed in any reader-printer embodiments, including the third reader-printer embodiment for example.

In some embodiments, the transport system 254 of the reader-printer 210 in accordance with any one reader-printer embodiment, or in accordance with a combination of reader-printer embodiments, is operable to perform transport functions associated with the security checkpoint 10.

System of Modules

Figure 25:
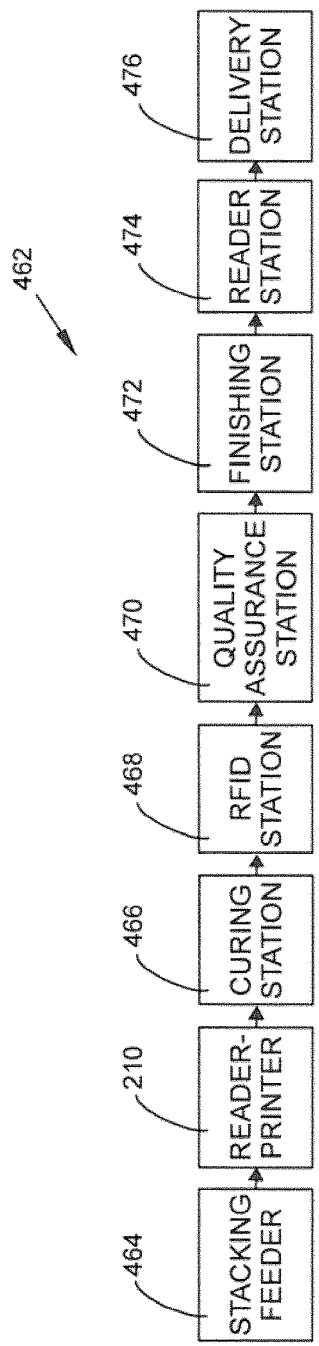
FIG. 25 is a block diagram of a modular system incorporating the integrated reader-printer of FIG. 7, showing additional modules.

Referring to FIG. 25, the reader-printer 210 may form part of a modular system 448 for processing value items such as the booklet 228. In addition to the reader-printer 210, the modular system 448 may include any one or more of the following additional modules:

(a) a stacking feeder 450 for feeding booklets 228, including blank booklets 228 and sheet-like documents, to the reader-printer 210;

(b) a curing station 452 for curing the booklets 228, such as by permitting ink or any other chemical and/or organic substance printed on the booklet 228 by the reader-printer 210 to dry or otherwise cure, including permitting the ink or other substance to dry or cure in a temperature and/or humidity controlled environment;

(c) a RFID station 454 for initializing hardware components attached to or forming part of the booklet 228 that are associated with RFID (Radio-Frequency Identification) technology, or otherwise performing RFID-related processing tasks;

(d) a quality assurance station 456 for performing quality assurance processes, such as producing an image of the printed booklet 228 and performing automated image processing or other fault detection processes;

(e) a finishing station 458 for effecting final processes of the booklet 228, such as laminating one or more pages of the booklet 228, perforating the booklet 228 such as by laser perforation, any other finishing process, or any combination thereof;

(f) a reader station 460 for reading a newly issued booklet 228 and generating a security signature and storing the security signature for future authentications of the booklet 228, including possibly storing the security signature in a RFID chip attached to or forming part of the booklet 228; and (g) a delivery station 462 for receiving, including possibly stacking, completed booklets 228 in preparation for delivery.

In various reader-printer embodiments, the module immediately following the reader-printer 210 (e.g. the curing station 452) may receive booklets 228 from the reader-printer 210 via the printer outlet 252 disposed at the rear side of the reader-printer housing 212. Additionally or alternatively, such module may receive booklets 228 via the printer outlet 252 disposed at the top of the reader-printer housing 212.

In general, any two or more of the modules 450 to 462 of the modular system 448 may be interconnectable, including interconnecting the reader-printer 210 at its printer inlet 240 and/or its printer outlet 252 to any module 450 to 462 of the modular system 448. For example, the stacking feeder 450 and the reader-printer 210 may be dimensioned for being connected to each other proximate the printer inlet 240. By way of further example, the reader-printer 210 and the curing station 452 may be dimensioned for being connected to each other proximate the printer outlet 252. In some reader-printer embodiments, the reader-printer 210 is operable to eject booklets 228 directly into the delivery station 462 for delivery, including possibly stacking. In general, the reader-printer 210 and any number and selection of the modules 450 to 462 may be configured in any order. Whether or not interconnected with one or more modules 450 to 462, the reader-printer 210 may be configured as the integrated reader-printer 10, or as the printer-only version with the reader system 214 removed therefrom.

The reader station 460 may be dimensioned to receive the booklet 228 from the reader-printer 210 or any one of the other modules 450 to 458 and 462, including receiving the booklet 228 by automated devices. The reader station 460 may include an enclosure (not shown) such that the booklet 228 is received within the enclosure (not shown). The reader station 460 may include sources of electromagnetic radiation operable to produce laser radiation, x-ray radiation, ultraviolet radiation, visible light radiation, infrared radiation, other radiation, and any combination thereof for example.

In addition to the modules described herein above, the reader-printer 210 may be operated within a controlled environment, such as a temperature and/or humidity controlled environment. In some embodiments, the reader-printer 210 may be operable to control its environment, such as by communicating environmental control signals to an external module (not shown) for heating, ventilation and/or air conditioning (HVAC). In embodiments in which the reader-printer 210 is operable to measure its internal environment, the reader-printer 210 may be operable to communicate the measurements to the external HVAC module (not shown).

Thus, there is provided an apparatus for reading and printing on an object, the apparatus comprising: (a) a reader system for reading the object to obtain a digital signature representing a unique feature of the object; and (b) a printer system for printing on the object if the digital signature matches a reference digital signature associated with the object.

Method of Operation of Reader-Printer

Figure 26:
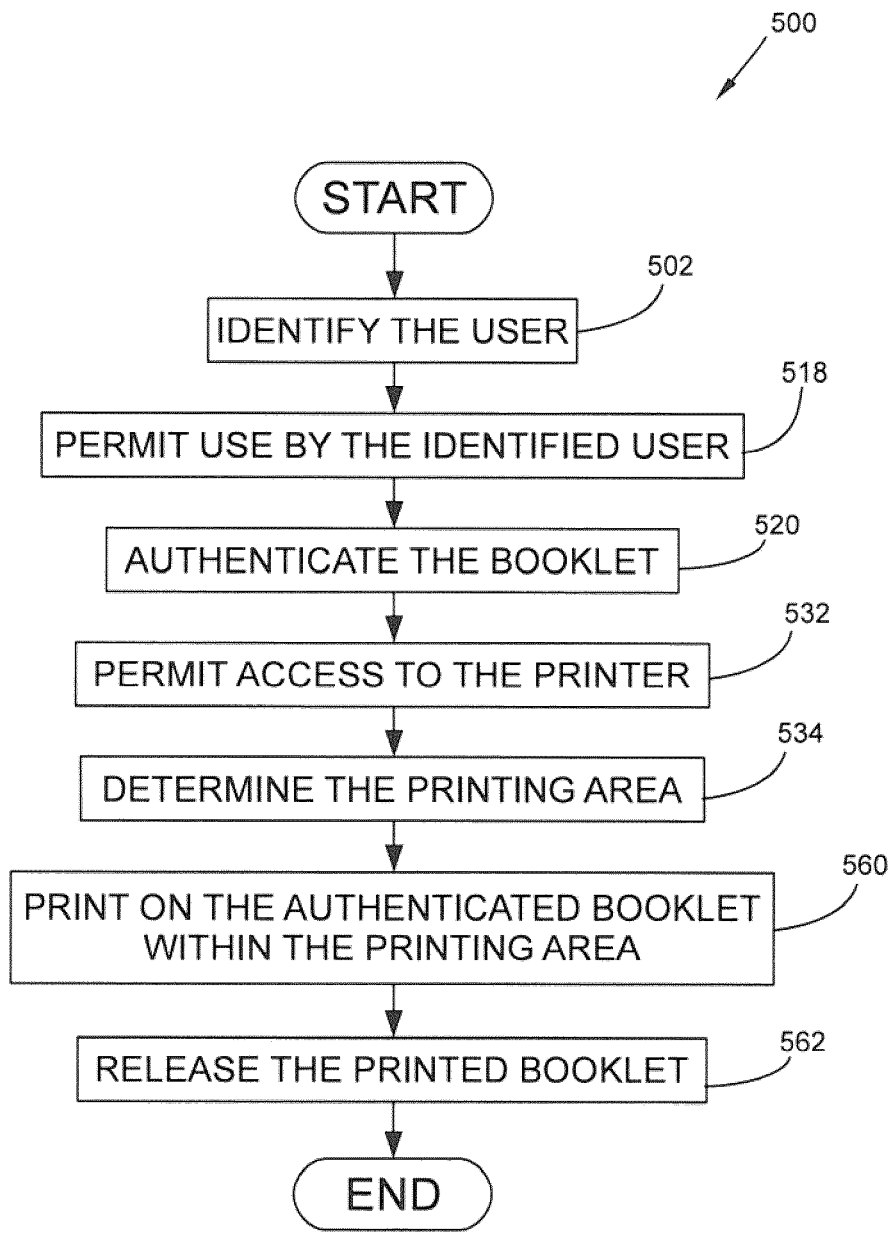
FIG. 26 is a flow diagram showing a method of authenticating and printing on a booklet in accordance with the first to fourth reader-printer embodiments of the invention.

Referring to FIG. 26, the reader-printer memory 246 (FIG. 8) of the reader-printer 210 in accordance with reader-printer embodiments, including the first to fourth reader-printer embodiments, of the invention contains blocks of code comprising computer executable instructions for directing the reader-printer processor 244 (FIG. 8) to perform the method shown generally at 500. Additionally or alternatively, such blocks of code may form part of a computer program product comprising computer executable instructions embodied in a signal bearing medium, which may be a recordable computer readable medium or a signal transmission type medium, for example.

When electrical power is being supplied to the reader-printer processor 244 and the read-printer memory 246, the reader-printer processor 244 is directed to begin executing the instructions of block 502.

Block 502 directs the reader-printer processor 244 to cause the reader-printer 210 to identify the user.

Figure 27:
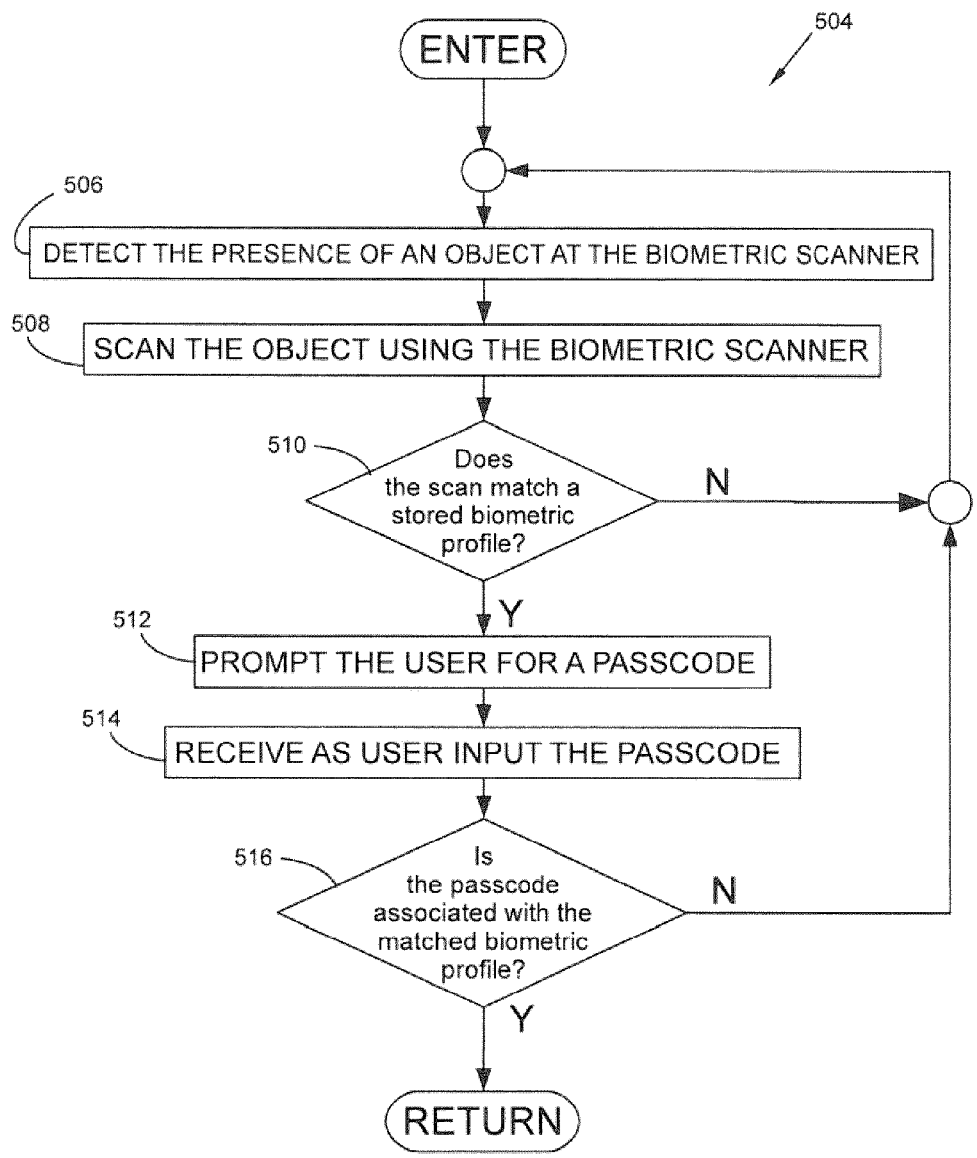
FIG. 27 is a flow diagram showing the method of FIG. 26 for identifying the user.

FIG. 27 shows an exemplary method 504 for executing the block 502 (FIG. 26) in accordance with reader-printer embodiments of the invention. The method 504 begins by executing block 506.

Block 506 directs the reader-printer processor 244 to detect the presence of an object at the biometric scanner 220 (FIG. 7). Detecting the presence of an object at the biometric scanner 220 may involve receiving by the reader-printer processor 244 a sensor output from a presence sensor (not shown in the Figures), such as a laser, microwave or infrared presence sensor, motion detector, similar detection sensor, or any combination thereof for example. Additionally or alternatively, detecting the presence of an object at the biometric scanner 220 may involve receiving a signal from a button or key of the reader-printer 210, such as one of the pushbuttons 226 (FIG. 7) or similar. After block 506 has been executed, the reader-printer processor 244 is directed to execute block 508.

Block 508 directs the reader-printer processor 244 to cause the biometric scanner 220 to perform a biometric scan to produce scan results. Scanning the object by the biometric scanner 220 may involve causing the biometric scanner 220 to scan for objects at the biometric scanner window 218.

Block 510 then directs the reader-printer processor 244 to determine whether the scan results obtained by block 508 matches a stored biometric profile. For example, the biometric scanner 220 may be a fingerprint scanner for producing a scanned fingerprint, and the stored biometric profiles may be previously scanned fingerprints of authorized users.

If the scan results do not match a stored biometric profile, then the reader-printer processor 244 is directed to return to block 506. In various reader-printer embodiments, an error message may also be displayed, the failed attempt may be logged, and other error processing functions may be performed.

If the scan results match a stored biometric profile, then the reader-printer processor 244 is directed to execute block 512.

Block 512 directs the reader-printer processor 244 to prompt the user for a passcode. In general, the passcode may be any suitable password, passphrase, or the like. After block 512 is executed, the reader-printer processor 244 is directed to execute block 514.

Block 514 directs the reader-printer processor 244 to receive as user input the passcode. After the passcode is received, the reader-printer processor 244 is directed to execute block 516.

Block 516 directs the reader-printer processor 244 to determine whether the received passcode is associated in memory, such as the read-printer memory 246 (FIG. 8), with the matched biometric profile determined by block 510.

If the received passcode is not associated with or otherwise does not match the determined biometric profile, then the reader-printer processor 244 is directed to return to block 506. Returning to block 506 may involve producing an error message or executing other error handling blocks of code.

If the received passcode is associated with or otherwise matches the determined biometric profile, then the reader-printer processor 244 is directed to return to the method 500 (FIG. 26) at block 518.

In some reader-printer embodiments, blocks 512 to 516 are optional and may not be included, or may be included but disabled. In some reader-printer embodiments, the user is permitted to selectably disable or enable execution of blocks 512 to 516. To disable blocks 512 to 516, the user may require an enhanced level of user or administrative rights, for example. Additionally or alternatively, blocks 506 to 510 and/or blocks 512 to 516 in various reader-printer embodiments form part of an initialization routine of the reader-printer 210, or may never be executed.

Referring back to FIG. 26, block 518 directs the reader-printer processor 244 to permit use by the user of the reader-printer 210, such as by enabling various functions of the reader-printer 210. For example, one or both of the reader system 214 and the printer system 216 may be enabled. Enabling a function of the reader-printer 210 may involve setting a flag or register value to indicate an associated functional feature of the reader-printer 210 is enabled.

Block 520 then directs the reader-printer processor 244 to cause the reader system 214 to authenticate the booklet 228 when it is presented by the user to the reader system 214. Authenticating the booklet 228 may include performing a verification of the booklet 228. Verifying the booklet 228 may involve determining whether information appearing on or otherwise coded in the booklet 228 in accordance with national or international standards indicates tampering of the booklet 228 has occurred.

Figure 28:
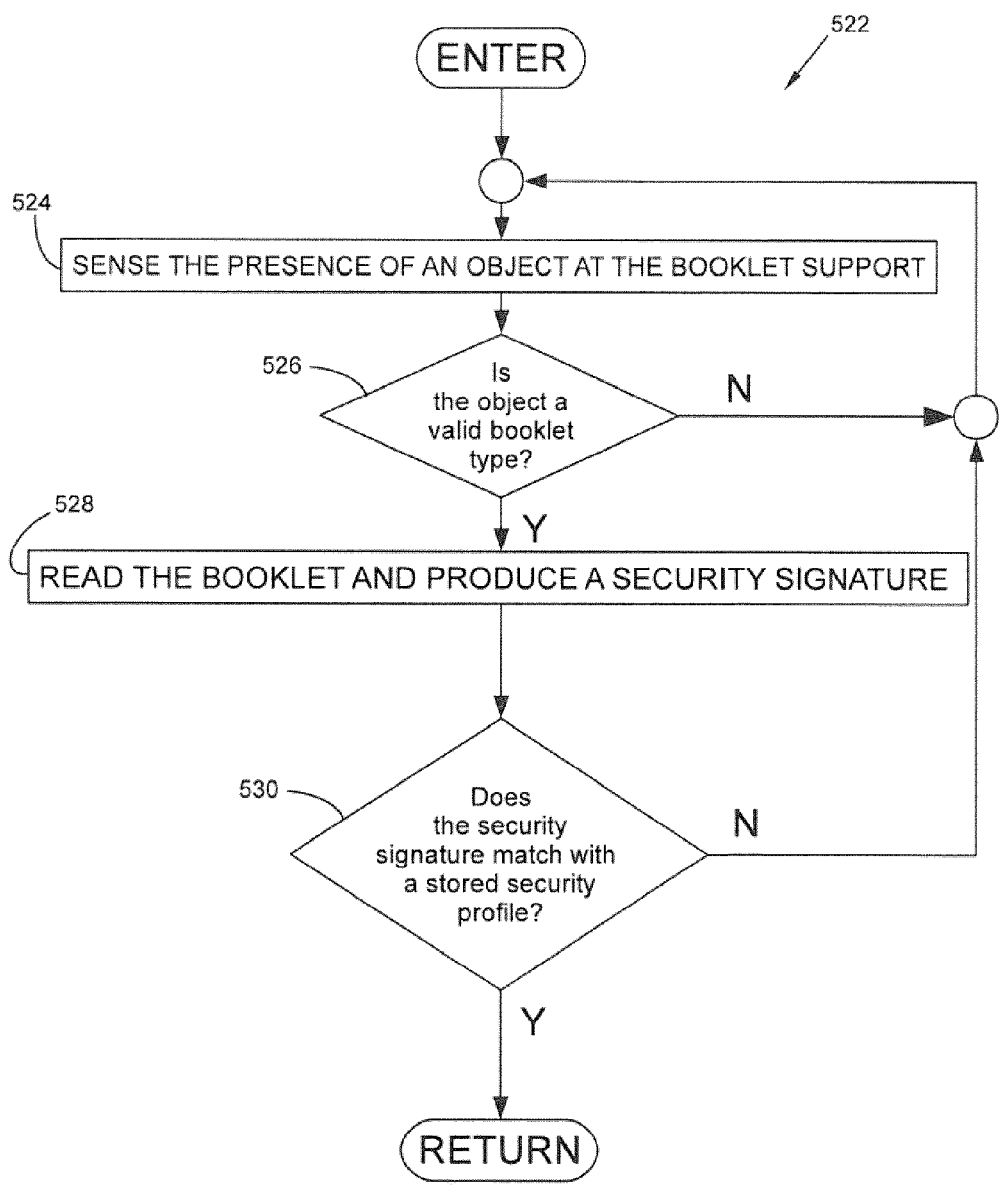
FIG. 28 is a flow diagram showing the method of FIG. 26 for authenticating the booklet.

FIG. 28 shows an exemplary method 522 for executing the block 520 (FIG. 26) in accordance with reader-printer embodiments of the invention. The method 522 begins by executing block 524.

Block 524 directs the reader-printer processor 244 to cause the reader-printer 210 to sense the presence of an object at the booklet support 230 (FIG. 7). Sensing the presence of an object at the booklet support 230 may involve receiving by the reader-printer processor 244 a reader sensor 236 output indicating an object is present at the booklet support 230. Additionally or alternatively, sensing the presence of an object at the booklet support 230 may involve receiving an output signal from a button or key of the reader-printer 210, such as one of the pushbuttons 226 (FIG. 7) or similar. After block 524 has been executed, the reader-printer processor 244 is directed to execute block 526.

Block 526 directs the reader-printer processor 244 to determine whether the object is a valid booklet type. Determining whether the object is a valid booklet type may involve determining whether the object matches a permitted type of the booklet 228. By way of explanation, each reader-printer 210 may be configured and/or programmed for authenticating and printing on one or more different types of booklets 228. For example, one reader-printer 210 may be configured and programmed for printing Visa stamps on passport booklets 228, while a different reader-printer 210 may be configured and programmed for printing identification information on newly issued passport booklets 228. Other examples are possible, including authenticating and/or printing any newly issued official paper, card, certificate or document; authenticating and/or printing approval stamps or the like on any official paper, card, certificate or other document; authenticating and/or printing a certification mark on any product label or product; other uses or any combination thereof. Any given reader-printer embodiment may be programmed to restrict printing to one or more types of value items.

Determining whether the object matches a permitted booklet 228 type may involve determining a measurement of one or more dimensions of the object in response to one or more reader sensor 236 outputs. Additionally or alternatively, determining whether the object matches a permitted booklet 228 type may involve receiving an image of the object, such as may be captured by an imaging device of the reader system 214 mounted within the reader-printer housing 212. In some reader-printer embodiments, the reader-printer processor 244 is directed to use image processing algorithms and techniques to determine a measurement of one or more dimensions of the object indicating the object's type; to determine whether identification information printed on the booklet 228 or any other known marking can be found on the object at an expected location; or any combination thereof.

If the reader-printer processor 244 determines by block 526 that the object does not match a valid booklet 228 type, then the reader-printer processor 244 is directed to return to block 524. Returning to block 524 may involve producing an error message or executing other error handling blocks of code.

If the reader-printer processor 244 determines by block 526 that the object does match a valid booklet 228 type, then the reader-printer processor 244 is directed to execute block 528.

Block 528 directs the reader-printer processor 244 to read the booklet 228 and produce a security signature. In some reader-printer embodiments, block 528 directs the reader-printer processor 244 to perform operations described in more detail in the U.S. Pat. No. 7,850,077 issued on Dec. 14, 2010 to Talwerdi et al. and in the United States patent application publication No. 2010/0073128 published on Mar. 25, 2010 to Talwerdi, the disclosures of both of which are incorporated herein by reference.

Additionally or alternatively, reading the booklet 228 may involve capturing an image of the booklet 228 when the booklet 228 is being received by the booklet support 230, including capturing images of the booklet 228 when the booklet 228 is being exposed to electromagnetic radiation having wavelengths in one or more ranges of the electromagnetic spectrum such as the infrared, visible light and ultraviolet ranges. Additionally or alternatively, reading the booklet 228 may involve using an image of the booklet 228 previously captured by block 526. Producing a security signature in response to the captured image of the booklet 228 may involve producing a digital representation of a material characteristic of a security feature of the booklet 228. Additionally or alternatively, producing a security signature in response to the captured image of the booklet 228 may involve producing a security signature for forensic analysis or other purposes, including for the comparison of potentially matching security features. The operation of block 528 may be configurable in various reader-printer embodiments to more specifically address particular uses of the security signature being produced, and multiple configurations may be available for execution in any given reader-printer embodiment, including having multiple configurations available in a given reader-printer embodiment for selection by the user. Selecting a particular configuration may require enhanced user or administrative rights, for example. When block 528 has been executed, the reader-printer processor 244 is directed to execute block 530.

Block 530 directs the reader-printer processor 244 to determine whether the security signature produced (generated) by block 526 matches a previously generated and stored security signature. The stored security signature may have been previously stored by use of the reader station 460 in a manner described herein above or otherwise previously stored, for example. Determining whether the produced security signature matches a stored security signature may involve retrieving the stored security signature from the read-printer memory 246 and comparing the produced security signature with the retrieved security signature; receiving the stored security signature by using the communications system 248 and comparing the produced security signature with the received security signature; transmitting by the communications system 248 the produced security signature to a remote destination (e.g. central server) and receiving a message or other indication from that remote destination specifying whether the produced security signature matches a stored security signature; or any combination thereof for example.

If the reader-printer processor 244 determines by block 530 that the produced security signature does not match a stored security signature, then the reader-printer processor 244 is directed to return to block 524. Returning to block 524 may involve producing an error message or executing other error handling blocks of code.

If the reader-printer processor 244 determines by block 530 that the produced security signature matches a stored security signature, then the reader-printer processor 244 is directed to return to the method 500 (FIG. 26) at block 532.

Referring back to FIG. 26, block 532 directs the reader-printer processor 244 to permit access to the printer system 216. Access may be permitted by releasing or unlocking the inlet flap 242, turning on the printer system 216 if not already on, and enabling the printer system 216 if not already enabled, for example. Permitting access may also involve moving components of the printer system to their receiving positions if such components are not already in their receiving positions, respectively.

In some reader-printer embodiments, block 520 is optional and need not be included or may be included but disabled. In some reader-printer embodiments, the user is permitted to selectably disable or enable execution of block 520. To disable block 520, the user may require an enhanced level of user or administrative rights, for example. When block 520 is bypassed, block 532 may be executed only once during initialization of the reader-printer 210, or may never be executed as access is permitted under all conditions.

Block 534 then directs the reader-printer processor 244 to cause the reader-printer 210 to determine the printing area for printing by the printer system 216. Typically, the printing area of the booklet 228 is confined within its printable area 440 (FIG. 13).

Figure 29:
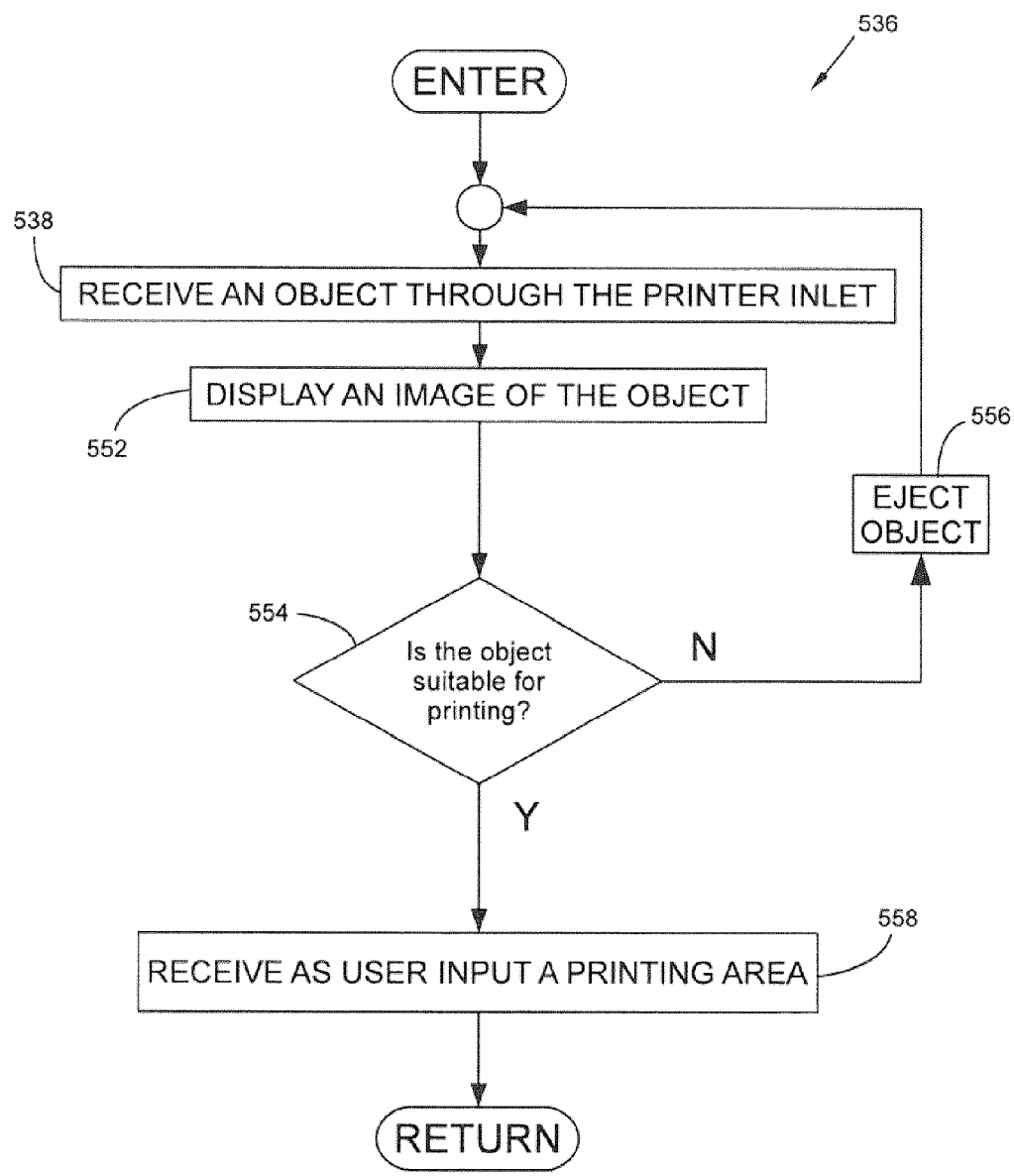
FIG. 29 is a flow diagram showing the method of FIG. 26 for determining a printing area.

FIG. 29 shows an exemplary method 536 for executing the block 534 (FIG. 26) in accordance with reader-printer embodiments of the invention. The method 536 begins by executing block 538.

Block 538 directs the reader-printer processor 244 to cause the printer system 216 to receive an object being inserted into the printer inlet 240 (FIGS. 7, 11, 15 and 16 to 17) by the user. Preferably, the printer system is in its receiving position when block 538 is executed. Receiving an object through the printer inlet 240 may involve releasing or unlocking the inlet flap 242 if it has not already been released, for example.

Figure 30:
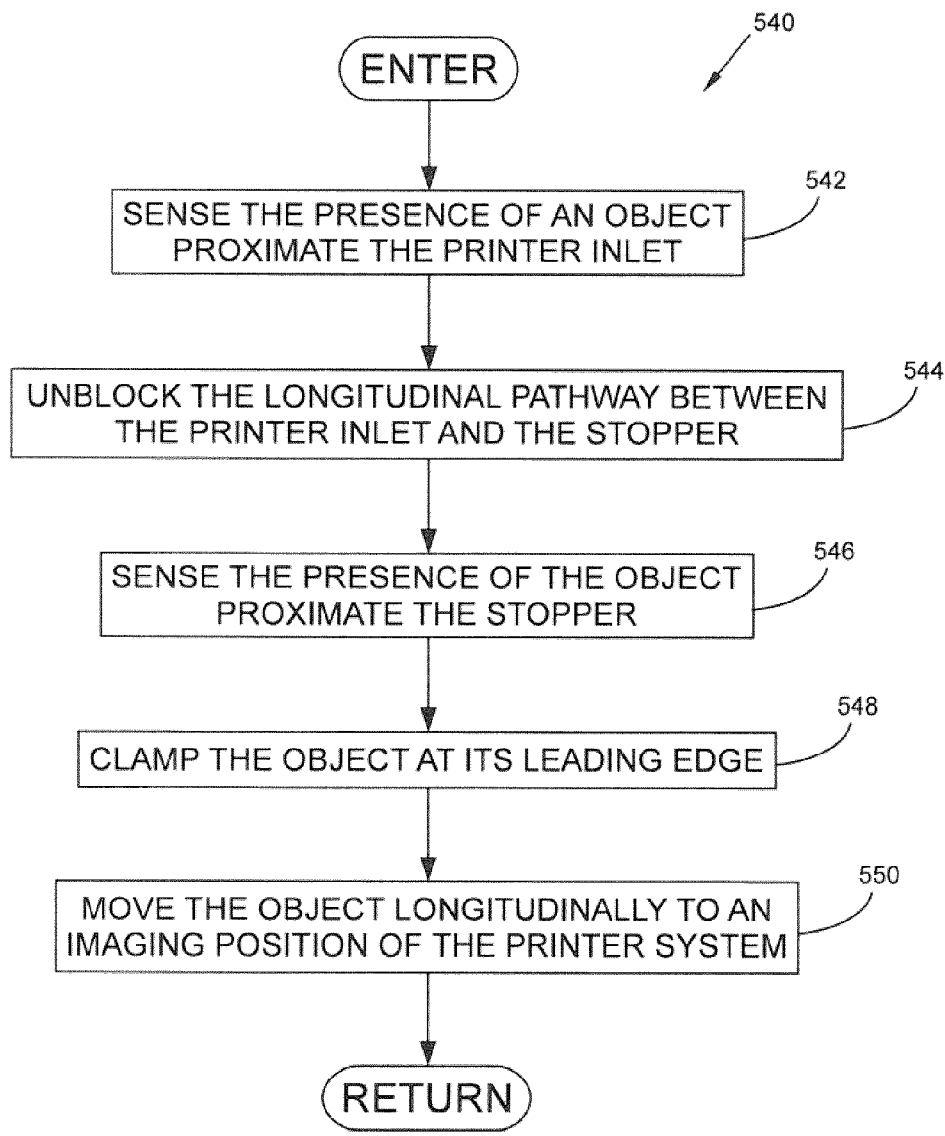
FIG. 30 is a flow diagram showing the method of FIG. 29 for receiving an object through the printer inlet.

FIG. 30 shows an exemplary method 540 for executing the block 538 (FIG. 29) in accordance with reader-printer embodiments of the invention. The method 540 begins by executing block 542.

Block 542 directs the reader-printer processor 244 to cause the transport system 254 (FIGS. 9 to 10, 11 to 14, 15 and 16 to 24) to sense the presence of an object proximate the printer inlet 240. Sensing the presence of an object proximate the printer inlet 240 may involve receiving a signal from one or more printer inlet 240 sensors (not shown) indicating the presence of an object which may be the leading edge 414 (FIG. 12) of a booklet 228 being inserted into the printer inlet 240 or otherwise at or near the printer inlet 240.

Block 544 then directs the reader-printer processor 244 to cause the transport system 254 to unblock the longitudinal pathway between the printer inlet 240 and a stopper, which in the first to third reader-printer embodiments is the stopper gate 272 (FIGS. 9, 12 and 15) and in the fourth embodiment is the backstop 456 (FIGS. 16 to 24). Unblocking the longitudinal pathway between the printer inlet 240 and the stopper may involve moving the printer system 216 to its receiving position, moving the platen 256 to a lowered position, moving the support plate 400 to a lowered position, contracting one or more of the platen posts 270, contracting one or more of the posts 406, unlocking the inlet flap 242, opening the inlet flap 242, performing other actions, or any combination thereof for example.

In some embodiments, block 544 or blocks 542 and 544 are not executed, such as where the printer system 216 is already in its printing position, or the longitudinal pathway between the printer inlet 240 and the stopper is otherwise already unblocked, upon commencement of the method 540.

Block 546 directs the reader-printer processor 244 to cause the transport system 254 to sense the presence of an object being proximate the stopper, which in the first to third reader-printer embodiments is the stopper gate 272 (FIGS. 9, 12 and 15) and in the fourth embodiment is the backstop 456 (FIGS. 16 to 24). Sensing the presence of an object proximate the stopper gate 272 may involve receiving a signal from one or more printer sensors (not shown) indicating the presence of an object which may be the leading edge 414 (FIG. 12) of an inserted booklet 228 adjacent or otherwise proximate to the stopper. For example, the transport system 254 of the fourth embodiment senses the presence of the leading edge 414 of the booklet 228 by the backstop 456 sensor described herein above.

Block 548 then directs the reader-printer processor 244 to cause the transport system 254 to clamp the object at its leading edge 414. In the first, third and fourth reader-printer embodiments, clamping the object at its leading edge 414 involves moving the platen 256 (FIGS. 9 to 10, 15 and 18) upwardly so as to clamp the object, such as the booklet 228, between the platen 256 and the upper frame plate 264 of the transport frame 260. In the second reader-printer embodiment, clamping the object at its leading edge 414 involves moving the lower clamping plate 412 (FIG. 11) upwardly so as to clamp the object, such as the booklet 228 at its leading edge 414, between the lower and upper clamping plates 412 and 410 of the clamping frame 408. Other variations for clamping the leading edge 414 of an object, such as the booklet 228, are possible and are within the contemplation of the present invention.

In the first to third reader-printer embodiments, clamping the object at its leading edge 414 also involves moving the platen 256 (of the first and third reader-printer embodiments) and the support plate 400 (of the second reader-printer embodiment) upwardly so as to possibly contact or even clamp the object, such as the booklet 228, in an non-edge area thereof between the platen 256 or the support plate 400 and the second feeding roller 286. Clamping the booklet 228 between the platen 256 or the support plate 400 and the second feeding roller 286 may also cause the first feeding roller 286 to make contact with the upper surface of the booklet 228 at a non-edge area thereof. However, in variations, the platen 256 or the support plate 400 need not be moved upwardly when the object is being clamped at its leading edge 414. When the object has been clamped at its leading edge by executing block 548, the method proceeds to block 550.

Block 550 directs the reader-printer processor 244 to move the object longitudinally to an imaging position of the printer system 216. The imaging position may be defined as the longitudinal position of the transport frame 260 (FIGS. 9 to 10, 15 and 16 to 24) or the clamping frame 408 (FIGS. 11 to 14) when line-of-sight is achieved between the value item and an imaging device 460 (FIG. 20) of the printer system 216. In some reader-printer embodiments, the imaging device 460 is mounted within the reader-printer housing 212 and directed toward the top surface of the booklet 228 where a printable area of the booklet 228 is typically located. Moving the object longitudinally to the imaging position advantageously permits the printer system 216 to capture images of the object using the imaging device 460.

In the first, third and fourth reader-printer embodiments, moving the object longitudinally to an imaging position involves moving the transport frame 260 and the platen 256 together longitudinally, such as by longitudinally moving the rack 416 (e.g. FIG. 20). In the second reader-printer embodiment, moving the object longitudinally to an imaging position involves moving the clamping frame 408 (FIGS. 11 to 14) longitudinally along with the rack 416 (FIGS. 11 to 14).

In the first to third reader-printer embodiments, block 550 is optional and may not be executed, such as where the reader-printer 210 is dimensioned such that the receiving position of the printer system 216 is such that the transport system 254 is already in a position that permits imaging of the booklet 228 immediately upon execution of block 546. In some reader-printer embodiments, imaging is possible immediately after executing block 546.

In various embodiments, during execution of any of blocks 546 to 550, the reader-printer processor 244 may also be directed to cause the inlet flap 242 to lock in a closed position so as to prevent the insertion of more than one object through the printer inlet 240 at the same time.

When the method 540 is completed, the process returns to the method 536 (FIG. 29) at block 552.

Referring back to FIG. 29, block 552 directs the reader-printer processor 244 to display an image of the object. Displaying an image of the object may involve capturing an image, including possibly a streaming video of images, of the booklet 228 by the imaging device 460; and displaying the captured image on the reader-printer display 222 (FIG. 7) or the display (not shown) of a connected computer or other computing device in wired or wireless communication with the reader-printer 210.

Block 554 then directs the reader-printer processor 244 to determine whether the object is suitable for printing. In some reader-printer embodiments, determining whether the object is suitable for printing involves determining whether the image captured by block 552 matches the authenticated booklet 228 as previously determined by block 530 (FIG. 28). Additionally or alternatively, determining whether the object is suitable for printing may involve performing automated image analysis of the image captured by block 552 to determine whether visual features, such as a document identification code appearing on the object, match expected visual features such as a previously stored document identification. Additionally or alternatively, determining whether the object is suitable for printing may involve performing automated image analysis of the image captured by block 552 to determine whether visual features of the object correspond to a printable area of a known booklet 228 type. Additionally or alternatively, determining whether the object is suitable for printing involves receiving as user input an indication, such as a keystroke or actuation of a pushbutton 226 for example, that the image displayed by block 448 is acceptable to the user. Other checks may be performed to determine whether the correct booklet 228 has been inserted through the printer inlet 240, whether the inserted booklet 228 was properly inserted (e.g. at the correct page, oriented the correct way, not upside down, etc.), whether the inserted booklet 228 was properly clamped and possibly moved by the printer system 216 (e.g. no printer jam), whether the exposed printable area is of proper dimensions (e.g. sufficient blank space within the printable area to print a stamp or other markings without overlapping other existing stamps or other markings already appearing on the booklet 228), other error checks, or any combination thereof for example.

If block 554 determines that the object is not suitable for printing, the reader-printer processor 244 is directed to execute block 556.

Block 556 directs the reader-printer processor 244 to eject the object as unsuitable for printing. Ejecting the object may involve ejecting the object via the exit ramp 418 (FIGS. 10 and 11 to 14) while skipping the printing on the object. Alternatively, the printer system 216 may be operable to reverse eject the object out the printer inlet 240 (FIGS. 7, 10, 14, 15 and 20). Ejecting the object may also involve producing an error message or executing other error handling blocks of code.

After executing block 556, the process returns to block 538. Returning to block 538 may involve re-locking the inlet flap 242 or an outlet flap (not shown), if any.

If block 554 determines that the object is suitable for printing, the reader-printer processor 244 is directed to execute block 558.

Block 558 directs the reader-printer processor 244 to receive as user input a printing area. In some reader-printer embodiments, receiving as user input a printing area involves receiving user input that defines a display location (e.g. pixel coordinates) and/or a geometrical shape (e.g. rectangle, circle, etc.) corresponding to part or all of an image, which typically is the image displayed by block 552, being displayed on a display, which in some reader-printer embodiments is the reader-printer display 222. The printing area may be defined by user input created by operation of a touch-screen display, a computer mouse, trackball, keyboard or pushbutton 226 entry, voice command, other user input devices or techniques, or any combination thereof. Additionally or alternatively, the printing area may be determined by the reader-printer processor 244 by performing automated image analysis of an image, such as the image obtained by block 552. In some reader-printer embodiments, block 558 is not executed.

After executing block 558, the process returns to the method 500 (FIG. 26) at block 560.

Referring back to FIG. 26, block 560 directs the reader-printer processor 244 to print on the authenticated booklet 228 (FIG. 7), within the printing area. Printing within the printing area typically involves printing within the printing area received as user input by block 558 (FIG. 29). Printing typically involves operating the printhead 274 (FIGS. 9, 11 to 14, and 15) in any suitable manner, including causing the printhead 274 to move transversely along a printhead guide (not shown).

In some reader-printer embodiments, printing involves first moving the printer system 216 and the booklet 228 from the imaging position of the printer system 216 to the print-start or other printing position of the printer system 216. For example, in some reader-printer embodiments the imaging position places the booklet 228 at a different vertical height 266 (FIG. 9) than the printing position. In some reader-printer embodiments, the booklet 228 is moved some distance away from the printing position and then moved the booklet 228 toward the printing position.

In the first, third and fourth reader-printer embodiments, printing on different print lines involves pulling the booklet 228 clamped at its leading edge 414 by effecting longitudinal movement of the platen 256 and the transport frame 260 in a direction which may be away from the printer inlet 240, toward the printer outlet 252, or both away from the printer inlet 240 and toward the printer outlet 252 for example. In the second reader-printer embodiment, printing on different print lines involves pulling the booklet 228 clamped at its leading edge 414 (FIG. 11) by effecting longitudinal movement of the clamping frame 408 (FIG. 11) in a direction which may be away from the printer inlet 240, toward the printer outlet 252, or both away from the printer inlet 240 and toward the printer outlet 252 for example.

Longitudinal movement of the platen 256 and the transport frame 260 or the clamping frame 408 may be effected by any suitable linear motion system, including possibly mechanisms and techniques described herein above. For example, the printer system 216 may be operable to cause longitudinal movement of the clamping frame 408 along with the rack 416.

In the first to fourth reader-printer embodiments, the printer system 216 is operable, after all desired printing is completed, to continue pulling the booklet 228 until the booklet 228 is at an ejection position of the printer system 216 which is suitable for subsequent ejection of the booklet 228 out of the reader-printer 210, unless the printing operation itself resulted in the booklet 228 being at the ejection position (e.g. where printing occurred on the last available printing line within the printable area 440 and the resulting printed position coincides with the ejection position of the printer system 216).

Upon completion of printing by executing block 560, the method proceeds to block 562.

Block 562 directs the reader-printer processor 244 to cause the printer system 216 to release the printed booklet 228. Releasing the printed booklet 228 may involve moving the booklet 228 longitudinally to an ejection position of the printer system 216 if the booklet 228 is not already at the ejection position of the printer system 216.

Figure 31:
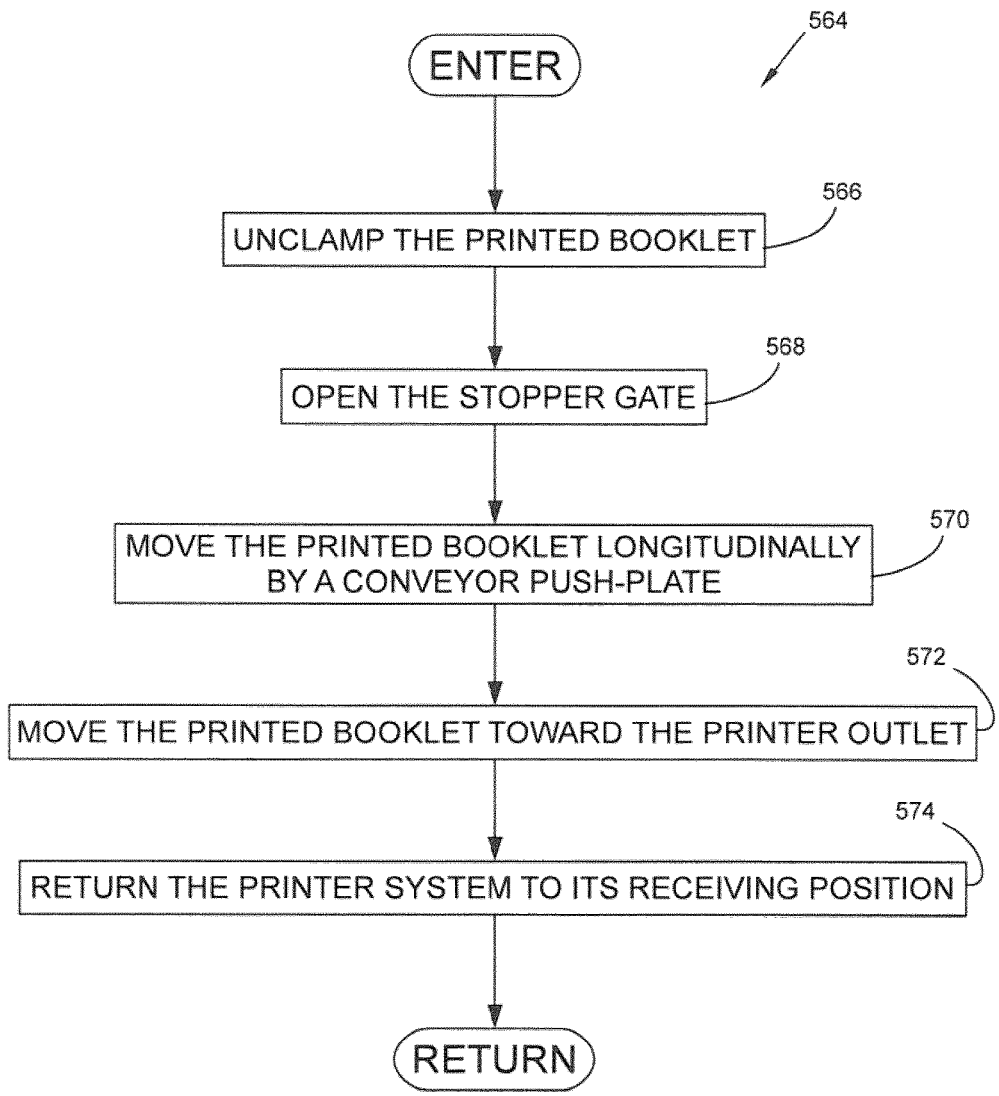
FIG. 31 is a flow diagram showing the method of FIG. 26 for releasing the object in accordance with the first, second and third reader-printer embodiments of the invention.

FIG. 31 shows an exemplary method 564 for executing the block 562 (FIG. 26) in accordance with the first to third reader-printer embodiments of the invention. The method 564 begins by executing block 566.

Block 566 directs the reader-printer processor 244 to cause the transport system 254 to unclamp the printed booklet 228.

In the first and third reader-printer embodiments, unclamping the printed booklet 228 involves lowering the platen 256 (FIGS. 9 and 15) so that the printed booklet 228 is no longer clamped between the platen 256 and the transport frame 260 (FIGS. 9 and 15).

In the second reader-printer embodiment, unclamping the printed booklet 228 involves lowering the lower clamping plate 412 (FIGS. 11 to 14) so that the printed booklet 228 is no longer clamped between the lower clamping plate 412 and the upper clamping plate 410 (FIGS. 11 to 14). In the second reader-printer embodiment, the booklet support 400 (FIGS. 11 to 14) may also be lowered when the lower clamping plate 412 is being lowered, although in some circumstances it may not be necessary to lower the booklet support 400 in order for the booklet 228 to become unclamped. In general, the booklet support 400 may be lowered at any time prior to insertion of the leading edge 414 of a subsequent object into the space defined between the upper and lower clamping plates 410 and 412. After block 566 has been executed, the reader-printer processor 244 is directed to execute block 568.

Block 568 directs the reader-printer processor 244 to cause the stopper gate 272 (FIGS. 9, 11 to 14, and 15) to be opened. Opening the stopper gate 272 may involve rotating the stopper gate 272 about a hinged connection between the stopper gate 272 and the transport frame 260 (first and third reader-printer embodiments) or the clamping frame 408 (second reader-printer embodiment). In the first to third reader-printer embodiments, opening the stopper gate 272 involves rotating the stopper gate 272 about its hinged connection to lower the stopper gate 272 and move the stopper gate 272 away from the booklet 228 toward the printer outlet 252. In various reader-printer embodiments, the stopper gate 272 may be rotated from a ninety-degrees vertical stopping position to a zero-degrees horizontal position, to a raised angular position (e.g. between zero and ninety degrees) to form a ramp to assist removal of the booklet 228 toward the printer outlet 252, or to a lowered angular position (less than zero degrees), for example. In some reader-printer embodiments, rotating the stopper gate 272 involves raising the stopper gate 272, such as where the hinged connection is located at an upper end of the stopper gate 272. Other mechanisms for implementing the stopper gate 272 are also possible. For example, linear vertical motion of the stopper gate 272 may open and close the stopper gate 272.

While FIG. 31 shows block 568 being executed immediately after block 566, block 568 may be executed at any time after the booklet 228 has been clamped (e.g. any time after executing block 548 of FIG. 30) and at any time before executing block 570 described herein below. In some reader-printer embodiments, the stopper gate 272 is moved to multiple opened positions at different times during execution of the method 500. After block 568 has been executed, the reader-printer processor 244 is directed to execute block 570.

Block 570 directs the reader-printer processor 244 to cause the printed booklet 228 (FIG. 7) to be moved longitudinally by operation of a transport conveyor push-plate, which may be the push-plate 280 (FIG. 9) of the first reader-printer embodiment or may be one or both of the push-plates 442 (FIGS. 14 and 15) of the second and third reader-printer embodiments for example. Moving the printed booklet 228 longitudinally typically involves pushing the printed booklet 228 at its trailing edge by the push-plate 280 or one or both of the push-plates 442. Moving the printed booklet 228 longitudinally also typically involves moving the printed booklet 228 through the transport frame 260 (FIG. 9) or the clamping frame 408 (FIGS. 11 to 14). Preferably, the transport frame 260 and the clamping frame 408 are dimensioned to provide sufficient vertical clearance, when not clamping the booklet 228, to permit the booklet 228 to pass through the transport frame 260 or the clamping frame 408 without making contact with the printed surface of the booklet 228, thereby advantageously avoiding the possibility of smudging recently printed ink. Longitudinal movement of the printed booklet 228 may be effected by any suitable linear motion system, including possibly mechanisms and techniques described herein above. After block 570 has been executed, the reader-printer processor 244 is directed to execute block 572.

Block 572 directs the reader-printer processor 244 to cause the printed booklet 228 (FIG. 7) to be moved toward the printer outlet 252 (FIG. 8). Moving the printed booklet 228 toward the printer outlet 252 may involve partly or fully ejecting the printed booklet 228 from the transport system 254 (FIGS. 9 to 10, 11 to 14, and 15), or performing any other action to place the printer system 216 in its ejection position. In the first or third reader-printer embodiment, moving the printed booklet 228 toward the printer outlet 252 involves conveying the printed booklet 228 by operation of the exit conveyor 296 (FIG. 10) along the incline 300, including possibly pushing the printed booklet 228 at its trailing edge by the exit push-plate 312 (FIG. 10). In the second or third reader-printer embodiment, moving the printed booklet 228 toward the printer outlet 252 involves clamping the printed booklet 228 by the exit clamp 424 (FIGS. 11 to 14) and moving the exit clamp 424 longitudinally along the exit ramp 418 (FIGS. 11 to 14). Other ejection systems are possible, including mechanisms and techniques described herein above. In some reader-printer embodiments, ejecting the printed booklet 228 from the printer outlet 252 involves unlocking and/or opening an outlet flap (not shown) before or as moving the printed booklet 228 toward the printer outlet 252. Additionally or alternatively, ejecting the printed booklet 228 from the printer outlet 252 may involve re-locking and/or re-closing the outlet flap (not shown) after having moved the printed booklet 228 past the printer outlet 252 or after sensing the printed booklet 228 having been pulled by the user past the printer outlet 252 for example.

In some reader-printer embodiments, block 570 need not be executed, such as where the reader-printer housing 212 is dimensioned such that the printed booklet 228 becomes accessible to the user at the printer outlet 252 solely by executing block 570 for example.

After block 572 has been executed, the method proceeds to block 574.

Block 574 directs the reader-printer processor 244 to cause the printer system 216 (FIG. 8) to return to its receiving position.

In the first reader-printer embodiment, returning the printer system 216 to its receiving position involves any of the following operations if not already done: (a) moving the platen 256 (FIG. 9) and the transport frame 260 (FIG. 9) longitudinally to a position close to the printer inlet 240 such that the leading edge of a subsequently inserted booklet 228 can reach the transport frame 260; (b) returning the transport frame 260 to its unclamped position; (c) closing the stopper gate 272, such as by rotating the stopper gate 272 to become vertically oriented; (d) moving conveyor belt 278 (FIG. 9) so that one push-plate 280 (FIG. 9) is close to the printer outlet 252 but not in a position to interfere with the insertion of a subsequent booklet 228; and (e) moving the exit conveyor 296 (FIG. 10) so that one exit push-plate 312 is distal from the printer outlet 252 but not in a position to interfere with a subsequent booklet 228 being passed through the transport frame 260.

In the second reader-printer embodiment, returning the printer system 216 to its receiving position involves any of the following operations if not already done: (a) moving the clamping frame 408 (FIGS. 11 to 14) longitudinally to a position close to the printer inlet 240 such that the leading edge 414 of a subsequently inserted booklet 228 can reach the clamping frame 408; (b) returning the clamping frame 408 to its unclamped position; (c) closing the stopper gate 272, such as by rotating the stopper gate 272 to become vertically oriented; (d) moving the conveyors 402 so that one push-plate 442 per conveyor 402 is close to the printer outlet 252 but not in a position to interfere with the insertion of a subsequent booklet 228; and (e) unclamping the exit clamp 424 and moving it to a position distal from the printer outlet 252.

In the third reader-printer embodiment, returning the printer system 216 to its receiving position may involve any application operation described herein above in respect of returning the printer system 216 to its receiving position in accordance with the first reader-printer embodiment, the second reader-printer embodiment, or both the first and second reader-printer embodiments for example.

Other operations are possible, such as setting the inlet flap 242 and the outlet flap, if any, to a locked or unlocked position or to an open or closed position, for example.

After block 574 has been executed, the process returns to end the method 500 (FIG. 26). In some reader-printer embodiments, ending the method 500 involves returning the process to block 502. Alternatively, ending the method 500 may involve returning the process to block 506 (FIG. 27) without the need for the user to be re-identified for each new printing.

Figure 32:
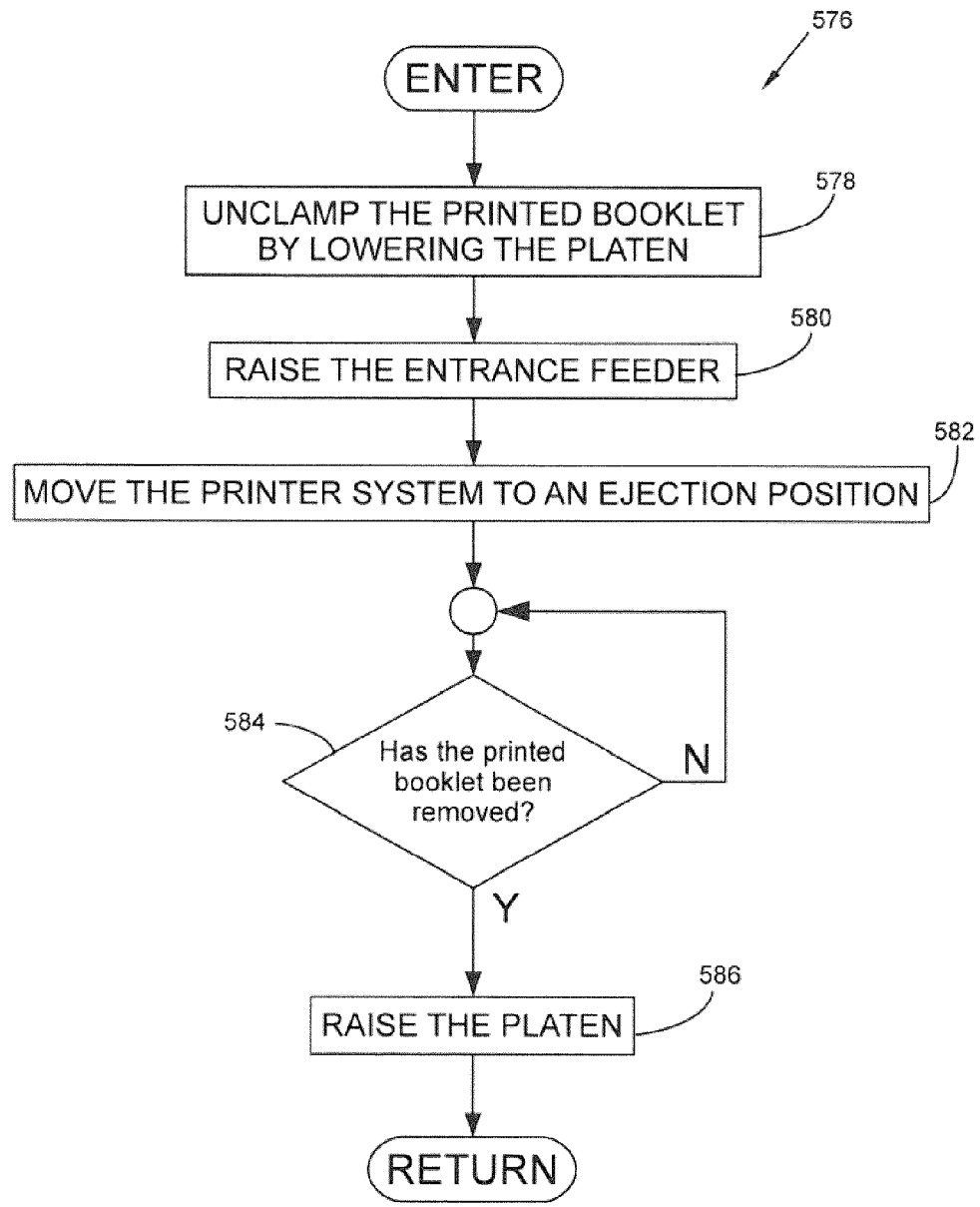
FIG. 32 is a flow diagram showing the method of FIG. 26 for releasing the object in accordance with the fourth reader-printer embodiment of the invention.

FIG. 32 shows an exemplary method 576 for executing the block 562 (FIG. 26) in accordance with the fourth reader-printer embodiment of the invention. The method 576 begins by executing block 578.

Block 578 directs the reader-printer processor 244 to cause the transport system 254 to unclamp the printed booklet 228 by lowering the platen 256. Block 578 may be executed in a manner that is identical, similar or analogous to the execution of block 566 in respect of the first and third reader-printer embodiments, for example.

Block 580 then directs the reader-printer processor 244 to cause the transport system 254 to raise the entrance feeder 448. Raising the entrance feeder 448 may involve activating a solenoid-driven plunger (not visible in the Figures) to result in contact between the entrance feeder 448 and the entrance feeder stopper 454, for example. Raising the entrance feeder 448 advantageously reduces or eliminates contact between the booklet 228 and the first and second rollers 284 and 286 when the booklet 228 is being transported by the transport system 254 toward the printer inlet 240 which in the fourth embodiment is also the printer outlet 252.

Block 582 then directs the reader-printer processor 244 to cause the transport system 254 to move the printer system 216 to its ejection position. Moving the printer system 216 to its ejection position may involve moving the platen 256 and the transport frame 260 longitudinally by any suitable linear motion system, including possibly mechanisms and techniques described herein above such as longitudinally with the rack 416. In the fourth embodiment, moving the printer system 216 to its ejection position involves moving the platen 256 and the transport frame 260 longitudinally toward the printer inlet 240 such that the backstop 456 pushes on the trailing edge of the booklet 228 while at least a portion of the booklet 228 passes underneath the raised entrance feeder 448. After block 582 has been executed, the reader-printer processor 244 is directed to execute block 584.

Block 584 directs the reader-printer processor 244 to determine whether the printed booklet 228 has been removed from the transport system 254. Determining whether the printed booklet 228 has been removed from the transport system 254 may involve sensing by one or more ejection sensors (not shown) the removal of the booklet 228 from the transport system 254 or entirely from the reader-printer 210. Determining whether the printed booklet 228 has been removed from the transport system 254 may involve receiving an indication from the one or more ejection sensors that the booklet 228 has been removed. In some embodiments, determining whether the printed booklet 228 has been removed from the transport system 254 involves receiving an indication from an entrance sensor that the booklet 228 has been removed.

If by block 584 the reader-printer processor 244 determines that the booklet 228 has not been removed, the reader-processor 244 is directed to return to the beginning of block 584, thereby forming a wait loop.

If by block 584 the reader-printer processor 244 determines that the booklet 228 has been removed, the reader-processor 244 is directed to execute block 586.

Block 586 directs the reader-printer processor 244 to cause the transport system 254 to raise the platen 256. Raising the platen 256 may involve permitting the platen posts 270 to extend by any suitable mechanism, for example, so as to move the printer system 216 to a default position. In some embodiments, raising the platen 256 advantageously reduces power consumption and increases the lifespan of electromechanical components of the transport system 254, such as an electromechanical motor for causing the platen posts 270 to contract when lowering the platen 270. In some embodiments, block 586 also involves closing and/or locking the inlet flap 242. In some embodiments, block 586 is not executed. In embodiments in which block 586 is not executed, block 584 may also not be executed. In some embodiments, the printer system 216 remains in its ejection position at the conclusion of the method 576. Additionally or alternatively, the printer system 216 may be returned to its receiving position at the conclusion of the method 576. In some embodiments, the ejection and receiving positions coincide.

After block 586 has been executed, the process returns to end the method 500 (FIG. 26), which may involve returning the process to block 502 (FIG. 26), block 506 (FIG. 27) or block 520 (FIG. 26), for example.

While not shown in the Figures, the reader-printer processor 244 is generally operable in at least some reader-printer embodiments to record each step of a sequence that is taken by the reader-printer 210, such as by recording each step of the sequence in the read-printer memory 246. Additionally or alternatively, the reader-printer 210 may be operable to communicate, such as by communicating via the communications system 248 (FIG. 8), a log of recorded steps of the sequence to a central server (not shown). In some reader-printer embodiments, the reader-printer processor 244 is directed to record only selected operations, such as user identifications obtained by executing block 502 for example. In some reader-printer embodiments, block 502 to identify the user must be executed to permit access to troubleshooting and servicing features of the reader-printer processor 244 code, and each attempt to service the reader-printer 210 may be logged.

In general, executing any blocks of code which involve comparing specified quantities (e.g. blocks 510 and 516 of FIG. 27, blocks 526 and 530 of FIG. 28 and block 554 of FIG. 29), may involve comparing the specified quantities by the reader-printer processor 244 and/or by a remote device (e.g. central server) in electronic communication, such as via the communications system 248, with the reader-printer processor 244. Also, executing any blocks of code which involve retrieving a stored quantity (e.g. block 510 of FIG. 27 and blocks 526 and 530 of FIG. 28) may involve retrieving the stored quantity from the read-printer memory 246 and/or receiving the stored quantity from the remote device via the communications system 248.

Thus, there is provided a method of reading and printing on an object, the method comprising: (a) reading the object by a reader system of a reader-printer; (b) obtaining by the reader-printer a digital signature representing a unique feature of the object; and (c) printing on the object by a printer system of the reader-printer if the digital signature matches a reference digital signature associated with the object.

Security Checkpoint with Reader-Printer Functions

With reference to FIGS. 1 to 32, the security checkpoint 10 in accordance with some embodiments of the invention includes the reader-printer 210, or a portion thereof, in accordance with one or more embodiments of the reader-printer 210 in any combination thereof. For example, any one or more of the biometric scanner 220, reader-printer display 222, reader system 214, power management system of the reader-printer 210, reader-printer processor 244, reader-printer memory 246, communications system 248, location identification system 250, printer system 216 and the transport system 254 in accordance with any embodiments thereof may be incorporated into the security checkpoint 10.

By way of further specific examples, in some embodiments the fingerprint scanner 40 of the security checkpoint 10 is operable to perform some or all of the scanning functions of the biometric scanner 220 of the reader-printer 210; in some embodiments, the palm-print scanner of the security checkpoint 10 is operable to perform some or all of the scanning functions of the biometric scanner 220 of the reader-printer 210; in some embodiments, the display 38 of the security checkpoint 10 is operable to perform some or all of the display functions of the reader-printer display 222 of the reader-printer 210; in some embodiments, the document scanner 42 of the security checkpoint 10 is operable to perform some or all of the scanning functions of the reader system 214 of the reader-printer 210; in some embodiments, the passport reader 134 of the security checkpoint 10 is operable to perform some or all of the reading functions of the reader system 214 of the reader-printer 210; in some embodiments, the controller 54 of the security checkpoint 10 is operable to perform some or all of the processing functions associated with the reader-printer processor 244; in some embodiments, the processor 56 of the security checkpoint 10 is operable to perform some or all of the processing functions associated with the reader-printer processor 244; in some embodiments, the memory 58 of the security checkpoint 10 is operable to perform some or all of the data storage functions associated with the reader-printer memory 246; in some embodiments, the communications controller 64 of the security checkpoint 10 is operable to effect some or all of the communications functions associated with the communications system 248 of the reader-printer 210; and in some embodiments, the printer 136 of the security checkpoint 10 is operable to perform some or all of the printing functions associated with the printer system 216 of the reader-printer 210.

Furthermore in some embodiments, the security checkpoint 10 includes one or more of the modules 450 to 462 of the modular system 448 in any combination. In variations, the security checkpoint 10 may include any combination of the reader-printer 210 and one or more of the modules 450 to 462.

By way of a non-limiting example, the security checkpoint 10 in some embodiments includes the reader-printer 210 and the RFID station 454 for processing documents and other value items containing RFID elements (not shown) or otherwise having RFID technology associated therewith.

In general, however, the security checkpoint 10 in accordance with any embodiment thereof may be operable to perform one or more functions described herein above in relation to the reader-printer 210 in accordance with any embodiment thereof and may include one or more components described herein above in relation to the reader-printer 210 in accordance with any embodiment thereof.

While embodiments of the invention have been described and illustrated, such embodiments should be considered illustrative of the invention only. The invention may include variants not described or illustrated herein in detail. Thus, the embodiments described and illustrated herein should not be considered to limit the invention as construed in accordance with the accompanying claims.

The invention claimed is:

1. A security checkpoint system, comprising:
   (a) a one-way mirror for concealingly permitting automated collection of data related to a person at a security checkpoint;
   (b) recording equipment for recording said data, said recording equipment being concealed from the person by said one-way mirror; and
   (c) a document scanner arranged to scan a document carried by the person,
   wherein the data recorded by the recording equipment is automatically compared to the data produced by the document scanner, and
   wherein the security checkpoint is operable to display information on the one-way mirror so that the information is visible to persons present at the security checkpoint.

2. A security checkpoint system according to claim 1, further comprising an analysis device, wherein the data recorded by the recording equipment is sent to the analysis device for analysis.

3. A security checkpoint system according to claim 2, further comprising at least one of an alarm device and a visual indication device to indicate a result of the analysis.

4. A security checkpoint system according to claim 2, wherein the analysis device is configured to analyze the recorded data.

5. A security checkpoint system according to claim 2, further comprising an exit gate moveable between a closed position and an open position, the exit gate being configured, depending upon a result of the analysis of the recorded data, to move from the closed position to the open position.

6. A security checkpoint system according to claim 1, further comprising a housing configured to support the one-way mirror and the recording equipment being located in the housing and behind the one-way mirror.

7. A security checkpoint system according to claim 1, wherein the recording equipment comprises at least one of: a camera, a stereoscopic camera, an audio recorder, a proximity detector, a thermal sensor, a tactile sensor, a vibration sensor, a fingerprint detector, a palm-print detector, a magnetic energy detector, an infrared light source, a visible light source, an ultraviolet light source and a heat source.

8. A security checkpoint system according to claim 1, wherein the recording equipment comprises at least one of: an ultrasonic transducer, a monochrome charge coupled device array camera, a near infrared radiation source and a pulse oximeter.

9. A security checkpoint system according to claim 1, further comprising a printer to print a stamp on an identity document.

10. A security checkpoint system according to claim 1, wherein the one-way mirror is configured to display information visible to at least the person at the security checkpoint.

11. A method of operating a security checkpoint system, the method comprising executing by a processor the steps of:
   (a) automated collection of data related to a person at a security checkpoint from behind a one-way mirror;
   (b) recording the data with recording equipment concealed by the one-way mirror;
   (c) scanning with a document scanner a document carried by the person, and
   (d) automatically comparing the data recorded by the recording equipment to the data produced by the document scanner, wherein the security checkpoint is operable to display information on the one-way mirror so that the information is visible to persons present at the security checkpoint.

12. A method according to claim 11, further comprising sending the recorded data to an analysis device for analysis.

13. A method according to claim 12, further comprising indicating a result of the analysis.

14. A method according to claim 12, further comprising, depending upon a result of the analysis, opening an exit gate.

15. A method according to claim 12, wherein the analysis comprises behavioral analysis.

16. A method according to claim 11, wherein the recorded data is at least one of: an image of a face of a person; a voice recording of the person; an image of a part of the body of the person; a fingerprint of the person; a palm-print of the person; a behavior of the person; and a body temperature of the person.

17. A method according to claim 11, wherein the recorded data is at least one of: a pulse of the person; the bone density of the person; a gait of the person; and a blood oxygen level of the person.

18. A method according to claim 11, further comprising displaying information on the one-way mirror is visible to at least the person at the security checkpoint.

19. A security checkpoint system, comprising:
a housing located at a security checkpoint;
a one-way mirror supported in the housing that is arranged to face a person seeking passage through the security checkpoint;
data collectors arranged within the housing and behind the one-way mirror that are configured to collect data related to the person, the data collectors being concealed from the person seeking passage by the one-way mirror;
data analyzers for analyzing the collected data for at least one of physical and behavioral characteristics of the person seeking passage;
a scanner arranged to read an object from the person seeking passage for analysis, wherein analysis of the scanned object provides identity information related to the person seeking passage, and
wherein a part of the one-way mirror is configured as a display viewable by the person seeking passage.

20. The security checkpoint system according to claim 19, wherein the scanner comprises at least one of a biometric scanner and a value document scanner.

* * * * *